United States Patent [19]
Chu et al.

[11] Patent Number: 5,284,841
[45] Date of Patent: Feb. 8, 1994

[54] BENZO-FUSED LACTAMS PROMOTE RELEASE OF GROWTH HORMONE

[75] Inventors: Lin Chu, Waldwick; Michael H. Fisher, Ringoes; Helmut Mrozik, Matawan; William R. Schoen, Edison, all of N.J.

[73] Assignee: Merck & Co., Inc., Rahway, N.J.

[21] Appl. No.: 13,448

[22] Filed: Feb. 4, 1993

[51] Int. Cl.$^5$ .................. A61K 31/55; C07D 209/34; C07D 215/227; C07D 223/16

[52] U.S. Cl. .................. 514/183; 514/213; 514/312; 514/418; 540/455; 540/460; 540/461; 540/491; 540/509; 540/523; 544/52; 544/105; 544/354; 546/158; 548/483

[58] Field of Search .............. 540/461, 523; 546/158; 548/483; 514/183, 213, 312, 418

[56] References Cited

U.S. PATENT DOCUMENTS

| | | | |
|---|---|---|---|
| 3,239,345 | 8/1966 | Hodge et al. | 514/450 |
| 4,036,979 | 7/1977 | Asato | 514/443 |
| 4,411,890 | 10/1983 | Momany | 514/17 |
| 4,692,522 | 9/1987 | Parsons et al. | 540/461 |
| 5,206,235 | 4/1993 | Fisher et al. | 540/523 |

FOREIGN PATENT DOCUMENTS

| | | |
|---|---|---|
| 166357 | 1/1986 | European Pat. Off. |
| 253310 | 1/1988 | European Pat. Off. |
| 291969 | 11/1988 | European Pat. Off. |
| 324377 | 7/1989 | European Pat. Off. |
| 349949 | 1/1990 | European Pat. Off. |
| 429257 | 11/1990 | European Pat. Off. |
| 430709 | 11/1990 | European Pat. Off. |
| 434249 | 11/1990 | European Pat. Off. |

OTHER PUBLICATIONS

Jones, et al J. Chem Soc. c. pp. 2176-12181 (1969).
Davis, et al. Arch. Biochem. Biophys 102 pp. 48-51 (1963).
Wattley, et al. J. Med. Chem. 28 pp. 1511-1516 (1985).
Slade, et al J. Med. Chem. 28 pp. 1517-1521 (1985).
Huang, et al. Synthesis, 10 p. 851 (1984).
Stewart, Australia J. Chem. 33 pp. 633-640 (1980).
Still, et al. J. Org. Chem. 43, pp. 2923 (1978).
Parsons, W. H., Med. Chem. vol. 32, pp. 1681-1685 (1989).

*Primary Examiner*—Cecilia Tsang
*Assistant Examiner*—Philip I. Datlow
*Attorney, Agent, or Firm*—David L. Rose; Joseph F. DiPrima

[57] ABSTRACT

There are disclosed certain novel compounds identified as benzo-fused lactams

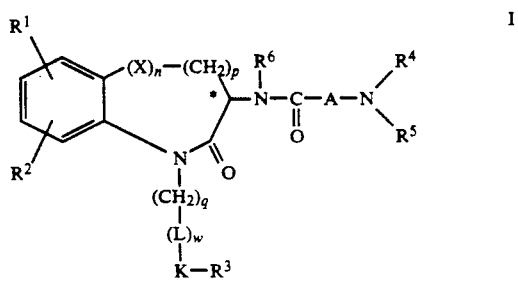

which promote the release of growth hormone in humans and animals. This property can be utilized to promote the growth of food animals to render the production of edible meat products more efficient, and in humans, to increase the stature of those afflicted with a lack of a normal secretion of natural growth hormone. The compounds are prepared by substitution of an amino-lactam with a substituted amide function. Growth promoting compositions containing such benzo-fused lactams as the active ingredient thereof are also disclosed.

8 Claims, No Drawings

BENZO-FUSED LACTAMS PROMOTE RELEASE OF GROWTH HORMONE

BACKGROUND OF THE INVENTION

Growth hormone, which is secreted from the pituitary, stimulates growth of all tissues of the body that are capable of growing. In addition, growth hormone is known to have the following basic effects on the metabolic process of the body:

1. Increased rate of protein synthesis in all cells of the body;
2. Decreased rate of carbohydrate utilization in cells of the body;
3. Increased mobilization of free fatty acids and use of fatty acids for energy.

A deficiency in growth hormone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering an agent which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recently, recombinant growth hormone has become available which, while no longer carrying any risk of disease transmission is still a very expensive product which must be given by injection or by a nasal spray.

Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. The instant compounds are non-peptidyl agents for promoting the release of growth hormone which may be administered parenterally, nasally or by the oral route.

SUMMARY OF THE INVENTION

The instant invention covers certain benzo-fused lactam compounds which have the ability to stimulate the release of natural or endogenous growth hormone. The compounds thus have the ability to be used to treat conditions which require the stimulation of growth hormone production or secretion such as in humans with a deficiency of natural growth hormone or in animals used for food production where the stimulation of growth hormone will result in a larger, more productive animal. Thus, it is an object of the instant invention to describe the benzo-fused lactam compounds. It is a further object of this invention to describe procedures for the preparation of such compounds. A still further object is to describe the use of such compounds to increase the secretion of growth hormone in humans and animals. A still further object of this invention is to describe compositions containing the benzo-fused lactam compounds for the use of treating humans and animals so as to increase the level of growth hormone secretions. Further objects will become apparent from a reading of the following description.

DESCRIPTION OF THE INVENTION

The novel benzo-fused lactams of the instant invention are best described in the following structural formula I:

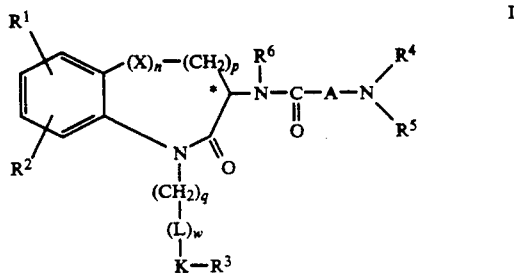

n is 0 or 1;
p is 0 to 3;
q is 0 to 4;
w is 0 or 1;
X is

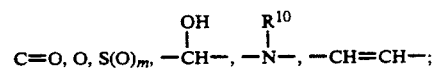

m is 0 to 2;
L and K are independently

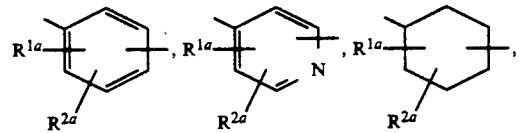

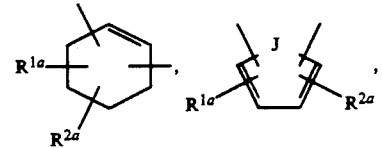

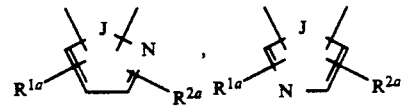

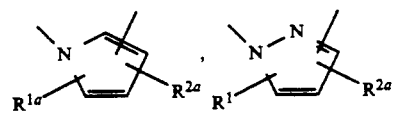

-continued

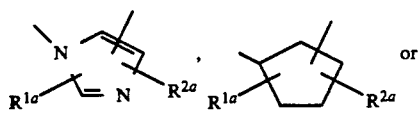

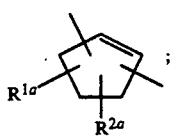

where J is O, S or N—$R^{13}$ with the proviso either L or K must be other than

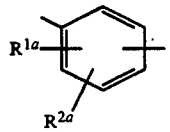

$R^1$, $R^2$, $R^{1a}$, and $R^{2a}$ are independently hydrogen, halogen, $C_1$-$C_7$ alkyl, $C_1$-$C_3$ perfluoroalkyl, $C_1$-$C_3$ perfluoroalkoxy, —$S(O)_mR^{7a}$, cyano, nitro, $R^{7b}O(CH_2)_v$—, $R^{7b}COO(CH_2)_v$—, $R^{7b}OCO(CH_2)_v$—, $R^4R^5N(CH_2)_v$—, $R^{7b}CON(R^4)(CH_2)_v$—, $R^4R^5NCO(CH_2)_v$—, phenyl or substituted phenyl where the substituents are from 1 to 3 of halogen, $C_1$-$C_6$ alkyl, $C_1$-$C_6$ alkoxy or hydroxy;

$R^{7a}$ and $R^{7b}$ are independently hydrogen, $C_1$-$C_3$ perfluoroalkyl, $C_1$-$C_6$ alkyl, substituted $C_1$-$C_6$ alkyl, where the substituents are phenyl or substituted phenyl; phenyl or substituted phenyl where the phenyl substituents are from 1 to 3 of halogen, $C_1$-$C_6$ alkyl, $C_1$-$C_6$ alkoxy or hydroxy and v is 0 to 3;

$R^3$ is hydrogen, $R^9$, $C_1$-$C_6$ alkyl substituted with $R^9$, phenyl substituted with $R^9$ or phenoxy substituted with $R^9$;

$R^9$ is

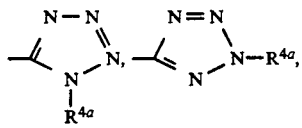

$R^{7b}O(CH_2)_v$—, $R^{7b}COO(CH_2)_v$—, $R^{7b}OCO(CH_2)_v$—, $R^{7b}CO(CH_2)_v$—, $R^{7b}O(CH_2)_vCO$—, $R^4R^5N(CH_2)_v$—, $R^{7b}CON(R^4)(CH_2)_v$—, $R^4R^5NCO(CH_2)_v$—, $R^4R^5NCS(CH_2)_v$—, $R^4R^5NN(R^5)CO(CH_2)_v$—, $R^4R^5NN(R^5)CS(CH_2)_v$—, $R^{7b}CON(R^4)N(R^5)CO(CH_2)_v$—, $R^{7b}CON(R^4)N(R^5)CS(CH_2)_v$—, $R^4N(OR^{7b})CO(CH_2)_v$—, $R^{7a}CON(OR^{7b})CO(CH_2)_v$—, $R^{4b}R^{12a}NCON(R^{12b})(CH_2)_v$—, $R^{4b}R^{12a}NCSN(R^{12b})(CH_2)_v$—, $R^{4b}R^{12a}NN(R^{12b})CSN(R^{12c})(CH_2)_v$—, $R^{4b}R^{12a}NN(R^{12b})CON(R^{12c})(CH_2)_v$—, $R^{4b}R^{12a}NN(R^{12b})COO(CH_2)_v$—, $R^{4b}R^{12a}NCOO(CH_2)_v$— or $R^{13}OCON(R^{12b})(CH_2)_v$—, where v is 0 to 3;

$R^{12a}$, $R^{12b}$ and $R^{12c}$ are independently $R^{5a}$, $OR^{5a}$, or $COR^{5a}$; $R^{12a}$ and $R^{12b}$, or $R^{12b}$ and $R^{12c}$, or $R^{13}$ and $R^{12b}$, or $R^{12a}$ and $R^{4b}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 3 and $R^1$ and $R^{10}$ are as defined;

$R^{13}$ is $C_1$-$C_3$ perfluoroalkyl, $C_1$-$C_6$ alkyl, substituted $C_1$-$C_6$ alkyl, where the substituents are hydroxy, —$NR^{10}R^{11}$, carboxy, phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy where $R^{10}$ and $R^{11}$ are independently hydrogen, $C_1$-$C_6$ alkyl, phenyl, phenyl $C_1$-$C_6$ alkyl, $C_1$-$C_5$-alkoxycarbonyl or $C_1$-$C_5$-alkanoyl-$C_1$-$C_6$ alkyl;

$R^4$, $R^{4a}$, $R^{4b}$, $R^5$ and $R^{5a}$ are independently hydrogen, phenyl, substituted phenyl, $C_1$-$C_{10}$ alkyl, substituted $C_1$-$C_{10}$ alkyl, $C_3$-$C_{10}$ alkenyl, substituted $C_3$-$C_{10}$ alkenyl, $C_3$-$C_{10}$ alkynyl or substituted $C_3$-$C_{10}$ alkynyl where the substituents on the phenyl, alkyl, alkenyl or alkynyl are from 1 to 5 of hydroxy, $C_1$-$C_6$ alkoxy, $C_3$-$C_7$ cycloalkyl, fluoro, $R^1$, $R^2$ independently disubstituted phenyl $C_1$-$C_3$ alkoxy, $R^1$, $R^2$ independently disubstituted phenyl, $C_1$-$C_{20}$ alkanoyloxy, $C_1$-$C_5$ alkoxycarbonyl, carboxy, formyl or —$NR^{10}R^{11}$; or $R^4$ and $R^5$ can be taken together to form —$(CH_2)_rB(CH_2)_s$— where B, r, s, $R^1$, $R^2$, $R^{10}$ and $R^{11}$ are as defined above;

$R^6$ is hydrogen, $C_1$-$C_{10}$ alkyl, phenyl or phenyl $C_1$-$C_{10}$ alkyl;

A is

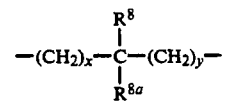

where x and y are independently 0–3;

$R^8$ and $R^{8a}$ are independently hydrogen, $C_1$-$C_{10}$ alkyl, trifluoromethyl, phenyl, substituted $C_1$-$C_{10}$ alkyl where the substituents are from 1 to 3 of imidazolyl, indolyl, hydroxy, fluoro, $S(O)_mR^{7a}$, $C_1$-$C_6$ alkoxy, $C_3$-$C_7$ cycloalkyl, $R^1$, $R^2$ independently disubstituted phenyl $C_1$-$C_3$ alkoxy, $R^1$, $R^2$ independently disubstituted phenyl, $C_1$-$C_5$ alkanoyloxy, $C_1$-$C_5$ alkoxycarbonyl, carboxy, formyl or —$NR^{10}R^{11}$ where $R^1$, $R^2$, $R^{10}$ and $R^{11}$ are as defined above; or $R^8$ and $R^{8a}$ can be taken together to form —$(CH_2)_t$— where t is 2 to 6; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms;

and pharmaceutically acceptable salts thereof.

In the above structural formula and throughout the instant specification, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The alkoxy groups specified above are intended to include those alkoxy groups of the designated length in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy and the like.

The term "halogen" is intended to include the halogen atoms fluorine, chlorine, bromine and iodine.

Certain of the above defined terms may occur more than once in the above formula and upon such occurrence each term shall be defined independently of the other.

Preferred compounds of the instant invention are realized when in the above structural formula:

n is 0 or 1;
p is 0 to 3;
q is 0 to 2;
w is 0 or 1;
L and K are as defined above;
X is O, $S(O)_m$,

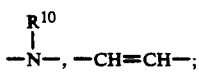

m is 0 to 2;

$R^1$, $R^2$, $R^{1a}$ and $R^{2a}$ are independently hydrogen, halogen, $C_1$-$C_7$ alkyl, $C_1$-$C_3$ perfluoroalkyl, —$S(O)_mR^{7a}$, $R^{7b}O(CH_2)_v$—, $R^{7b}COO(CH_2)_v$—, $R^{7b}OCO(CH_2)_v$—, phenyl or substituted phenyl where the substituents are from 1 to 3 of halogen, $C_1$-$C_6$ alkyl, $C_1$-$C_6$ alkoxy or hydroxy;

$R^{7a}$ and $R^{7b}$ are independently hydrogen, $C_1$-$C_3$ perfluoroalkyl, $C_1$-$C_6$ alkyl, substituted $C_1$-$C_6$ alkyl, where the substituents are phenyl; phenyl and v is 0 to 2;

$R^3$ is hydrogen, $R^9$, $C_1$-$C_6$ alkyl substituted with $R^9$, phenyl substituted with $R^9$ or phenoxy substituted with $R^9$;

$R^9$ is

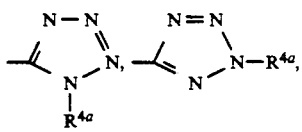

$R^{7b}O(CH_2)_v$—, $R^{7b}COO(CH_2)_v$—, $R^{7b}OCO(CH_2)_v$—, $R^{7b}CO(CH_2)_v$—, $R^4R^5N(CH_2)_v$—, $R^{7b}CON(R^4)(CH_2)_v$—, $R^4R^5NCO(CH_2)_v$—, $R^4R^5NCS(CH_2)_v$—, $R^4R^5NN(R^5)CO(CH_2)_v$—, $R^{7b}CON(R^4)N(R^5)CO(CH_2)_v$—, $R^4N(OR^{7b})CO(CH_2)_v$—, $R^{7a}CON(OR^{7b})CO(CH_2)_v$—, $R^{4b}R^{12a}NCON(R^{12b})(CH_2)_v$—, $R^{4b}R^{12a}NCSN(R^{12b})(CH_2)_v$—, $R^{4b}R^{12a}NN(R^{12b})CON(R^{12c})(CH_2)_v$—, $R^{4b}R^{12a}NN(R^{12b})COO(CH_2)_v$—, $R^{4b}R^{12a}NCOO(CH_2)_v$— or $R^{13}OCON(R^{12b})(CH_2)_v$—, where v is 0 to 3;

$R^{12a}$, $R^{12b}$ and $R^{12c}$ are independently $R^{5a}$, $OR^{5a}$, or $COR^{5a}$; $R^{12a}$ and $R^{12b}$, or $R^{12b}$ and $R^{12c}$, or $R^{13}$ and $R^{12b}$ or $R^{12a}$ and $R^{4b}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 3, $R^1$ is as defined above and $R^{10}$ is hydrogen, $C_1$-$C_6$ alkyl, phenyl $C_1$-$C_6$ alkyl or $C_1$-$C_5$ alkanoyl-$C_1$-$C_6$ alkyl;

$R^{13}$ is $C_1$-$C_3$ perfluoroalkyl, $C_1$-$C_6$ alkyl, substituted $C_1$-$C_6$ alkyl, where the substituents are hydroxy, —$NR^{10}R^{11}$, carboxy, phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy; where $R^{10}$ and $R^{11}$ are as defined;

$R^4$, $R^{4a}$, $R^{4b}$, $R^5$ and $R^{5a}$ are independently hydrogen, phenyl, substituted phenyl, $C_1$-$C_{10}$ alkyl, substituted $C_1$-$C_{10}$ alkyl, where the substituents on the alkyl or phenyl are from 1 to 5 of hydroxy, $C_1$-$C_6$ alkoxy, $C_3$-$C_7$ cycloalkyl, fluoro, $R^1$, $R^2$ independently disubstituted phenyl $C_1$-$C_3$ alkoxy, $R^1$, $R^2$ independently disubstituted phenyl, $C_1$-$C_{20}$-alkanoyloxy, $C_1$-$C_5$ alkoxycarbonyl, carboxy or formyl; or $R^4$ and $R^5$ can be taken together to form —$(CH_2)_rB(CH_2)_s$— where B is $CHR^1$, O, $S(O)_m$ or N—$R^{10}$, r and s are independently 1 to 3 and $R^1$ and $R^{10}$ are as defined above;

$R^6$ is hydrogen, $C_1$-$C_{10}$ alkyl or phenyl $C_1$-$C_{10}$ alkyl;

A is

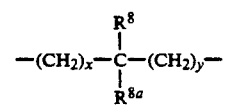

where x and y are independently 0-2;

$R^8$ and $R^{8a}$ are independently hydrogen, $C_1$-$C_{10}$ alkyl, substituted $C_1$-$C_{10}$ alkyl where the substituents are from 1 to 3 of imidazolyl, indolyl, hydroxy, fluoro, $S(O)_mR^{7a}$, $C_1$-$C_6$ alkoxy, $R^1$, $R^2$ independently disubstituted phenyl, $C_1$-$C_5$-alkanoyloxy, $C_1$-$C_5$ alkoxycarbonyl, carboxy, formyl or —$NR^{10}R^{11}$ where $R^{10}$ and $R^{11}$ are independently hydrogen, $C_1$-$C_6$ alkyl, or $C_1$-$C_5$ alkanoyl-$C_1$-$C_6$ alkyl;

or $R^8$ and $R^{8a}$ can be taken together to form —$(CH_2)_t$— where t is 2 to 4;

and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms;

and pharmaceutically acceptable salts thereof.

Additional preferred compounds are realized in the above structural formula when:

n is 0 or 1;
p is 0 to 2;
q is 0 to 2;
w is 0 or 1;
L and K are defined as above;
X is $S(O)_m$ or —CH=CH—;
m is 0 or 1;

$R^1$, $R^2$, $R^{1a}$ and $R^{2a}$ are independently hydrogen, halogen, $C_1$-$C_7$ alkyl, $C_1$-$C_3$ perfluoroalkyl, —$S(O)_mR^{7a}$, $R^{7b}O(CH_2)_v$—, $R^{7b}COO(CH_2)_v$—, $R^{7b}OCO(CH_2)_v$—, phenyl or substituted phenyl where the substituents are from 1 to 3 of halogen, $C_1$-$C_6$ alkyl, $C_1$-$C_6$ alkoxy, or hydroxy;

$R^{7a}$ and $R^{7b}$ are independently hydrogen, $C_1$-$C_6$ alkyl, substituted $C_1$-$C_6$ alkyl, where the substituents are phenyl and v is 0 to 2;

$R^3$ is hydrogen, $R^9$, $C_1$-$C_6$ alkyl substituted with $R^9$, phenyl substituted with $R^9$, or phenoxy substituted with $R^9$;

$R^9$ is

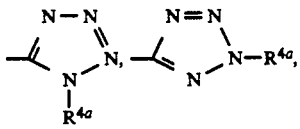

$R^{7b}O(CH_2)_v—$, $R^{7b}COO(CH_2)_v—$, $R^{7b}OCO(CH_2)_v—$, $R^{7b}CO(CH_2)_v—$, $R^4R^5N(CH_2)_v—$, $R^{7b}CON(R^4)(CH_2)_v—$, $R^4R^5NCO(CH_2)_v—$, $R^4R^5NCS(CH_2)_v—$, $R^4N(OR^{7b})CO(CH_2)_v—$, $R^{7a}CON(OR^{7b})CO(CH_2)_v—$, $R^{4b}R^{12a}NCON(R^{12b})(CH_2)_v—$, $R^{4b}R^{12a}NCSN(R^{12b})(CH_2)_v—$, $R^{4b}R^{12a}NN(R^{12b})CON(R^{12c})(CH_2)_v—$, $R^{4b}R^{12a}NN(R^{12b})COO(CH_2)_v—$, $R^{4b}R^{12a}NCOO(CH_2)_v—$ or $R^{13}OCON(R^{12b})(CH_2)_v—$, where v is 0 to 2;

$R^{12a}$, $R^{12b}$ and $R^{12c}$ are independently $R^{5a}$ or $OR^{5a}$. $R^{12a}$ and $R^{12b}$, or $R^{12b}$ and $R^{12c}$, or $R^{13}$ and $R^{12b}$ or $R^{12a}$ and $R^{4b}$ can be taken together to form $—(CH_2)_r—B—(CH_2)_s—$ where B is $CHR^1$, O, $S(O)_m$ or $NR^{10}$, m is 0, 1 or 2, r and s are independently 0 to 2, $R^1$ is as defined above and $R^{10}$ is hydrogen, $C_1-C_6$ alkyl or $C_1-C_5$ alkanoyl-$C_1-C_6$ alkyl;

$R^{13}$ is $C_1-C_6$ alkyl, substituted $C_1-C_6$ alkyl, where the substituents are phenyl or substituted phenyl; phenyl or substituted phenyl where the substituents on the phenyl are from 1 to 3 of halogen, $C_1-C_6$ alkyl, $C_1-C_6$ alkoxy or hydroxy;

$R^4$, $R^{4a}$, $R^{4b}$, $R^5$ and $R^{5a}$ are independently hydrogen, $C_1-C_{10}$ alkyl, substituted $C_1-C_{10}$ alkyl, where the substituents on the alkyl are from 1 to 5 of hydroxy, $C_1-C_6$ alkoxy, fluoro, $R^1$, $R^2$ independently disubstituted phenyl, $C_1-C_{20}$-alkanoyloxy, $C_1-C_5$ alkoxycarbonyl or carboxy;

$R^6$ is hydrogen or $C_1-C_{10}$ alkyl;

A is

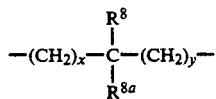

where x and y are independently 0–1;

$R^8$ and $R^{8a}$ are independently hydrogen, $C_1-C_{10}$ alkyl, substituted $C_1-C_{10}$ alkyl where the substituents are from 1 to 3 of imidazolyl, indolyl, hydroxy, fluoro, $S(O)_m R^{7a}$, $C_1-C_6$ alkoxy, $R^1$, $R^2$ independently disubstituted phenyl, $C_1-C_5$-alkanoyloxy, $C_1-C_5$ alkoxycarbonyl, carboxy; or $R^8$ and $R^{8a}$ can be taken together to form $—(CH_2)_t—$ where t is 2; or $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms; and pharmaceutically acceptable salts thereof.

Still further preferred compounds of the instant invention are realized in the above structural formula when;

n is 0 or 1;
p is 0 to 2;
q is 1;
w is 1;
L and K are defined as above;
X is $S(O)_m$ or $—CH=CH—$;

m is 0 or 1;

$R^1$, $R^2$, $R^{1a}$ and $R^{2a}$ are independently hydrogen, halogen, $C_1-C_7$ alkyl, $C_1-C_3$ perfluoroalkyl, $—S(O)_m R^{7a}$, $R^{7b}O(CH_2)_v—$, $R^{7b}COO(CH_2)_v—$, phenyl or substituted phenyl where the substituents are from 1 to 3 of halogen, $C_1-C_6$ alkyl, $C_1-C_6$ alkoxy, or hydroxy; $R^{7a}$ and $R^{7b}$ are independently hydrogen, $C_1-C_6$ alkyl, substituted $C_1-C_6$ alkyl, where the substituents are phenyl and v is 0 or 1;

$R^3$ is hydrogen, $R^9$, or $C_1-C_6$ alkyl substituted with $R^9$;

$R^9$ is

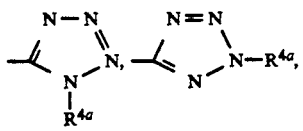

$R^{7b}O(CH_2)_v—$, $R^{7b}COO(CH_2)_v—$, $R^{7b}OCO(CH_2)_v—$, $R^{7b}CO(CH_2)_v—$, $R^{7b}CON(R^4)(CH_2)_v—$, $R^4R^5NCO(CH_2)_v—$, $R^4N(OR^{7b})CO(CH_2)_v—$, $R^{4b}R^{12a}NCON(R^{12b})(CH_2)_v—$, $R^{4b}R^{12a}NN(R^{12b})CON(R^{12c})(CH_2)_v—$, $R^{4b}R^{12a}NN(R^{12b})COO(CH_2)_v—$, $R^{4b}R^{12a}NCOO(CH_2)_v—$ or $R^{13}OCON(R^{12b})(CH_2)_v—$, where v is 0 to 2;

$R^{12a}$, $R^{12b}$ and $R^{12c}$ are independently $R^{5a}$. $R^{12a}$ and $R^{12b}$, or $R^{12b}$ and $R^{12c}$, or $R^{13}$ and $R^{12b}$ or $R^{12a}$ and $R^{4b}$ can be taken together to form $—(CH_2)_r—B—(CH_2)_s—$ where B is $CHR^1$, O, $S(O)_m$ or $NR^{10}$, m is 0, 1 or 2, r and s are independently 0 to 2, $R^1$ is as defined above and $R^{10}$ is hydrogen, $C_1-C_6$ alkyl or $C_1-C_5$ alkanoyl-$C_1-C_6$ alkyl;

$R^{13}$ is $C_1-C_6$ alkyl, substituted $C_1-C_6$ alkyl, where the substituents are phenyl or substituted phenyl; phenyl or substituted phenyl where the substituents on the phenyl are from 1 to 3 of halogen, $C_1-C_6$ alkyl, $C_1-C_6$ alkoxy or hydroxy;

$R^4$, $R^{4a}$, $R^{4b}$, $R^5$ and $R^{5a}$ are independently hydrogen, $C_1-C_{10}$ alkyl, substituted $C_1-C_{10}$ alkyl, where the substituents on the alkyl are from 1 to 3 of hydroxy, $C_1-C_3$ alkoxy, fluoro, $R^1$, $R^2$ independently disubstituted phenyl, $C_1-C_{20}$ alkanoyloxy, $C_1-C_5$ alkoxycarbonyl or carboxy;

$R^6$ is hydrogen;

A is

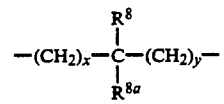

where x and y are independently 0–1;

$R^8$ and $R^{8a}$ are independently hydrogen, $C_1-C_{10}$ alkyl, substituted $C_1-C_{10}$ alkyl where the substituents are from 1 to 3 of imidazolyl, indolyl, hydroxy, fluoro, $S(O)_m R^{7a}$, $C_1-C_6$ alkoxy, $R^1$, $R^2$ independently disubstituted phenyl, $C_1-C_5$-alkanoyloxy, $C_1-C_5$ alkoxycarbonyl, carboxy; or $R^8$ and $R^{8a}$ can be taken together to form $—(CH_2)_t—$ where t is 2; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms;

and pharmaceutically acceptable salts thereof.

Representative examples of the nomenclature employed are given below:

3-Amino-N-[1-[[3-[2-(1H-tetrazol-5-yl)phenyl]-5-isoxazolyl]methyl]-2,3,4,5-tetrahydro-2-oxo-1H-1-benzazepin-3(R)-yl]-3-methylbutanamide

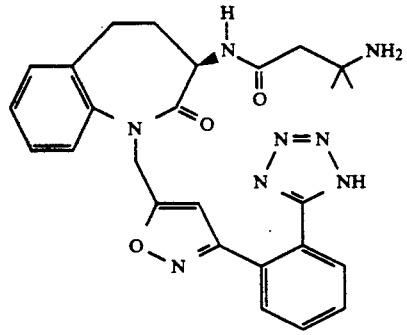

2-Amino-N-[1[[5-[2-(1H-tetrazol-5-yl)-phenyl]-2-thienyl]methyl]-2,3,4,5-tetrahydro-2-oxo-1H-1-benzazepin-3(R)-yl]-2-methylpropanamide

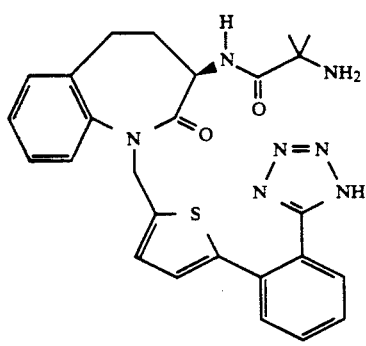

3-[2(R)-Hydroxypropyl]amino-N-[1-[[4-[2-(1H-tetrazol-5-yl)-phenyl]-cyclohexenyl]methyl]-2,3,4,5-tetrahydro-2-oxo-1H-1-benzazepin-3(R)-yl]-3-methylbutanamide

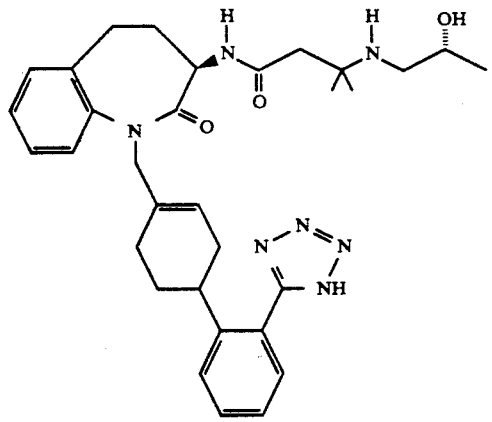

3-[2(R)-Hydroxypropyl]amino-N-[5-[4-[2-(1H-tetrazol-5-yl)-3-thienyl]-benzyl]-2,3,4,5-tetrahydro-4-oxo-5H-1,5-benzothiazepin-3(S)-yl]-3-methylbutanamide Representative preferred growth hormone releasing compounds of the present invention include the following:

1. 3-Amino-N-[1-[[3-(2-carboxamidophenyl)-5-isoxazolyl]methyl]-2,3,4,5-tetrahydro-2-oxo-1H-1-benzazepin-3(R)-yl]-3-methylbutanamide
2. 3-Amino-N-[1-[[3-(2-[1H-tetrazol-5-yl]-phenyl)-5-isoxazolyl]methyl]-2,3,4,5-tetrahydro-2-oxo-1H-1-benzazepin-3(R)-yl]-3-methylbutanamide
3. 3-Amino-N-[1-[[3-(2-[methylaminocarbonylamino]phenyl)-5-isoxa-zolyl]methyl]-2,3,4,5-tetrahydro-2-oxo-1H-1-benzazepin-3(R)-yl]-3-methylbutanamide
4. 3-[2(R)-Hydroxypropyl]amino-N-[1-[[3-(2-carboxamidophenyl)-5-isoxazolyl]methyl]-2,3,4,5-tetrahydro-2-oxo-1H-1-benzazepin-3(R)-yl]-3-methylbutanamide
5. 2-Amino-N-[1-[[3-(2-[1H-tetrazol-5yl]-phenyl)-5-isoxazolyl]methyl]-2,3,4,5-tetrahydro-2-oxo-1H-1-benzazepin-3(R)-yl]-2-methylpropanamide
6. 3-Amino-N-[5-[[3-(2-[1H-tetrazol-5-yl]-phenyl)-5-isoxazolyl]methyl]-2,3,4,5-tetrahydro-4-oxo-5H-1,5-benzothiazepin-3(S)-yl]-3-methylbutanamide
7. 3-Amino-N-[1-[[5-(2-carboxamidophenyl)-2-thienyl]-methyl]-2,3,4,5-tetrahydro-2-oxo-1H-1-benzazepin-3(R)-yl]-3-methylbutanamide
8. 3-Amino-N-[1-[[5-(2-[1H-tetrazol-5-yl]-phenyl)-2-thienyl]methyl]-2,3,4,5-tetrahydro-2-oxo-1H-1-benzazepin-3(R)-yl]-3-methylbutanamide
9. 3-Amino-N-[1-[[5-(2-[methylaminocarbonylamino]phenyl)-2-thienyl]-methyl]-2,3,4,5-tetrahydro-2-oxo-1H-1-benzazepin-3(R)-yl]-3-methylbutanamide
10. 3-[2(R)-Hydroxypropyl]amino-N-[1-[[5-(2-carboxamidophenyl)-2-thienyl]methyl]-2,3,4,5-tetrahydro-2-oxo-1H-1-benzazepin-3(R)-yl]-3-methylbutanamide
11. 2-Amino-N-[1-[[5-(2-[1H-tetrazol-5-yl]-phenyl)-2-thienyl]methyl]-2,3,4,5-tetrahydro-2-oxo-1H-1-benzazepin-3(R)-yl]-2-methylpropanamide
12. 3-Amino-N-[1-[[5-(2-[1H-tetrazol-5-yl]-phenyl)-2-thienyl]methyl]-2,3,4,5-tetrahydro-4-oxo-5H-1,5-benzothiazepin-3(S)-yl]-3-methylbutanamide
13. 3-Amino-N-[1-[4-(2-carboxamido-3-thienyl)-benzyl]-2,3,4,5-tetrahydro-2-oxo-1H-1-benzazepin-3(R)-yl]-3-methylbutanamide
14. 3-Amino-N-[1-[4-(2-[1H-tetrazol-5-yl]-3-thienyl)-benzyl]-2,3,4,5-tetrahydro-2-oxo-1H-1-benzazepin-3(R)-yl]-3-methylbutanamide
15. 3-Amino-N-[1-[4-(2-[methylaminocarbonylamino]-3-thienyl)-benzyl]-2,3,4,5-tetrahydro-2-oxo-1H-1-benzazepin-3(R)-yl]-3-methylbutanamide
16. 3-[2(R)-Hydroxypropyl]amino-N-[1-[4-(2-carboxamido-3-thienyl)-benzyl]-2,3,4,5-tetrahydro-2-oxo-1H-1-benzazepin-3(R)-yl]-3-methylbutanamide 17. 2-Amino-N-[1-[4-(2-[1H-tetrazol-5-yl]-3-thienyl)-benzyl]-2,3,4,5-tetrahydro-2-oxo-1H-1-benzazepin-3(R)-yl]-2-methylpropanamide
18. 3-Amino-N-[5-[4-(2-[1H-tetrazol-5-yl]-3-thienyl)-benzyl]-2,3,4,5-tetrahydro-4-oxo-5H-1,5-benzothiazepin-3(S)-yl]-3-methylbutanamide
19. 3-Amino-N-[1-[[4-(2-carboxamidophenyl)-cyclohexyl]methyl]-2,3,4,5-tetrahydro-2-oxo-1H-1-benzazepin-3(R)-yl]-3-methylbutanamide
20. 3-Amino-N-[1-[[4-(2-[1H-tetrazol-5-yl]-phenyl)-cyclohexyl]methyl]-2,3,4,5-tetrahydro-2-oxo-1H-1-benzazepin-3(R)-yl]-3-methylbutan-amide
21. 3-Amino-N-[1-[[4-(2-[methylaminocarbonylamino]-phenyl)cyclo-hexyl]methyl]-2,3,4,5-tetrahydro-2-oxo-1H-1-benzazepin-3(R)-yl]-3-methylbutanamide
22. 3-[2(R)-Hydroxypropyl]amino-N-[1-[[4-(2-carboxamidophenyl)cyclo-hexyl]methyl]-2,3,4,5-tetrahydro-2-oxo-1H-1-benzazepin-3(R)-yl]-3-methylbutanamide
23. 2-Amino-N-[1-[[4-(2-[1H-tetrazol-5-yl]-phenyl)-cyclohexyl]methyl]-2,3,4,5-tetrahydro-2-oxo-1H-1-benzazepin-3(R)-yl]-2-methylpropanamide
24. 3-Amino-N-[5-[[4-(2-[1H-tetrazol-5-yl]-phenyl)-cyclohexyl]methyl]-2,3,4,5-tetrahydro-4-oxo-5H-1,5-benzothiazepin-3(S)-yl]-3-methylbutanamide
25. 3-Amino-N-[1-[[4-(2-carboxamidophenyl)-cyclohexenyl]methyl]-2,3,4,5-tetrahydro-2-oxo-1H-1-benzazepin-3(R)-yl]-3-methylbutanamide
26. 3-Amino-N-[1-[[4-(2-[1H-tetrazol-5-yl]-phenyl)-cyclohexenyl]methyl]-2,3,4,5-tetrahydro-2-oxo-1H-1-benzazepin-3(R)-yl]-3-methylbutanamide
27. 3-Amino-N-[1-[[4-(2-[methylaminocarbonylamino]-phenyl)cyclo-hexenyl]methyl]-2,3,4,5-tetrahydro-2-oxo-1H-1-benzazepin-3(R)-yl]-3-methylbutanamide
28. 3-[2(R)-Hydroxypropyl]amino-N-[1-[[4-(2-carboxamidophenyl)-cyclo-hexenyl]methyl]-2,3,4,5-tetrahydro-2-oxo-1H-1-benzazepin-3(R)-yl]-3-methylbutanamide
29. 2-Amino-N-[1-[[4-(2-[1H-tetrazol-5-yl]-phenyl)-cyclohexenyl]methyl]-2,3,4,5-tetrahydro-2-oxo-1H-1-benzazepin-3(R)-yl]-2-methylpropanamide
30. 3-Amino-N-[5-[[4-(2-[1H-tetrazol-5-yl]-phenyl)-cyclohexenyl]methyl]-2,3,4,5-tetrahydro-4-oxo-5H-1,5-benzothiazepin-3(S)-yl]-3-methylbutanamide
31. 3-Amino-N-[1-[4-(4-carboxamido-5-oxazolyl)-benzyl]-2,3,4,5-tetrahydro-2-oxo-1H-1-benzazepin-3(R)-yl]-3-methylbutanamide
32. 3-Amino-N-[1-[4-(4-[1H-tetrazol-5-yl]-5-oxazolyl)-benzyl]-2,3,4,5-tetrahydro-2-oxo-1H-1-benzazepin-3(R)-yl]-3-methylbutanamide
33. 3-Amino-N-[1-[4-(4-[methylaminocarbonylamino]-5-oxazolyl)-benzyl]-2,3,4,5-tetrahydro-2-oxo-1H-1-benzazepin-3(R)-yl]-3-methylbutanamide
34. 3-[2(R)-Hydroxypropyl]amino-N-[1-[4-(4-carboxamido-5-oxazolyl)-benzyl]-2,3,4,5-tetrahydro-2-oxo-1H-1-benzazepin-3(R)-yl]-3-methylbutanamide
35. 2-Amino-N-[1-[4-(4-[1H-tetrazol-5-yl]-5-oxazolyl)-benzyl]-2,3,4,5-tetrahydro-2-oxo-1H-1-benzazepin-3(R)-yl]-2-methylpropanamide
36. 3-Amino-N-[5-[4-(4-[1H-tetrazol-5-yl]-5-oxazolyl)-benzyl]-2,3,4,5-tetrahydro-4-oxo-5H-1,5-benzothiazepin-3(S)-yl]-3-methylbutanamide
37. 3-Amino-N-[1-[4-(4-bromo-2-carboxamido-1-pyrrolyl)-benzyl]-2,3,4,5-tetrahydro-2-oxo-1H-1-benzazepin-3(R)-yl]-3-methylbutanamide
38. 3-Amino-N-[1-[4-(4-bromo-2-[1H-tetrazol-5-yl]-1-pyrrolyl)-benzyl]-2,3,4,5-tetrahydro-2-oxo-1H-1-benzazepin-3(R)-yl]-3-methylbutanamide
39. 3-Amino-N-[1-[4-(4-bromo-2-[methylaminocarbonylamino]-1-pyrrolyl)-benzyl]-2,3,4,5-tetrahydro-2-oxo-1H-1-benzazepin-3(R)-yl]-3-methylbutanamide
40. 3-[2(R)-Hydroxypropyl]amino-N-[1-[4-(4-bromo-2-carboxamido-1-pyrrolyl)-benzyl]-2,3,4,5-tetrahydro-2-oxo-1H-1-benzazepin-3(R)-yl]-3-methylbutanamide
41. 2-Amino-N-[1-[4-(4-bromo-2-[1H-tetrazol-5-yl]-1-pyrrolyl)-benzyl]-2,3,4,5-tetrahydro-2-oxo-1H-1-benzazepin-3(R)-yl]-2-methylpropanamide
42. 3-Amino-N-[5-[4-(4-bromo-2-[1H-tetrazol-5-yl]-1-pyrrolyl)-benzyl]-2,3,4,5-tetrahydro-4-oxo-5H-1,5-benzothiazepin-3(S)-yl]-3-methylbutanamide The compounds of the instant invention all have at least one asymmetric center as noted by the asterisk in structural Formulae I and Ia. Additional asymmetric centers may be present on the molecule depending upon the nature of the various substituents on the molecule. Each such asymmetric center will produce two optical isomers and it is intended that all such optical isomers, as separated, pure or partially purified optical isomers or racemic mixtures thereof, be included within the ambit of the instant invention. In the case of the asymmetric center represented by the asterisk in Formula I, it has been found that the compound in which the 3-amino substituent is above the plane of the structure, as seen in Formula Ia, is more active and thus more preferred over the compound in which the 3-amino substituent is below the plane of the structure. This center will be designated according to the R/S rules as either R or S depending upon the value of X.

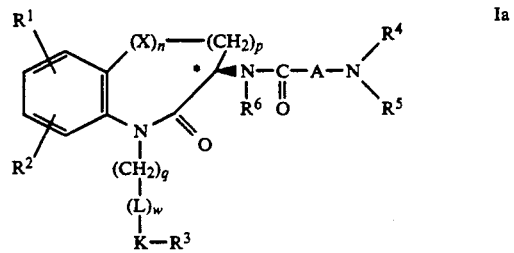

Ia

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic and the like. In addition, certain compounds containing an acidic function such as a carboxy or tetrazole, can be isolated in the form of their inorganic salt in which the counterion can be selected from sodium, potassium, lithium, calcium, magnesium and the like, as well as from organic bases.

The compounds (I) of the present invention are prepared from aminolactam intermediates such as those of formula II. The preparation of these intermediates is described in the following reaction Schemes.

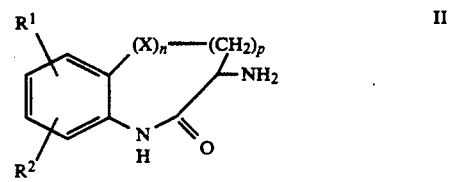

II

Benzo-fused lactams 3 wherein the lactam is a seven-membered ring are conveniently prepared from substituted tetralones 2 using known procedures. The substituted tetralones are, in some cases, commercially available or are prepared from a suitably substituted derivative of 4-phenylbutyric acid 1. Cyclization of 1 can be achieved by a number of methods well known in the literature including treatment with polyphosphoric acid at elevated temperatures as shown in Scheme 1.

SCHEME 1

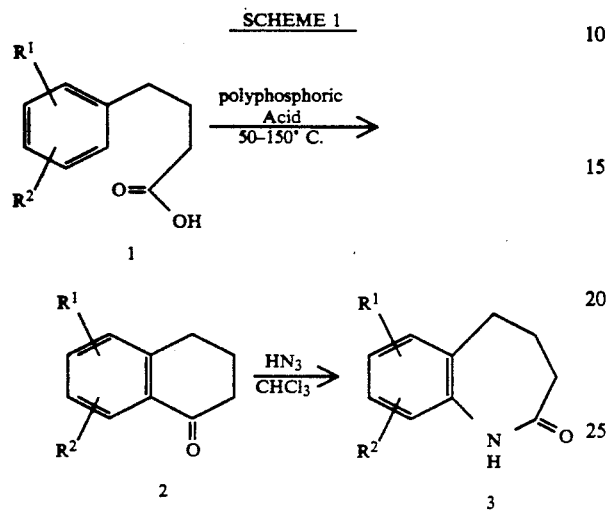

Conversion of substituted tetralones 2 to benzolactams 3 can be achieved by a number of methods familiar to those skilled in the art. A suitable method involves the use of hydrazoic acid (Schmidt reaction) to from the substituted benzolactam 3.

Benzo-fused lactams wherein the lactam is an eight-membered ring (6) are prepared as described by D. H. Jones, et al, J. Chem. Soc. C, 2176-2181 (1969) by an analogous series of transformations starting from a substituted derivative of 5-phenylpentanoic acid 4 as shown in Scheme 2.

SCHEME 2

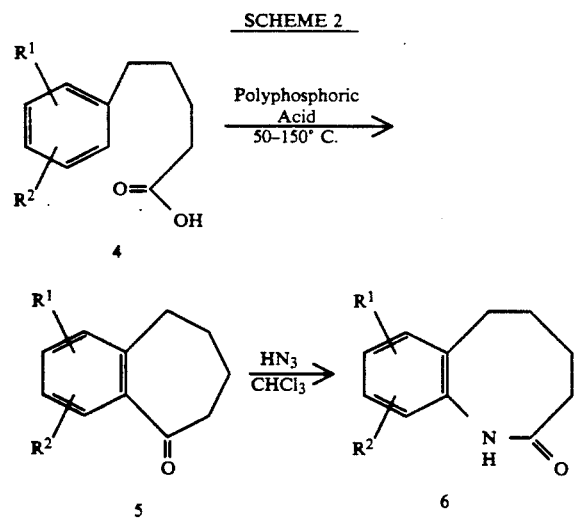

As shown in Scheme 3,3-aminobenzolactam analogs wherein the lactam is a six-membered ring (11) are prepared from a substituted derivative of 2-nitrobenzyl chloride (or bromide) 7 by the method of A. L. Davis, et al, Arch. Biochem. Biophys, 102, 48-51 (1963) and references cited therein.

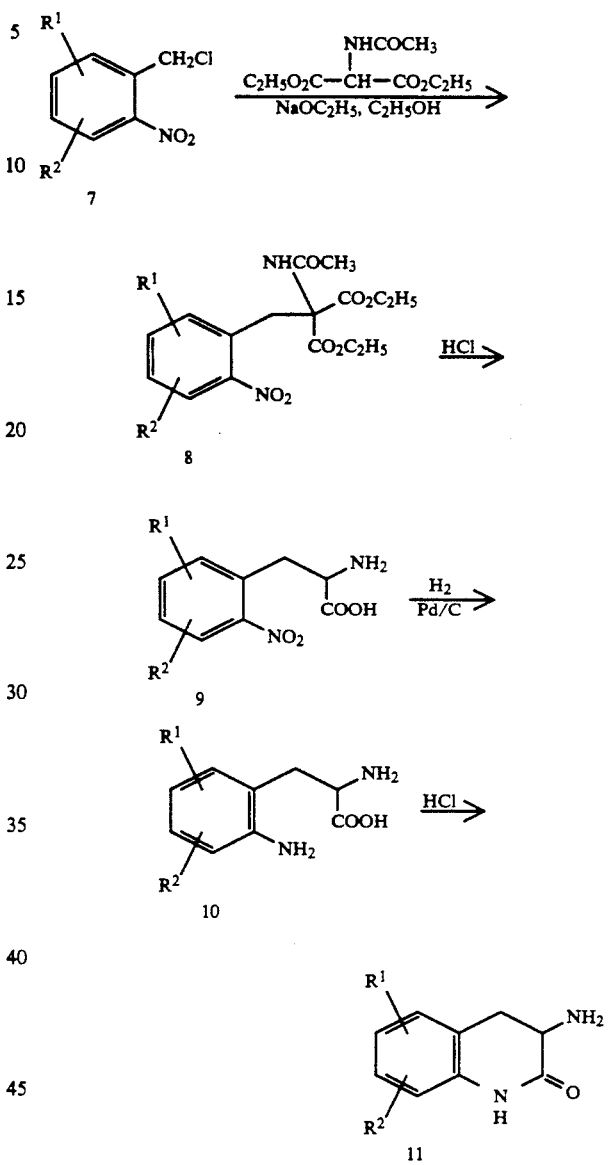

Conversion of substituted benzo-fused lactams to the requisite 3-amino derivatives can be achieved by a number of methods familiar to those skilled in the art, including those described by Watthey, et al, J. Med. Chem., 28, 1511-1516 (1985) and references cited therein. One common route proceeds via the intermediacy of a 3-halo (chloro, bromo or iodo) intermediate which is subsequently displaced by a nitrogen nucleophile, typically azide. A useful method of forming the 3-iodobenzolactam intermediate 12 involves treating the benzolactam with two equivalents each of iodotrimethysilane and iodine at low temperature, as illustrated in Scheme 4 for the seven-membered ring analog 3.

SCHEME 4

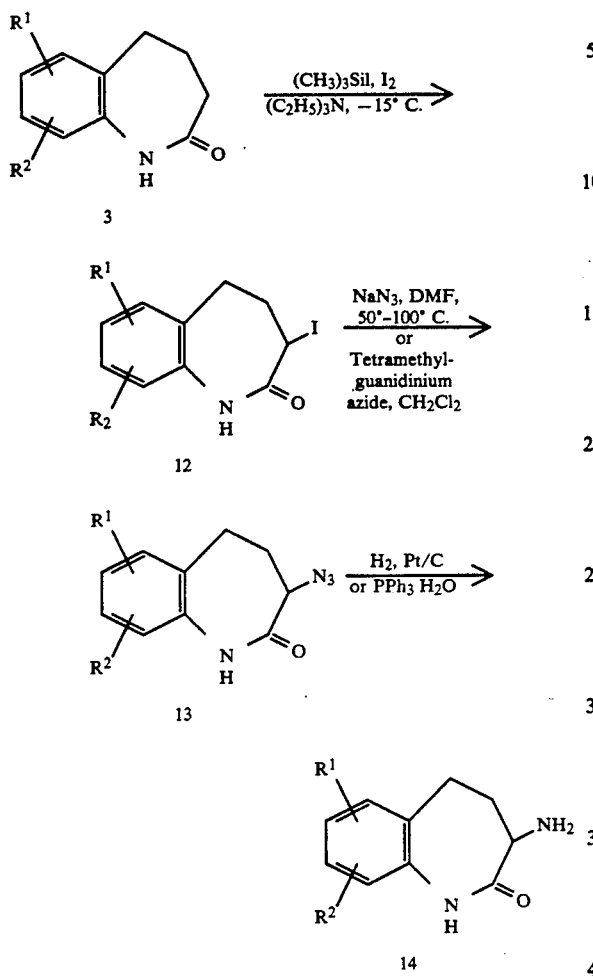

SCHEME 5

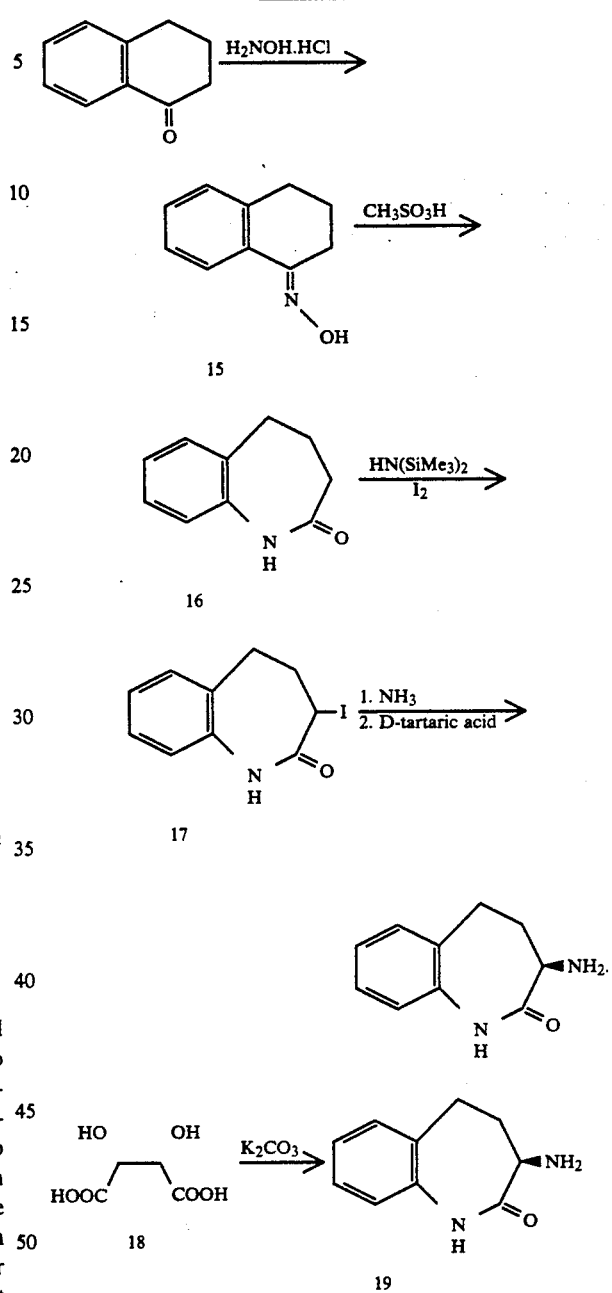

Elaboration of the iodo-benzolactams to the desired aminolactam intermediates II is achieved by a two-step procedure illustrated in Scheme 4. Typically, iodo-benzolactams 12 are treated with sodium azide in N,N-dimethylformamide at 50°–100° C. to give the 3-azido derivatives 13. Alternatively, tetramethylguanidinium azide in a solvent such as methylene chloride can be employed to achieve similar results. Hydrogenation with a metal catalyst, such as platinum on carbon, or alternatively, treatment with triphenylphosphine in wet toluene, results in formation of the amine derivative 14. Formation of the analogous derivatives of the eight-membered benzolactams is also achieved by the routes shown in Scheme 4.

Chiral aminobenzolactams are obtained by resolution of the racemates by classical methods familiar to those skilled in the art. For example, resolution can be achieved by formation of diastereomeric salts of the racemic amines with optically active acids such as D- and L-tartaric acid. Determination of absolute stereochemistry can be achieved in a number of ways including X-ray analysis of a suitable crystalline derivative.

A useful preparation of the chiral intermediate 19 is shown in Scheme 5.

Conversion of 1-tetralone to the seven-membered benzolactam 16 is achieved by Beckman rearrangement of the intermediate oxime 15. Treatment of 16 with iodine and hexamethyldisilazane gives the 3-iodo derivative 17 which is sequentially treated with ammonia and D-tartaric acid to give the diastereomeric D-tartrate salt 18 after recrystallization. Liberation of the free amine 19 is achieved by neutralization of the D-tartrate salt with potassium carbonate followed by extractive isolation.

Intermediates of Formula II wherein X is a sulfur atom are prepared by methods described in the literature and known to those skilled in the art. As illustrated in Scheme 6, the seven-membered ring analog 27 is prepared from a protected derivative of cysteine 21 by the method of Slade, et al, J. Med. Chem., 28, 1517–1521 (1985) and references cited therein (CBz=benzyloxycarbonyl).

SCHEME 6

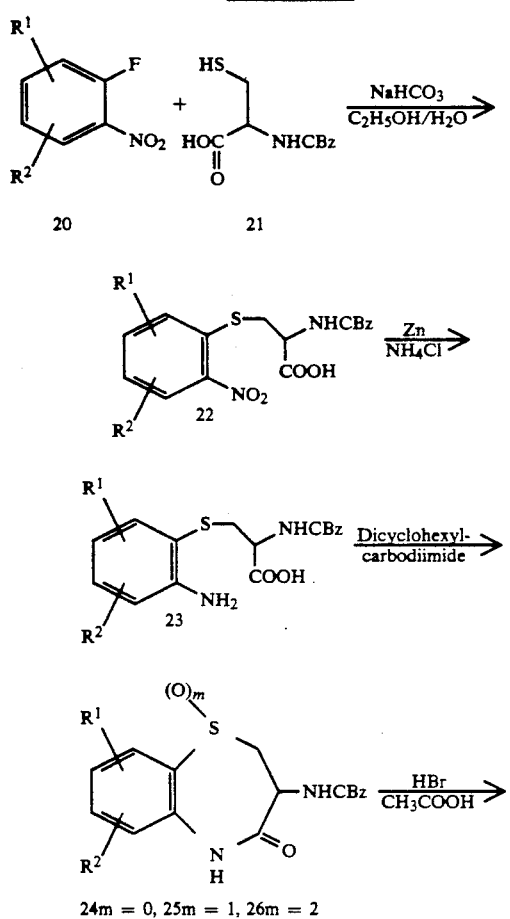

Sulfoxide and sulfone intermediates 28 and 29 are prepared by oxidation of 24 with various oxidants such as periodate or meta-chloro-perbenzoic acid. Eight-membered ring intermediates of Formula II wherein X is sulfur can be prepared by an analogous route starting from derivatives of homo-cysteine.

Intermediates of Formula II wherein X is an oxygen atom are prepared by methods described in the literature and known to those skilled in the art. For example, the seven-membered ring analog 31 can be prepared from a substituted derivative of 3-(2-nitro-phenoxy)-propanoic acid 30 by the method of J. Ott, Arch. Pharm. (Weinheim, Ger.), 323(9), 601–603 (1990).

SCHEME 7

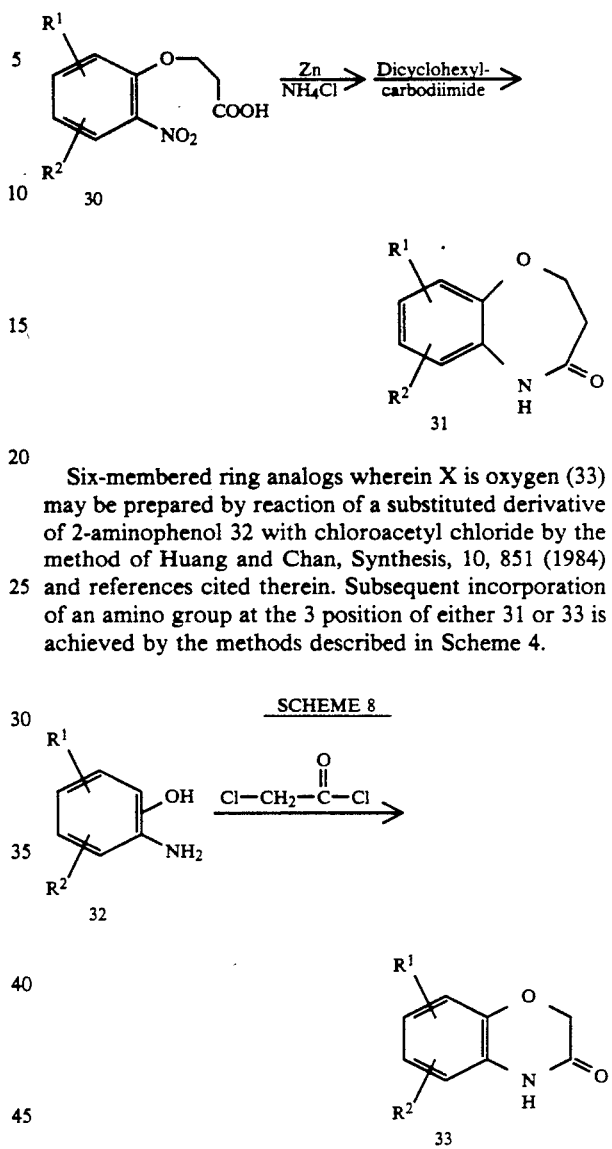

Six-membered ring analogs wherein X is oxygen (33) may be prepared by reaction of a substituted derivative of 2-aminophenol 32 with chloroacetyl chloride by the method of Huang and Chan, Synthesis, 10, 851 (1984) and references cited therein. Subsequent incorporation of an amino group at the 3 position of either 31 or 33 is achieved by the methods described in Scheme 4.

SCHEME 8

Seven-membered ring analogs of Formula II wherein X is C=O can be prepared from derivatives of tryptophan as described in the Australian Journal of Chemistry, 33, 633–640 (1980). Seven-membered ring analogs of Formula II wherein X is CH=CH can be prepared from the aforementioned analogs wherein X is C=O. Treatment of 34 with chemical reducing agents such as sodium borohydride in a polar solvent such as methanol or ethanol results in reduction to give the secondary alcohol derivative 35 (X=CHOH).

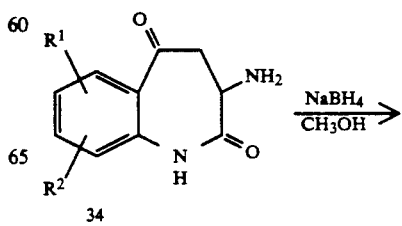

19
-continued

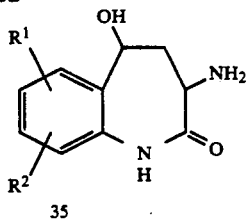
35

Dehydration of 35 can be achieved by several methods described in the literature and familiar to those skilled in the art. For example, treatment of 35 in an inert solvent, such as benzene, with a strong acid such as p-toluenesulfonic acid, will result in dehydration to the unsatured analog 36.

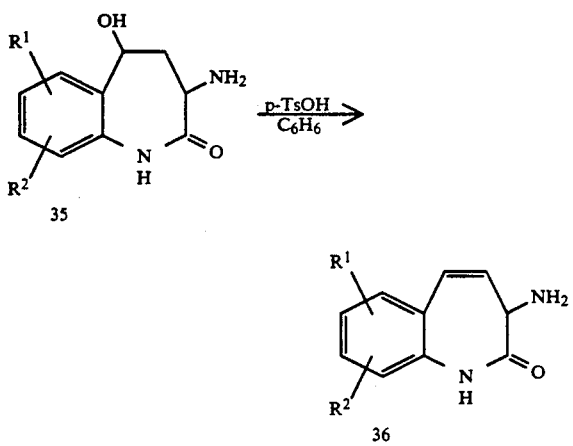

Intermediates of formula II can be further elaborated to new intermediates (formula III) which are substituted on the amino group (Scheme 9). Reductive alkylation of II with an aldehyde is carried out under conditions known in the art; for example, by catalytic hydrogenation with hydrogen in the presence of platinum, palladium or nickel catalysts or with chemical reducing agents such as sodium cyanoborohydride in an inert solvent such as methanol or ethanol.

SCHEME 9

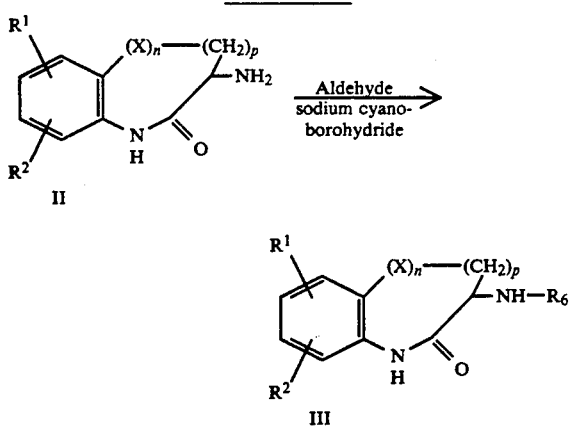

Attachment of the amino acid sidechain to intermediates of formula III is accomplished by the route shown in Scheme 10. Coupling is conveniently carried out by the use of an appropriately protected amino acid derivative, such as that illustrated by formula IV, and a coupling reagent such as benzotriazol-1-yloxytris(dimethylamino)phosphonium hexafluorophosphate ("BOP'-')in an inert solvent such as methylene chloride. Separation of unwanted side products, and purification of intermediates is achieved by chromatography on silica gel, employing flash chromatography (W. C. Still, M. Kahn and A. Mitra, J. Org. Chem., 43, 2923 (1978) or by medium pressure liquid chromatography.

SCHEME 10

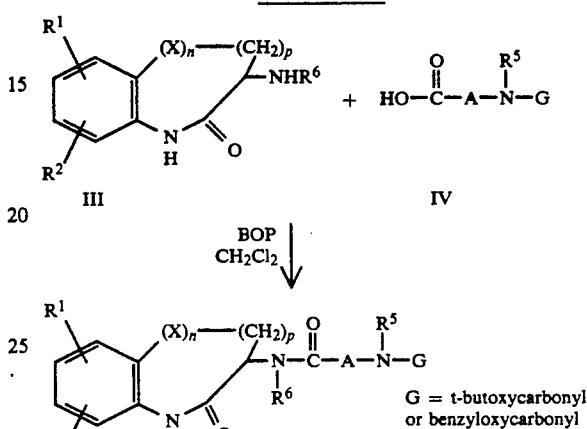

The protected amino acid derivatives IV are, in many cases, commercially available in T-butoxycarbonyl (BOC) or benzyloxycarbonyl (CBz) forms. A useful method to prepare the preferred sidechain 41 is shown in Scheme 11.

SCHEME 11

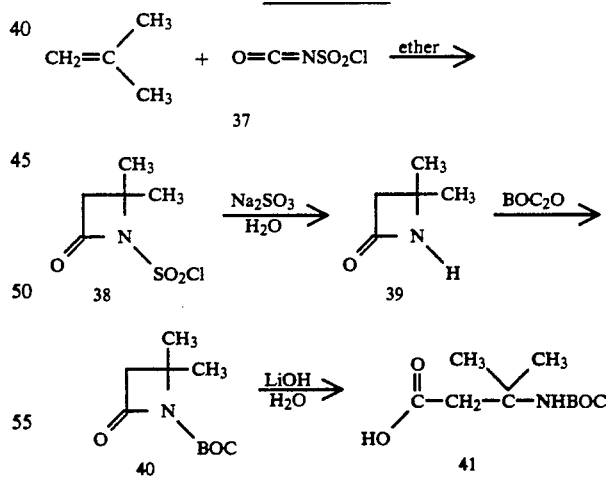

Reaction of isobutylene with N-chlorosulfonylisocyanate 37 in diethyl ether gives the azetidinone derivative 38. Removal of the chlorosulfonyl group with aqueous sodium sulfite followed by reaction with di-t-butyl-dicarbonate gives the BOC-protected intermediate 40. Alkaline hydrolysis gives the protected amino acid derivative 41 in good overall yield.

Intermediates of formula VII can be prepared as shown in Scheme 12 by treatment of the desired lactam intermediate V with an alkylating agent VI, wherein Y is a good leaving group such as Cl, Br, I, O-methanesulfonyl or O-(p-toluenesulfonyl). Alkylation of intermediates of formula V is conveniently carried out in anhydrous dimethyl formamide (DMF) in the presence of bases such as sodium hydride or potassium t-butoxide for a period of 0.5 to 24 hours at temperatures of 20°-100° C. Substituents on the alkylating agent VI may need to be protected during alkylation. A description of such protecting groups may be found in: *Protective Groups in Organic Synthesis*, T. W. Greene, John Wiley and Sons, New York, 1981.

SCHEME 12

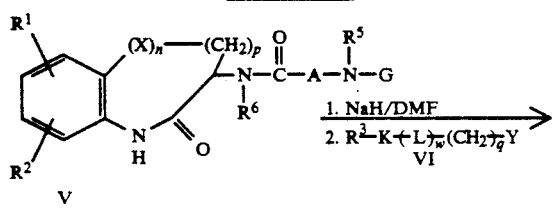

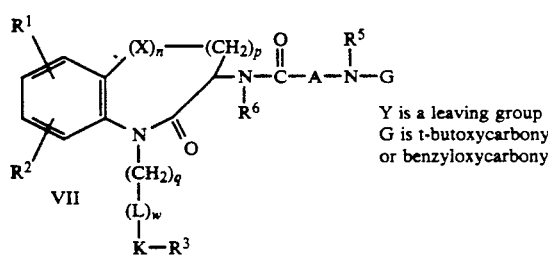

Y is a leaving group
G is t-butoxycarbonyl or benzyloxycarbonyl

Alkylating agents VI containing the appropriate alicycles, aryl groups, or heterocycles in the format as Y—(CH$_2$)$_q$—(L)$_w$—K—R$^3$, where Y is a leaving group, are prepared by methods described hereinafter. Reactions of VI with compounds of formula V are then carried out according to the conditions described in Scheme 12.

SCHEME 13

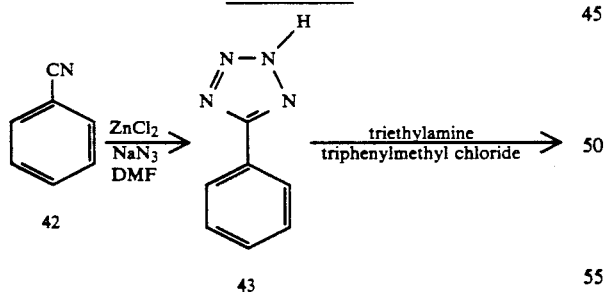

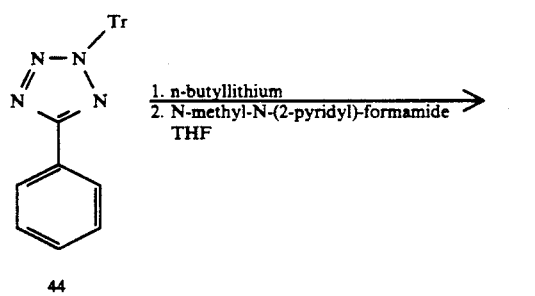

-continued
SCHEME 13

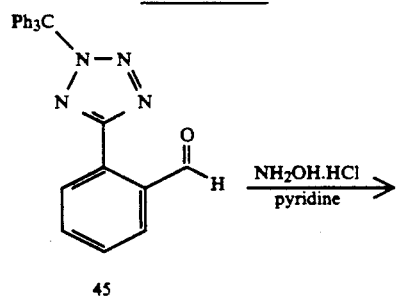

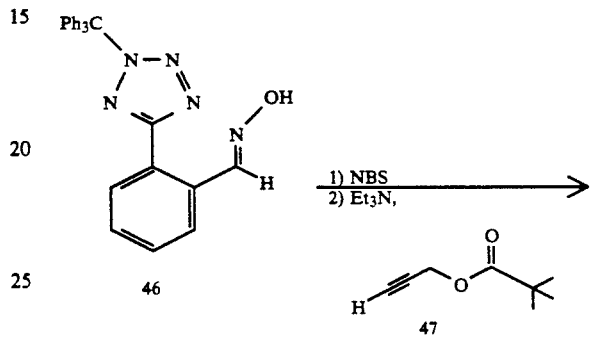

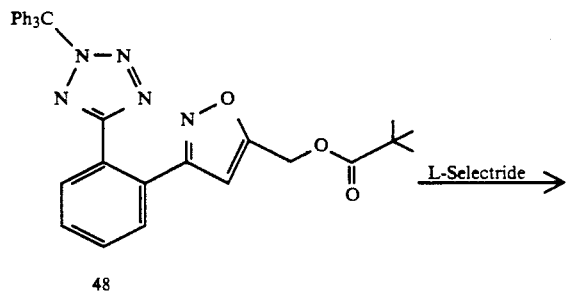

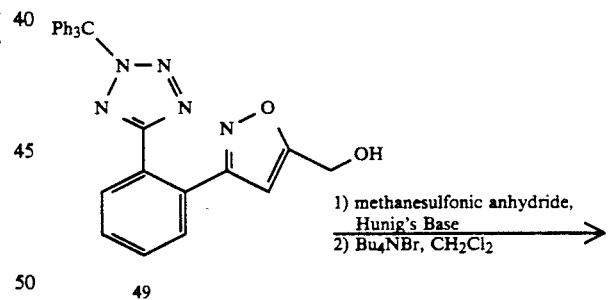

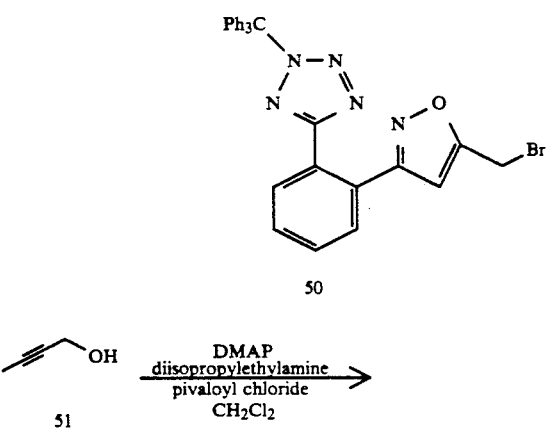

-continued
SCHEME 13

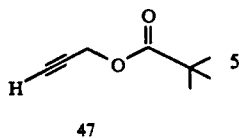

Treatment of benzonitrile with zinc chloride and sodium azide in DMF at 115° C. gives compound 43, which can be tritylated with triethylamine and triphenylmethyl chloride at room temperature. The trityl-protected phenyltetrazole 44 is ortho-lithiated by n-butyllithium, and the subsequent trapping with N-methyl-N-(2-pyridyl)-formamide gives aldehyde 45. Reaction of 45 with the hydrochloride salt of hydroxylamine provides the oxime intermediate 46, which is reacted with N-bromosuccinimide, triethylamine, and the pivaloyl-protected propargyl alcohol 47 to give the isoxazol 48. Reduction of 48 with L-Selectride leads to 49, which is then converted to the corresponding bromide 50 by treatment with tetrabutylammonium bromide, diisopropylethylamine, and methanesulfonic anhydride, via the in situ generation of the corresponding mesylate.

SCHEME 14

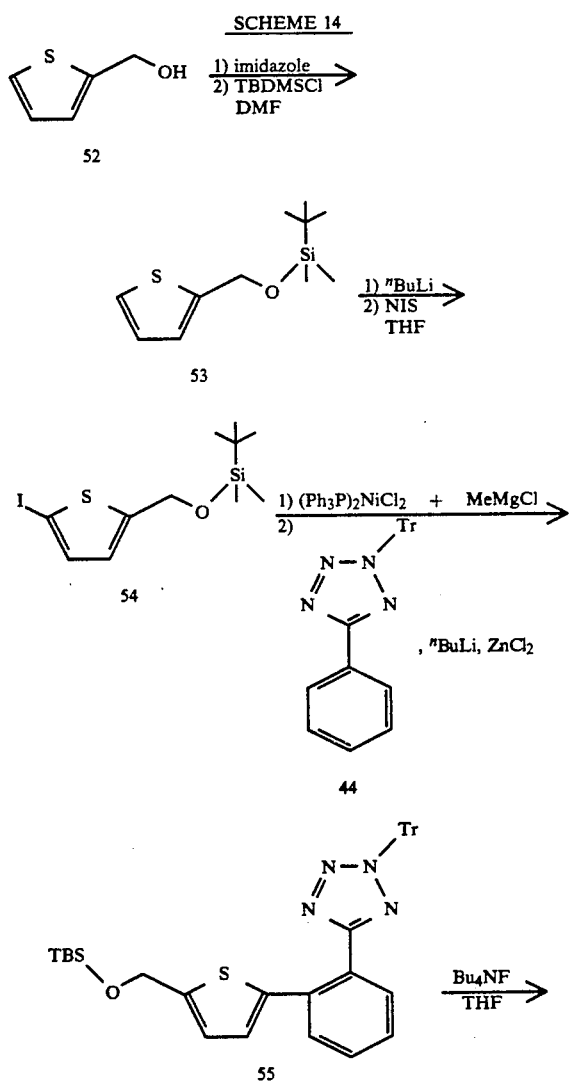

-continued
SCHEME 14

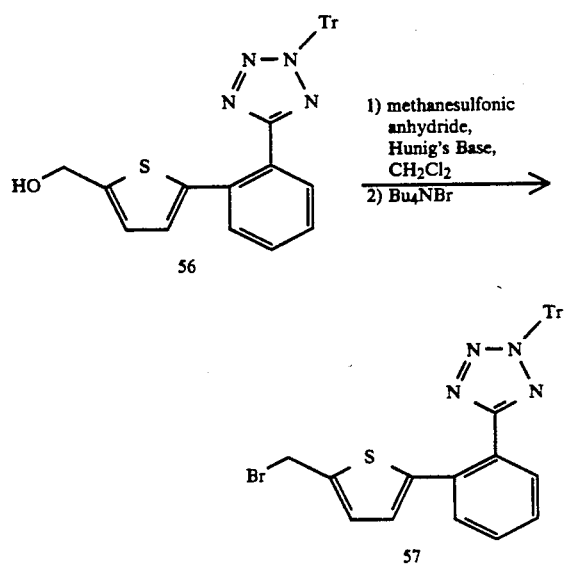

The commercial 2-thiophene methanol 52 is protected as a t-butyldimethylsilyl ether under standard conditions. Treatment of 53 with 1 equivalent of n-butyllithium and N-iodosuccinimide gives the 5-iodo compound 54, which is then coupled to 44 with bis(triphenylphosphine)nickel chloride as the catalyst. The silyl ether is cleaved by tetrabutylammonium fluoride to give the alcohol 56, which is converted to the corresponding bromide 57 under the same conditions as described in Scheme 13.

SCHEME 15

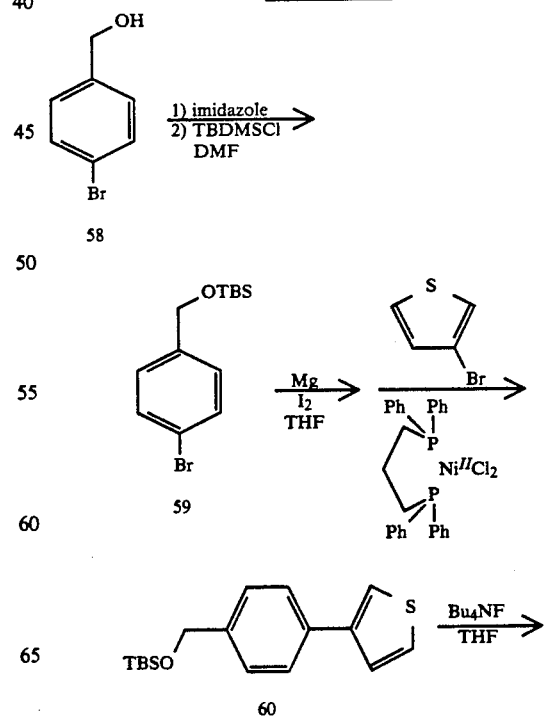

-continued
SCHEME 15

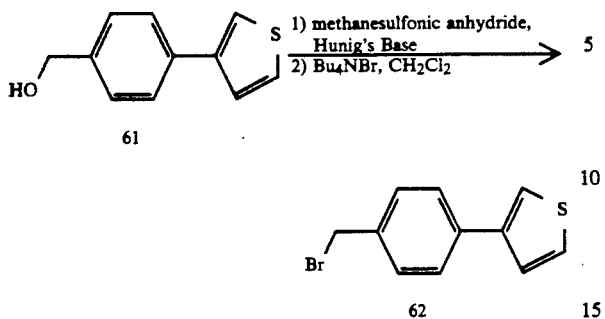

The treatment of 4-bromobenzyl alcohol with imidazole and t-butyldimethylsilyl chloride in DMF gives 59, from which a Grignard reagent is made and coupled to 3-bromothiophene with [1,3-bis(diphenylphosphino)-propane]nickel chloride as the catalyst. The silyl ether is cleaved by fluoride, and the alcohol 61 is subsequently converted to the corresponding bromide 62 under the same conditions as previously described.

SCHEME 16

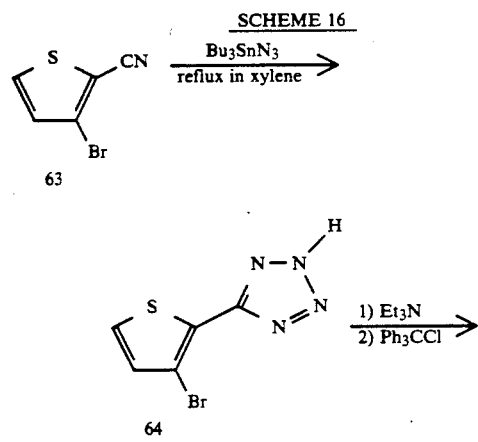

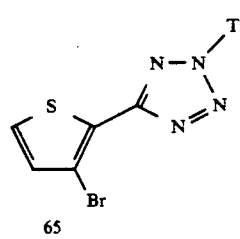

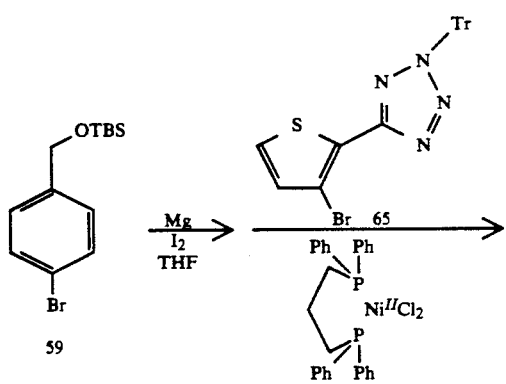

-continued
SCHEME 16

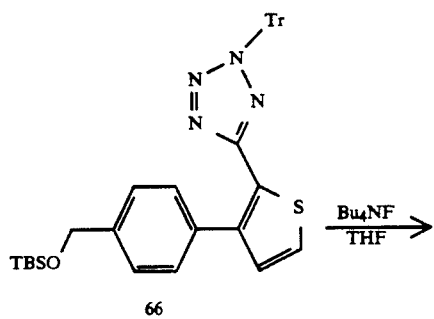

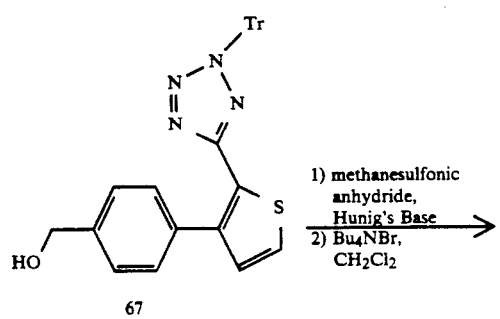

Treatment of 3-bromo-2-cyanothiophene 63 with tributyltin azide in refluxing xylene gives the tetrazole compound 64, which is then protected with triethylamine and trityl chloride to provide compound 65. The TBS-protected 4-bromobenzyl alcohol 59 from Scheme 15 is converted to the Grignard and coupled to 65 to give 66, which is subsequently deprotected and converted to the corresponding bromide 68.

SCHEME 17

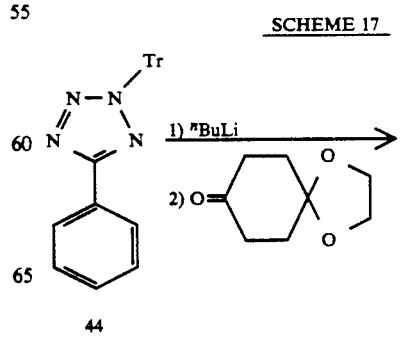

-continued
SCHEME 17

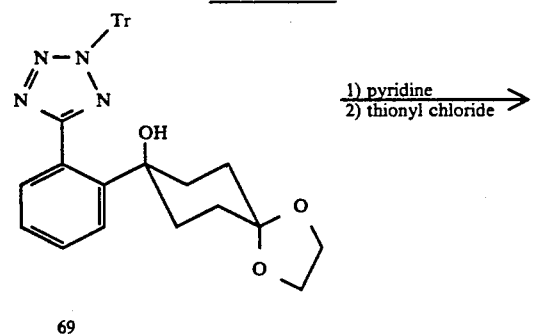

69

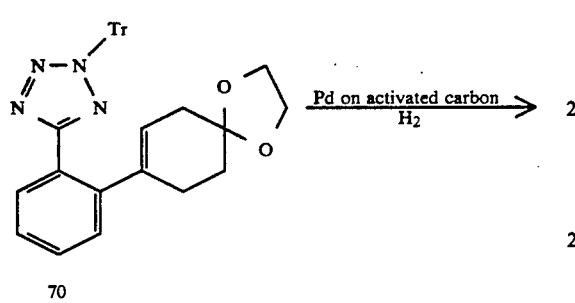

70

5N HCl:THF
2:1 ⟶   Et₃N / TrCl ⟶

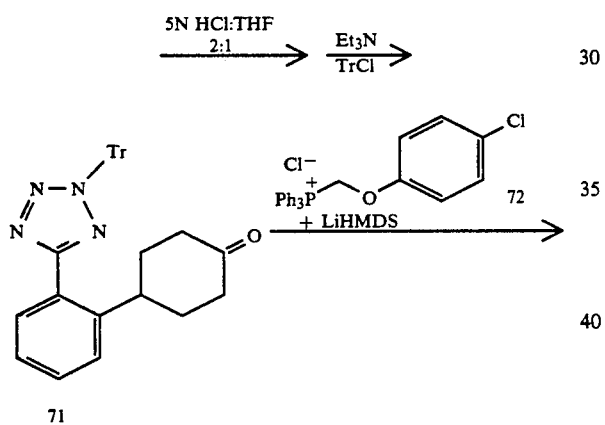

71

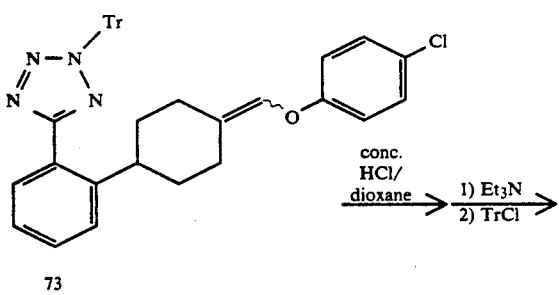

73

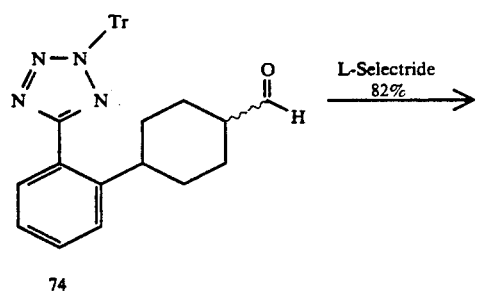

74

-continued
SCHEME 17

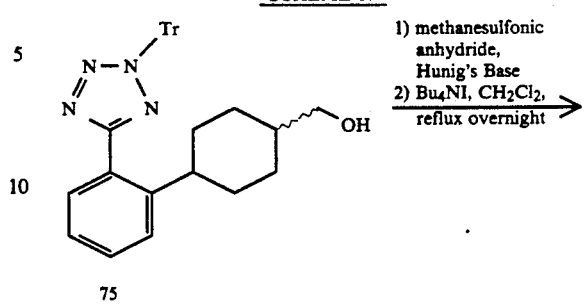

75

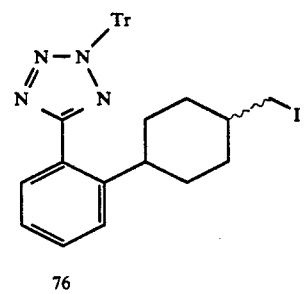

76

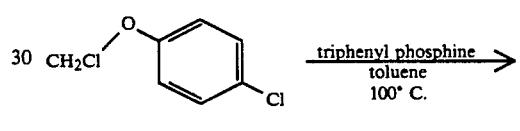

77

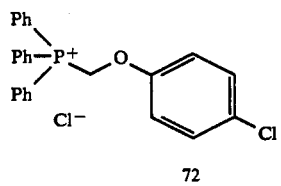

72

The trityl-protected phenyltetrazole 44 is ortho-lithiated, and the resultant lithium anion is reacted with 1,4-cyclohexanedionemono-ethylene ketal to give the tertiary alcohol 69, which is dehydrated with pyridine and thionyl chloride to give 70. Hydrogenation of 70 with 5% palladium on carbon and the subsequent deprotection of the ketal, during which the trityl group is lost and is put back on the molecule under the standard condition, give compound 71. The Wittig reaction of 71 with the phosphonium salt 72, with lithium hexamethyldisilazide as the base, gives the vinyl ether 73. Concentrated hydrochloric acid cleaves the vinyl ether as well as the trityl group, and the latter is then put back on the molecule. Reduction of aldehyde 74 with L-Selectride gives alcohol 75, which is converted to the corresponding iodide 76 by treating with diisopropylethylamine and methanesulfonic anhydride to form the mesylate in situ and the subsequent treatment of excess tetrabutylammonium iodide in refluxing methylene chloride.

SCHEME 18

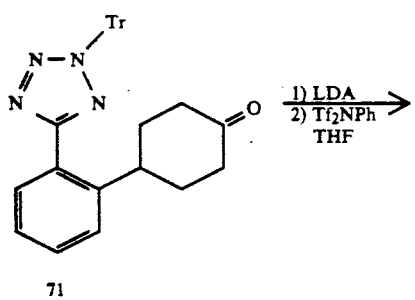

71

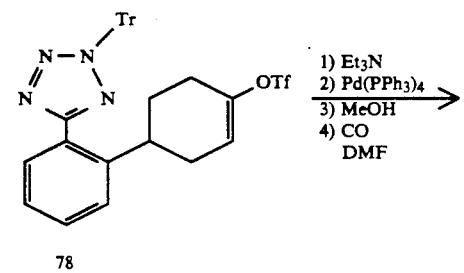

78

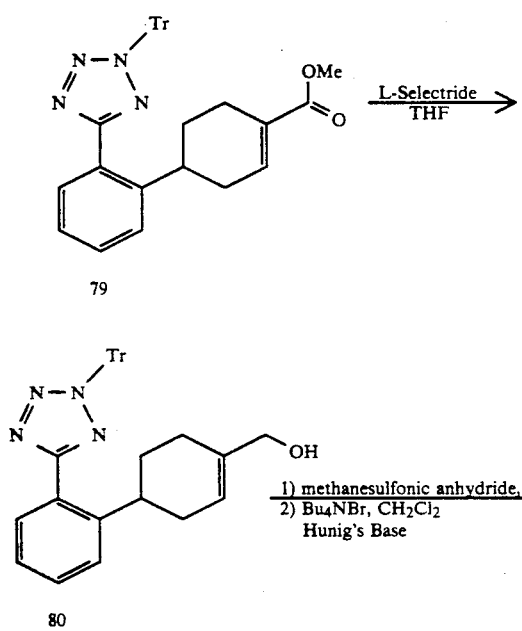

79

80

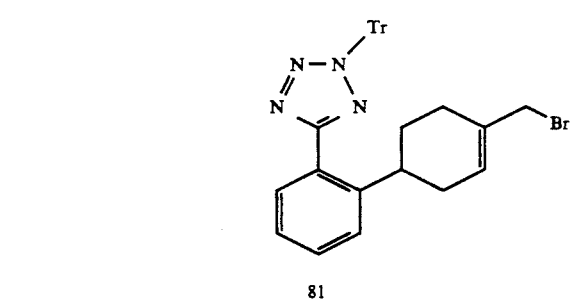

81

The ketone 71 from Scheme 17 is enolized by lithium diisopropylamide, and the subsequent trapping of the lithium enolate with N-phenyltrifluoromethane sulfonimide gives the vinyl triflate 78. Carbonylation of 78 with palladium (0), carbon monoxide, and excess methanol provides the methyl ester 79, which is then reduced by L-Selectride to give alcohol 80. The alcohol is converted to the corresponding bromide 81 under the same conditions as described before.

SCHEME 19

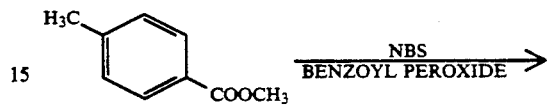

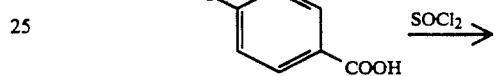

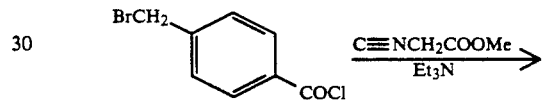

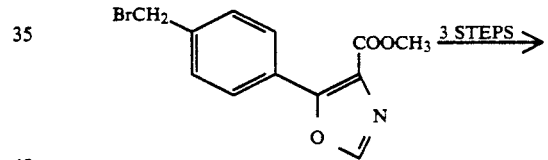

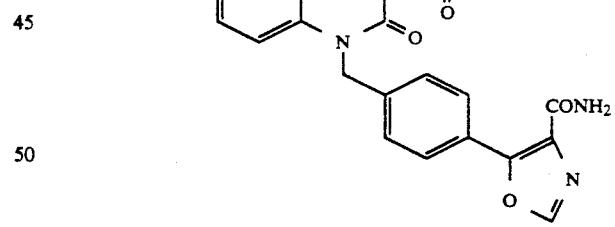

4-(4-Carbomethoxy-5-oxazolyl)-benzyl bromide is prepared as described in EP 0 485 929 A1 example 6 a) to d). To this end 4-methylbenzoic acid methyl ester is reacted with N-bromosuccinimide in chlorobenzene with a catalytic amount of benzoyl peroxide to form 4-bromomethyl benzoic acid methyl ester. This is hydrolysed to the acid with 48% aqueous hydrobromic acid, and the acid is reacted with thionyl chloride to give the acid chloride. This is stirred in tetrahydrofuran solution with triethyl amine and methyl isocyanoacetate to give 4-(4-carboxymethoxy-5-oxazolyl)-benzyl bromide.

SCHEME 20

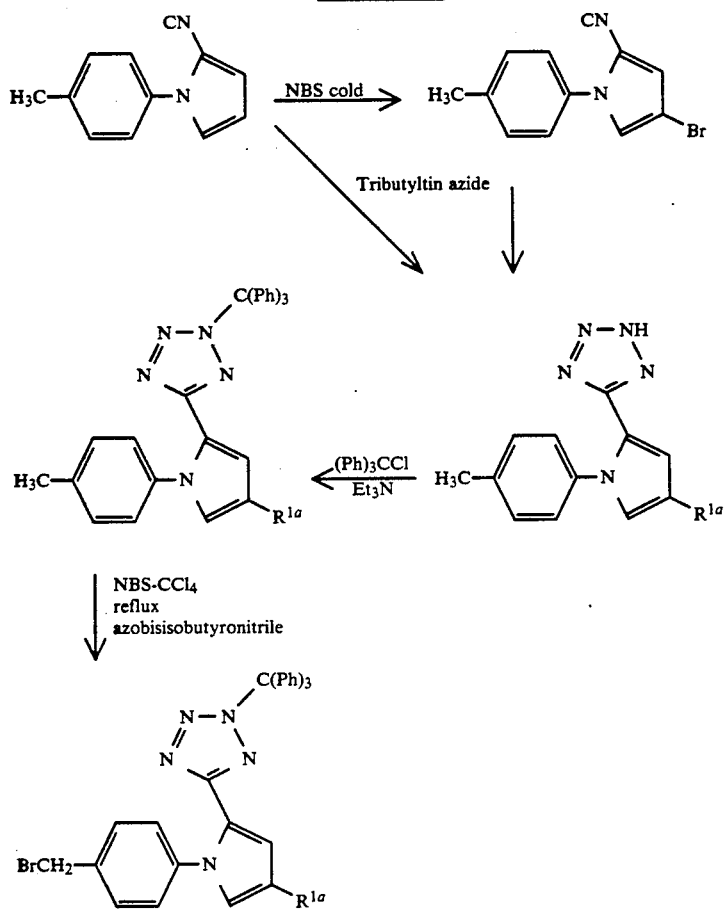

4-(2-(2H-2-trityltetrazol-5-yl)-1-pyrrolyl)-benzyl bromide is prepared as described in EP 0 480 204 A1 preparation 1 and 8, and as described in EXAMPLE 10. To this end 1-(4-methylphenyl)-2-cyanopyrrole is reacted with tributyltin azide to give 4-(2-(1H-tetrazol-5-yl)-1-pyrrolyl)-methylbenzene, which is protected by reaction with triphenylmethyl chloride. The benzylic methyl group of (2-(2H-2-trityltetrazol-5-yl)-1-pyrrolyl)-methylbenzene is then converted to the benzyl bromide with N-bromosuccinimide. An analog with a bromo substituent in the pyrrole ring is prepared from the same starting material 1-(4-methylphenyl)-2-cyanopyrrole by reaction with N-bromosuccinimide at room temperature to give 1-(4-methylphenyl)-4-bromo-2-cyanopyrrole. This is further reacted by analogy to the unsubstituted compound.

Compounds of formula I wherein $R^3$ is a tetrazole (75) are prepared as described in Scheme 21 by alkylation of V with a suitably substituted alkylating agent 73 containing a nitrile as tetrazole precursor. Elaboration to the desired tetrazole product 75 is carried out by treatment with trimethyltin azide in refluxing toluene.

SCHEME 21

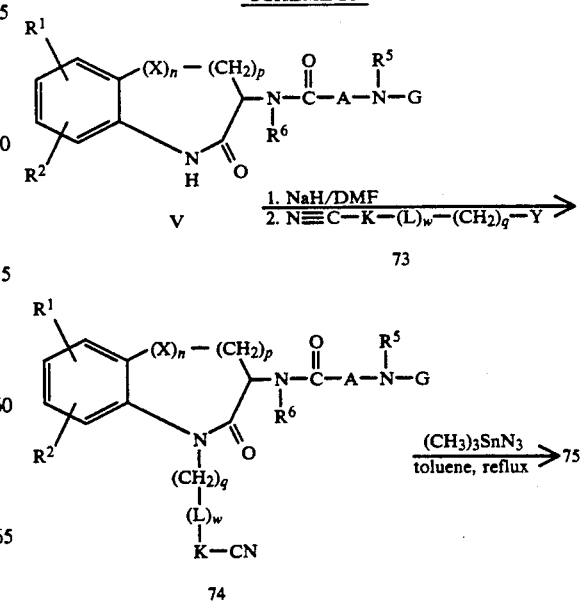

-continued
SCHEME 21

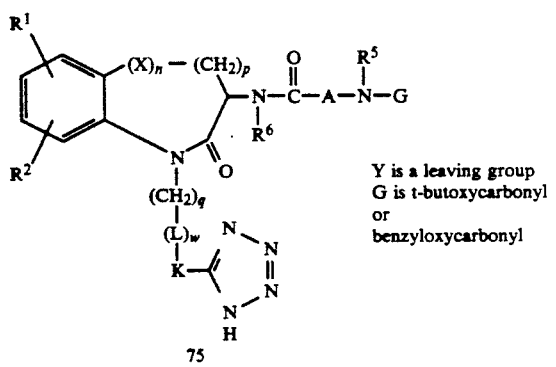

Y is a leaving group
G is t-butoxycarbonyl or benzyloxycarbonyl

Compounds of Formula I wherein $R^3$ is taken as $R^4R^5NCO$ can be prepared by several methods. For example, as shown in Scheme 22, compound 81 wherein $R^4$ and $R^5$ are both hydrogen is conveniently prepared by hydrolysis of a nitrile precursor 74.

SCHEME 22

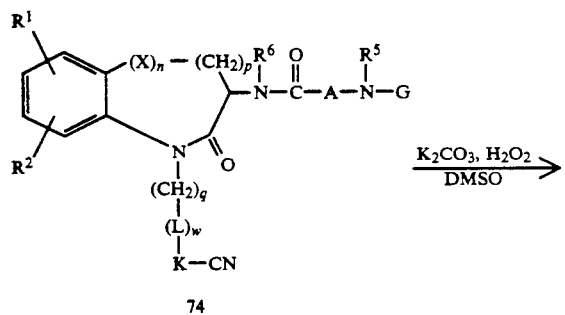

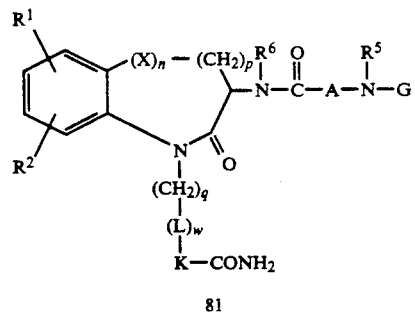

Thus, treatment of the nitrile 74 with hydrogen peroxide and a strong base, such as potassium carbonate, in a polar solvent, such as dimethylsulfoxide at temperatures of 25° C. to 150° C. results in formation of the amide derivative 81.

Compounds of Formula I wherein $R^3$ is taken as $R^4R^5NCO$ and $R^4$ and/or $R^5$ are not hydrogen (83) are prepared from the corresponding carboxylic acid derivatives 82 as shown in Scheme 23.

SCHEME 23

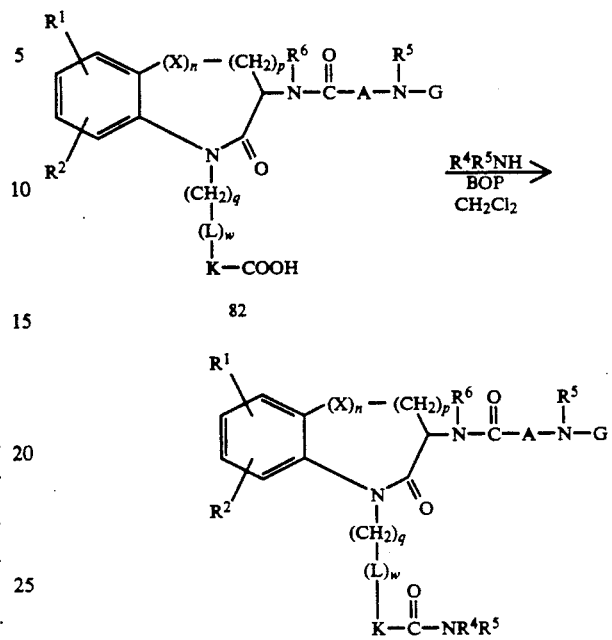

Coupling of the carboxylic acid derivative 82 with $R^4R^5NH$ is conveniently carried out by the use of a coupling reagent such as benzotriazol-1-yloxytris(dimethylamino)phosphonium hexafluorophosphate ("BOP") in an inert solvent such as methylene chloride.

Compounds of formula I where $R^3$ is a carbamate, semicarbazide or urea derivative, wherein this functionality is attached to the phenyl ring by a nitrogen atom are prepared from intermediates 85, obtained by alkylation with a derivative of formula VI wherein $R^3$ is a nitro group 84 as shown in Scheme 24.

SCHEME 24

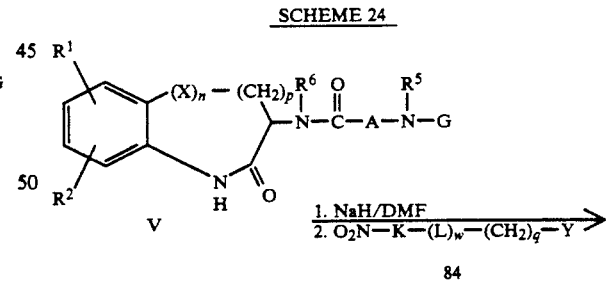

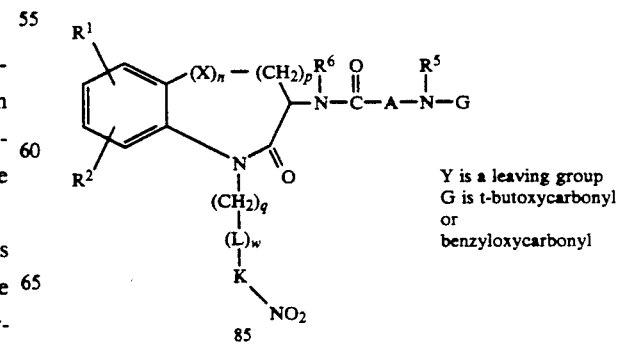

Y is a leaving group
G is t-butoxycarbonyl or benzyloxycarbonyl

As shown in Scheme 25, reduction of the nitro group of 85 is achieved by hydrogenation in the presence of a metal catalyst, such as palladium on carbon, in a protic solvent such as methanol or ethanol. It may be appreciated by one skilled in the art that for certain compounds where catalytic hydrogenation is incompatible with existing functionality, alternative methods of reduction are indicated, such as chemical reduction with stannous chloride under acidic conditions. It should also be noted that the protecting group G in intermediate 85 must be compatible with the experimental conditions anticipated for reduction. For example, intermediate 85 wherein G is t-butoxycarbonyl (BOC) are stable to the conditions of catalytic reduction employed in the conversion to 86. Intermediates 86 may also be further elaborated to new intermediates 87 by reductive alkylation with an aldehyde by the aforementioned procedures.

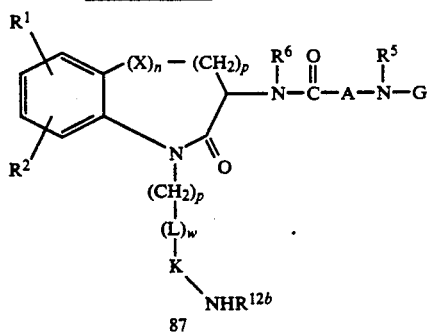

Elaboration of 87 to carbamate compounds 88 is achieved by reaction with the appropriate chloroformate reagent in pyridine or in methylene chloride with triethylamine as shown in Scheme 26.

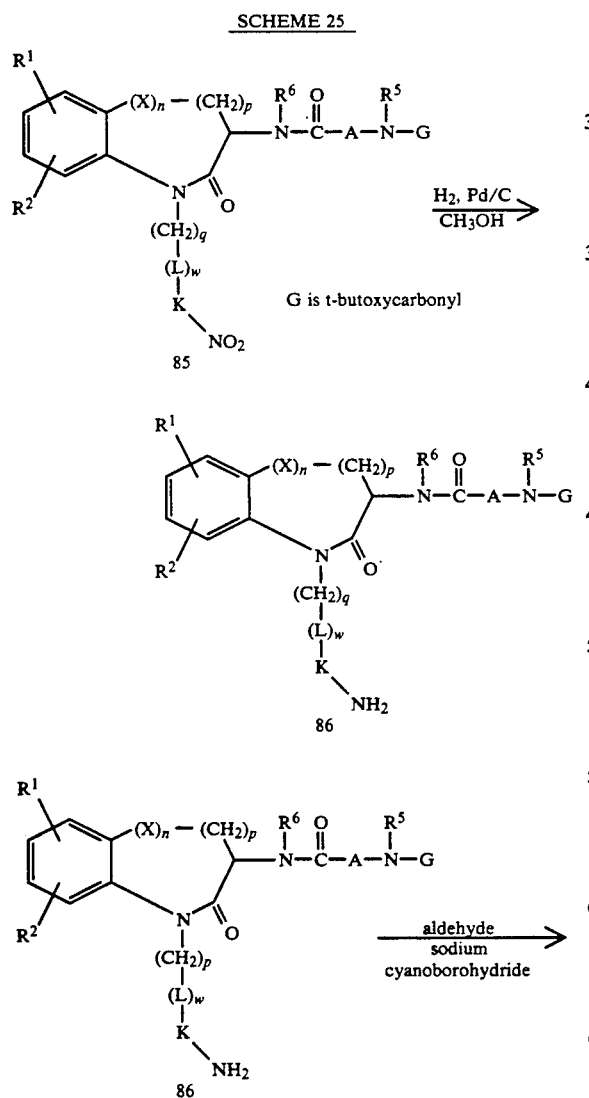

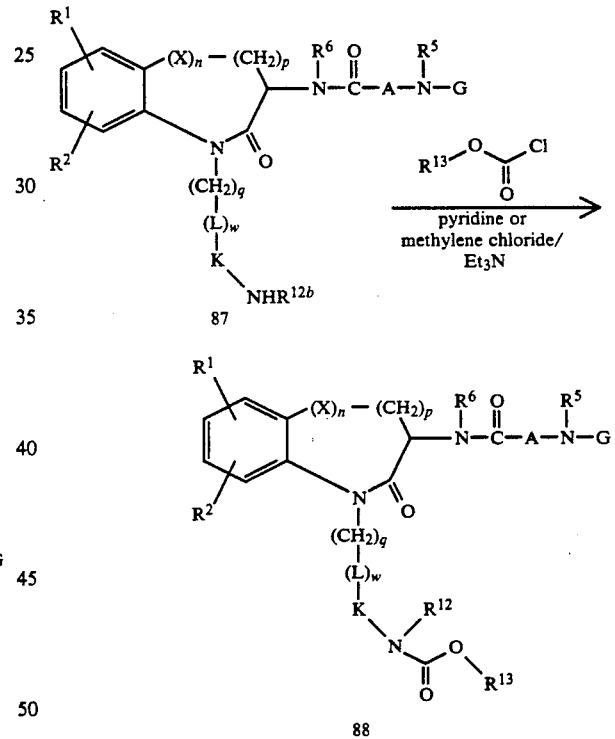

Transformation of amine intermediate 87 to urea derivatives is accomplished in several ways. Terminally disubstituted compounds 89 can be obtained directly by reaction of 87 with a disubstituted carbamoyl chloride in an inert solvent such as methylene chloride in the presence of triethylamine or 4-dimethylaminopyridine. In addition, monosubstituted compounds 90 wherein either $R^{4b}$ or $R^{12a}$ is hydrogen are obtained from 87 by reaction with an isocyanate as shown in Scheme 27.

Alternatively, amine 87 is converted to an isocyanate 91 by treatment with phosgene or an equivalent reagent such as bis(trichloromethyl)carbonate (triphosgene) as indicated in Scheme 28. Subsequent reaction of 91 with primary or secondary amines in an inert solvent such as methylene chloride gives the corresponding urea derivates 92 in good yield. Isocyanate 91 is also converted to substituted semicarbazides 93 or hydroxy- or alkoxyureas 94 by reaction with substituted hydrazines or hydroxy- or alkoxylamines, respectively.
SCHEME 27
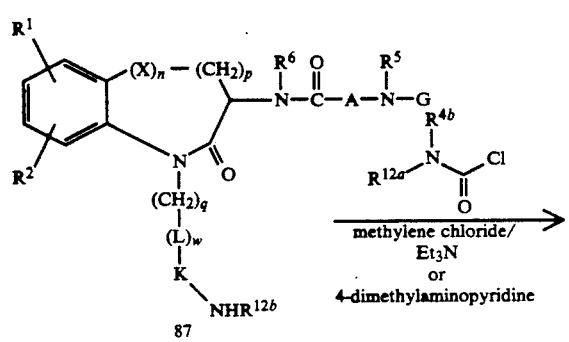
87
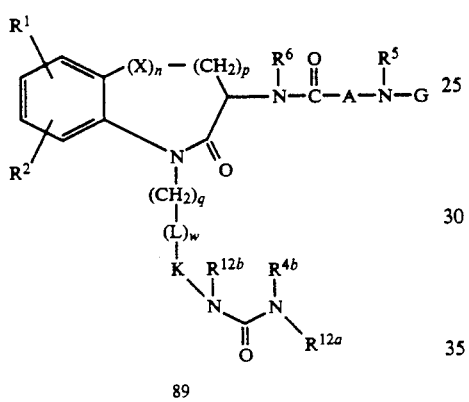
89
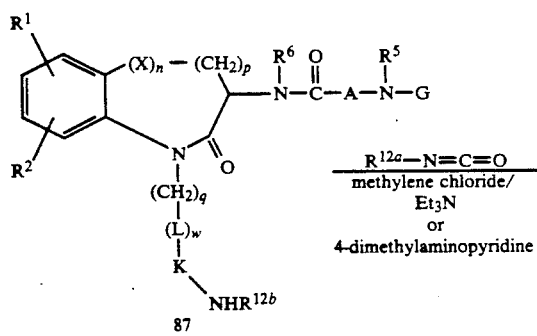
87
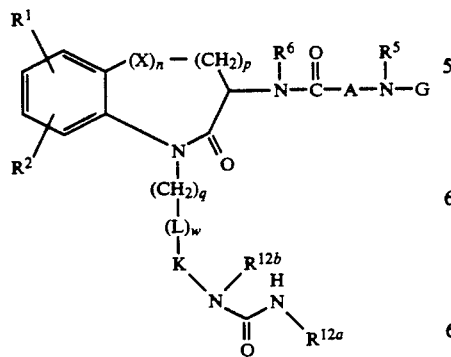
90
SCHEME 28
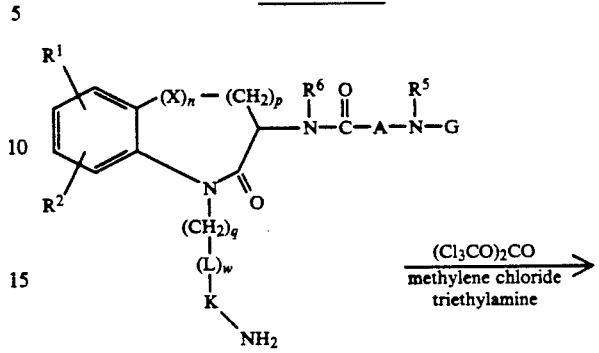
86
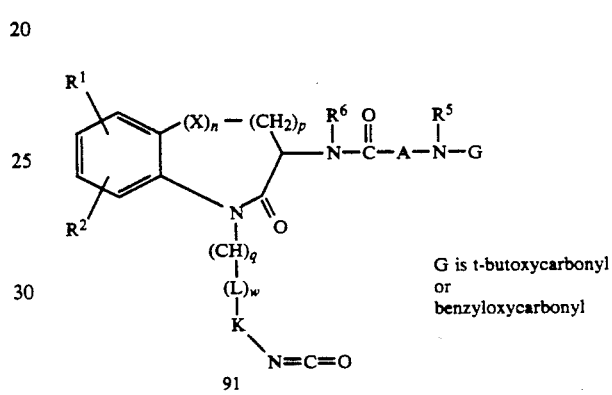
91
G is t-butoxycarbonyl
or
benzyloxycarbonyl
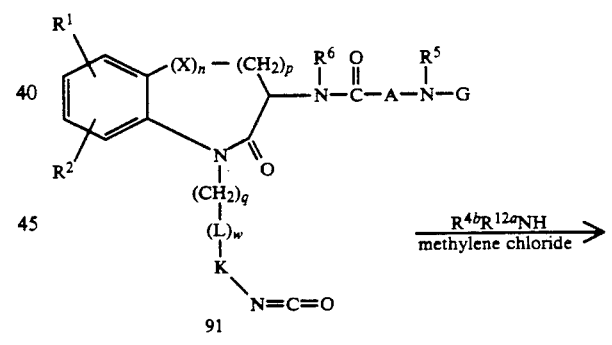
91
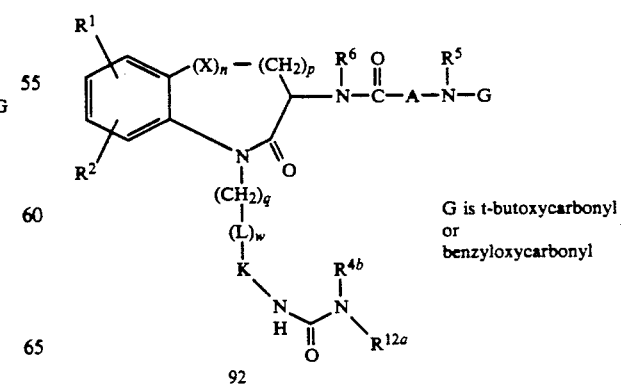
92
G is t-butoxycarbonyl
or
benzyloxycarbonyl

-continued
SCHEME 28

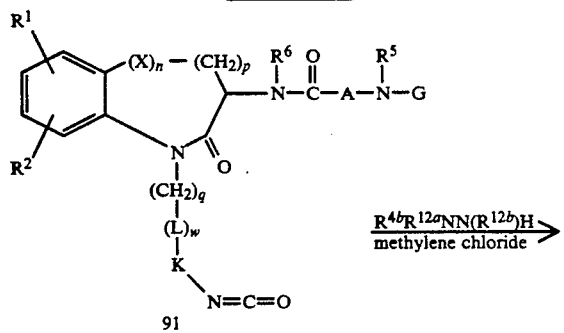

91

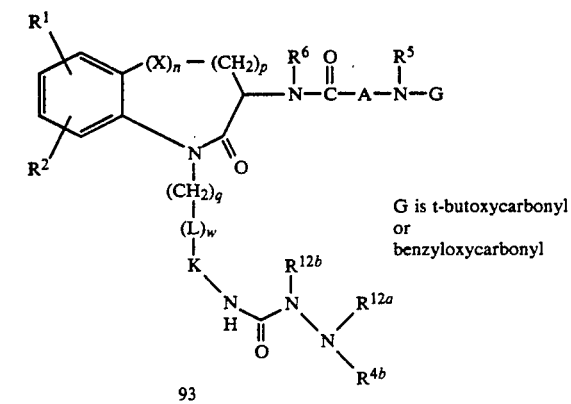

93  G is t-butoxycarbonyl or benzyloxycarbonyl

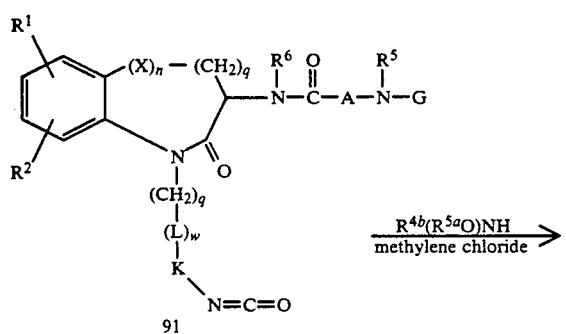

91

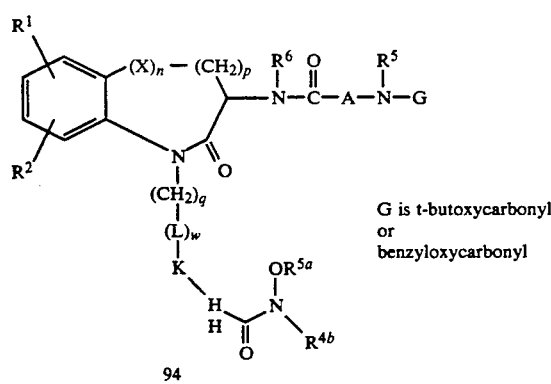

94  G is t-butoxycarbonyl or benzyloxycarbonyl

Compounds of formula I where $R^3$ is a carbazate or carbamate derivative where attachment to the phenyl ring is through the oxygen atom of the carbazate or carbamate linkage are prepared from the acetophenone intermediate 95 as indicated in Scheme 29.

Oxidative rearrangement of 95 through the use of a peroxy-carboxylic acid (Baeyer-Villager reaction) such as m-chloroperbenzoic acid gives the ester 96 which is hydrolyzed in the presence of a strong base such as sodium or lithium hydroxide to give phenol 97.

Reaction of 97 with an isocyanate leads directly to carbamate analogs 98. Additionally, treatment of 97 with N,N'-carbonyldiimidazole in dimethylformamide can form an activated intermediate which will react with substituted hydrazine reagents to give carbazate products 99.

SCHEME 29

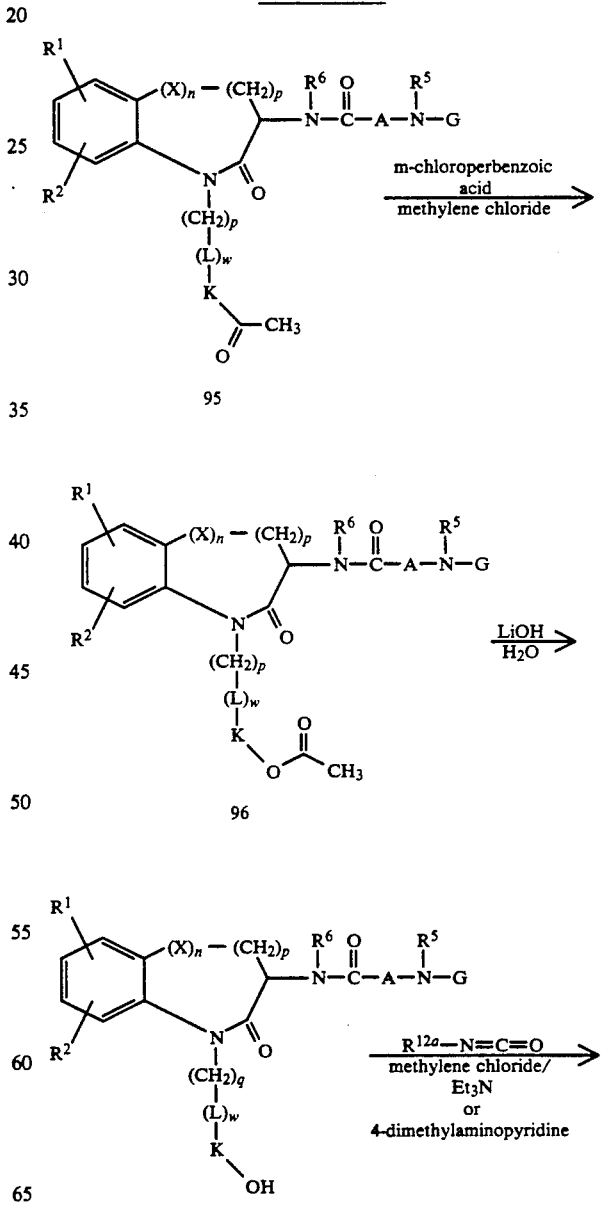

-continued
SCHEME 29

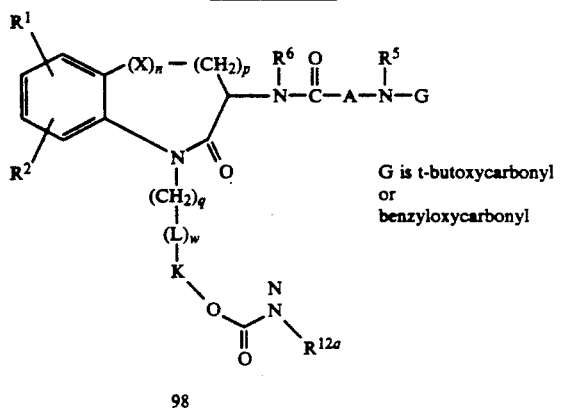

98

G is t-butoxycarbonyl or benzyloxycarbonyl

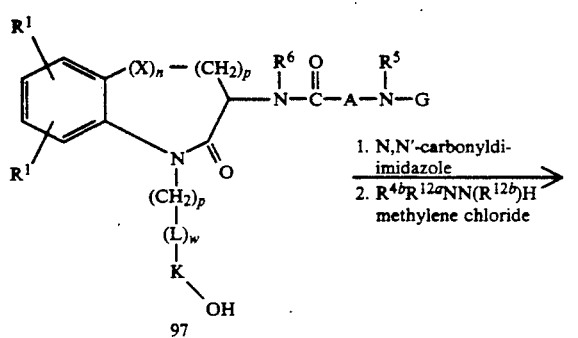

97

1. N,N'-carbonyldi-imidazole
2. $R^{4b}R^{12a}NN(R^{12b})H$
methylene chloride

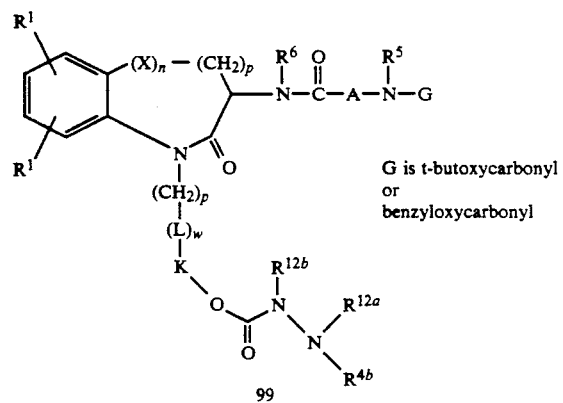

99

G is t-butoxycarbonyl or benzyloxycarbonyl

Compounds of formula I wherein $R^3$ contains the linkage $-CH_2N(R^{12b})-$ can be prepared from the t-butyl ester intermediate 100 as described in Scheme 30. Removal of the t-butyl ester through the use of trifluoroacetic acid gives the carboxylic acid 82. It may be appreciated by one skilled in the art that the protecting group G in 100 must therefore be compatible with the strongly acidic conditions employed for ester cleavage, hence G is taken as benzyloxycarbonyl. Conversion of the carboxylic acid to the benzylamine derivative 102 can be achieved by a five-step sequence consisting of: 1) formation of a mixed anhydride with isobutyl chloroformate; 2) reduction with sodium borohydride to the benzyl alcohol; 3) formation of the mesylate with methanesulfonyl chloride; 4) formation of the azide by reaction with sodium azide, and finally, 5) reduction of the azide with tin(II) chloride. The benzylamine intermediate 102 can be further elaborated to 103 by the aforementioned reductive amination procedure.

SCHEME 20

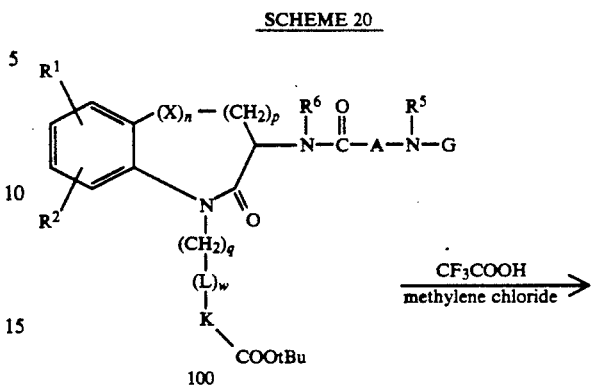

100

$\xrightarrow{CF_3COOH}{\text{methylene chloride}}$

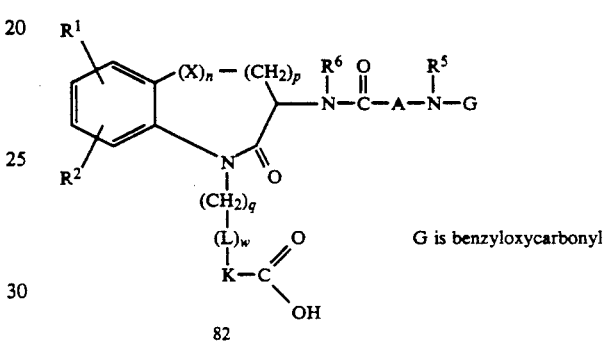

82

G is benzyloxycarbonyl 1. iBu—O—C(=O)—Cl, N-methylmorpholine
2. sodium borohydride
3. $CH_3SO_2Cl$
4. sodium azide
5. $SnCl_2$, aqueous dioxane

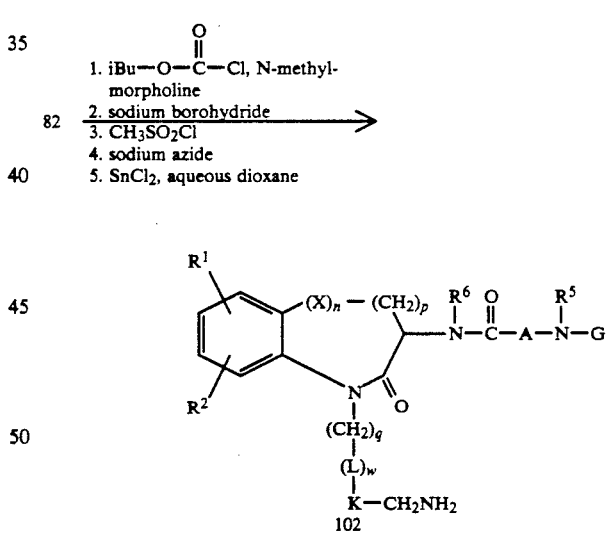

102

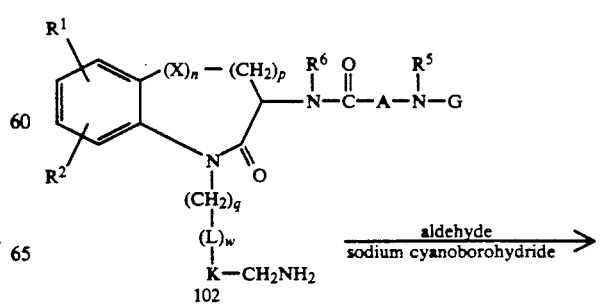

102

$\xrightarrow{\text{aldehyde}}{\text{sodium cyanoborohydride}}$

-continued
SCHEME 20
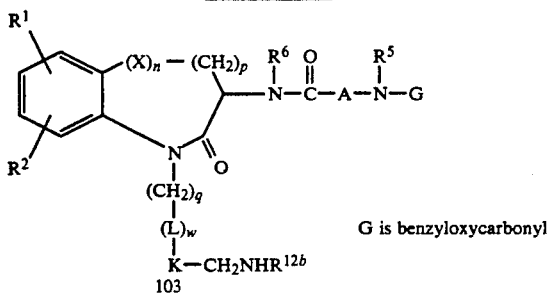
G is benzyloxycarbonyl
Reaction of amine 103 with the appropriate reagents to form urea-linked compounds 104 and 105, carbamate-linked compounds 106, and amide-linked structures 107 are illustrated in Scheme 31.
SCHEME 31
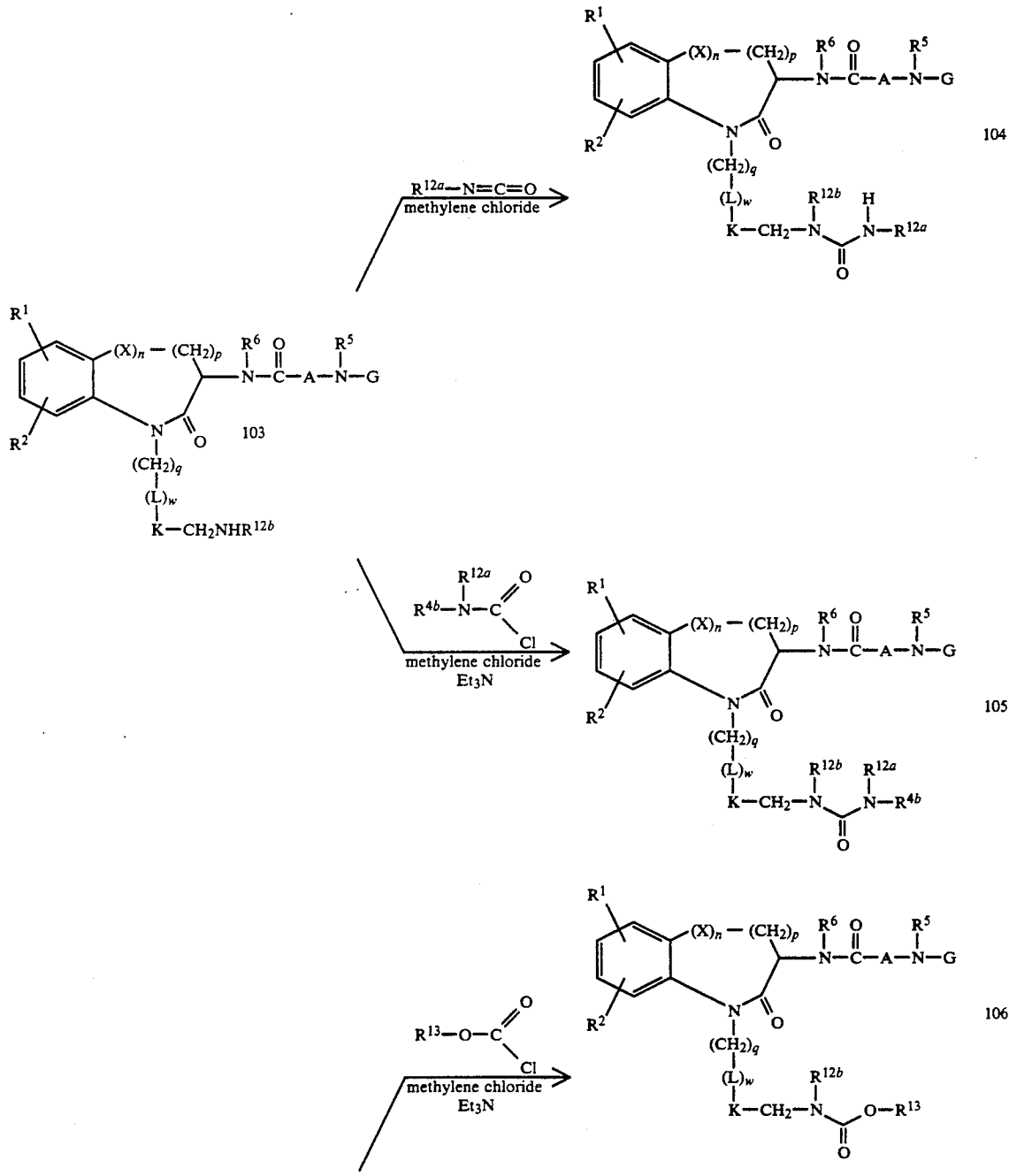

-continued
SCHEME 31

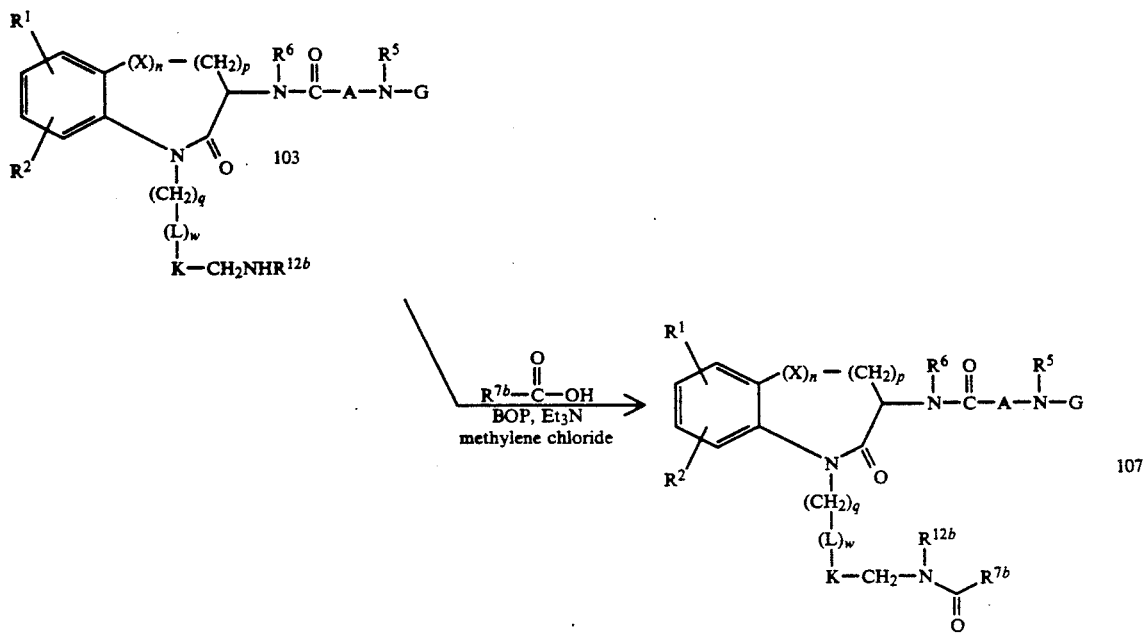

G is benzyloxycarbonyl

Conversion to the final products of formula I wherein $R^4$ is hydrogen, is carried out by simultaneous or sequential removal of all protecting groups from intermediate VII as illustrated in Scheme 32 Removal of benzyloxycarbonyl groups can be achieved by a number of methods known in the art; for example, catalytic hydrogenation with hydrogen in the presence of a platinum or palladium catalyst in a protic solvent such as methanol. In cases where catalytic hydrogenation is contraindicated by the presence of other potentially reactive functionality, removal of benzyloxycarbonyl groups can also be achieved by treatment with a solution of hydrogen bromide in acetic acid. Catalytic hydrogenation is also employed in the removal of N-triphenylmethyl (trityl) protecting groups. Removal of t-butoxycarbonyl (BOC) protecting groups is carried out by treatment of a solution in a solvent such as methylene chloride or methanol, with a strong acid, such as hydrochloric acid or trifluoroacetic acid. Conditions required to remove other protecting groups which may be present can be found in *Protective Groups in Organic Synthesis*.

-continued
SCHEME 32

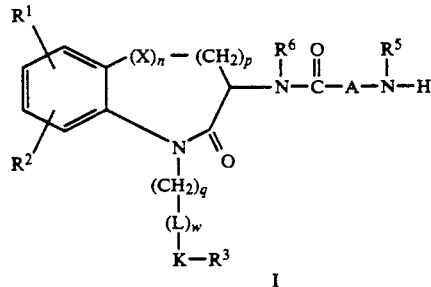

Compounds of formula I wherein $R^4$ and $R^5$ are each hydrogen can be further elaborated by reductive alkylation with an aldehyde by the aforementioned procedures or by alkylations such as by reaction with various epoxides as shown in Scheme 33. The products, obtained as hydrochloride or trifluoroacetate salts, are conveniently purified by reverse phase high performance liquid chromatography (HPLC) or by recrystallization.

SCHEME 32

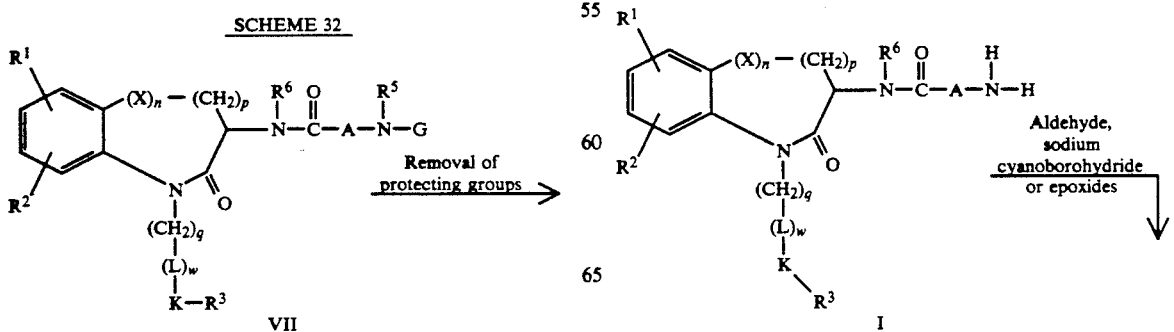

-continued
SCHEME 33

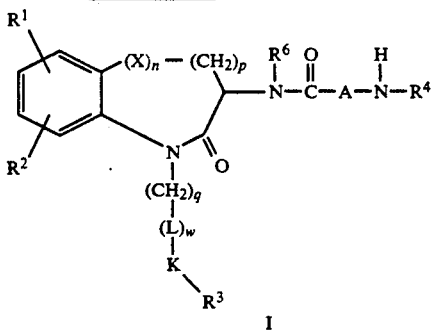

It is noted that the order of carrying out the foregoing reaction schemes is not significant and it is within the skill of one skilled in the art to vary the order of reactions to facilitate the reaction or to avoid unwanted reaction products.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive intestinal peptides, e.g., bombesin; and the thyroid hormones, e.g., thyroxine and triiodothyronine. The compounds of Formula I can also be employed to investigate the possible negative or positive feedback effects of some of the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For example, the compounds can be administered to commercially important animals such as swine, cattle, sheep and the like to accelerate and increase their rate and extent of growth, and to increase milk production in such animals. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical carrier or diluent. Optionally, the active ingredient of the pharmaceutical compositions can comprise a growth promoting agent in addition to at least one of the compounds of Formula I or another composition which exhibits a different activity, e.g., an antibiotic or other pharmaceutically active material.

Growth promoting agents include, but are not limited to, TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

A still further use of the disclosed novel benzo-fused lactam growth hormone secretagogues is in combination with other growth hormone secretagogues such as GHRP-6, GHRP-1 as described in U.S. Pat. Nos. 4,411,890; and publications WO 89/07110 and WO 89/07111 and B-HT920 or growth hormone releasing factor and its analogs or growth hormone and its analogs or somatomedins including IGF-1 and IGF-2. A still further use of the disclosed novel benzo-fused lactam growth hormone secretagogues is in combination with $\alpha_2$ adrenergic agonists or $\beta_3$ adrenergic agonists in the treatment of obesity or in combination with parathyroid hormone or bisphosphonates, such as MK-217 (alendronate), in the treatment of osteoporosis.

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses of growth hormone may be summarized as follows: stimulating growth hormone release in elderly humans; Prevention of catabolic side effects of glucocorticoids, treatment of osteoporosis, stimulation of the immune system, treatment of retardation, acceleration of wound healing, accelerating bone fracture repair, treatment of growth retardation, treating renal failure or insufficiency resulting in growth retardation, treatment of physiological short stature, including growth hormone deficient children, treating short stature associated with chronic illness, treatment of obesity and growth retardation associated with obesity, treating growth retardation associated with Prader-Willi syndrome and Turner's syndrome; Accelerating the recovery and reducing hospitalization of burn patients; Treatment of intrauterine growth retardation, skeletal dysplasia, hypercortisolism and Cushings syndrome; Induction of pulsatile growth hormone release; Replacement of growth hormone in stressed patients; Treatment of osteochondrodysplasias, Noonans syndrome, schizophrenia, depression, Alzheimer's disease, delayed wound healing, and psychosocial deprivation; treatment of pulmonary dysfunction and ventilator dependency; Attenuation of protein catabolic response after a major operation; reducing cachexia and protein loss due to chronic illness such as cancer or AIDS. Treatment of hyperinsulinemia including nesidioblastosis; Adjuvant treatment for ovulation induction; To stimulate thymic development and prevent the age-related decline of thymic function; Treatment of immunosuppressed patients; Improvement in muscle strength, mobility, maintenance of skin thickness, metabolic homeostasis, renal hemeostasis in the frail elderly; Stimulation of osteoblasts, bone remodelling, and cartilage growth; Stimulation of the immune system in companion animals and treatment of disorders of aging in companion animals; Growth promotant in livestock; and stimulation of wool growth in sheep.

The compounds of this invention can be administered by oral, parenteral (e.g., intramuscular, intraperitoneal, intravenous or subcutaneous injection, or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions or nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 100 mg/kg. of body weight daily are administered to patients and animals, e.g., mammals, to obtain effective release of growth hormone.

The following examples are provided for the purpose of further illustration only and are not intended to be limitations on the disclosed invention. Unless specified otherwise, all $^1H$ and $^{13}C$ NMR chemical shifts are reported in ppm on the δ scale using residual chloroform in $CDCl_3$ as an internal standard.

EXAMPLE 1

3-Amino-N-[1-[[3-[2-(1H-tetrazol-5-yl)phenyl]-5-isoxazolyl]methyl]2,3,4,5-tetrahydro-2-oxo-1H-1-benzazepin-3(R)-yl]-3-methylbutanamide, trifluoroacetate Step A: 1-Tetralone oxime To 4.6 L of water at room temperature in a 4-neck 50 L flask sitting in a steam bath apparatus equipped with an overhead stirrer, a temperature probe and reflux condenser was added 3.72 Kg (27.36 mol) of sodium acetate with stirring, followed by 1.9 Kg of hydroxylamine hydrochloride (27.36 mol). To this slurry at room temperature, 12 L of ethanol was added followed by 1.994 Kg (13.68 mol) of 1-tetralone. Additional ethanol (1.7 L) was used to rinse off the funnel and added to the reaction mixture. The resulting light orange slurry was heated to 75° C. over 40 minutes and maintained at 75°-85° C. for another 75 minutes. The reaction mixture was cooled with the aid of ice packed around the flask. When the internal temperature reached 32° C., the reaction mixture was pumped over 15 minutes into 60 L of ice contained in a 200 L vessel. The reaction vessel was washed with an additional 2 L of water which was added to the 200 L vessel. When the ice melted, the mixture was filtered through a filter pad and the wet cake washed with 4 L of water. The wet cake was suction dried for 1 hour then transferred to two trays and dried under vacuum at 40° C. for 2 days to give 2.094 Kg (13.01 mol, 95%) of product. $^1H$ NMR (250 MHz, $CDCl_3$): 1.90 (m,2H), 2.80 (t,6 Hz,2H), 2.88 (t,6 Hz,2H), 7.15-7.35 (m,3H), 7.90 (d,8 Hz,1H), 8.9 (br s,1H).

Step B: 2,3,4,5-Tetrahydro-1H-1-benzazepin-2-one

To 10 L of methanesulfonic acid in a 22 L 3-neck flask equipped with an overhead stirrer, a temperature probe, nitrogen inlet and reflux condenser was added 2.6 Kg (18.61 mol) of phosphorus pentoxide. An additional 1.6 L of methanesulfonic acid was used to wash all the phosphorus pentoxide into the vessel. The mixture was heated at 90° C. for 2.5 hours then cooled to 50° C. using an ice bath and treated with 2.00 Kg (12.41 mol) of 1-tetralone oxime in several portions over 15 minutes. The mixture was heated at 63° C. for 10 minutes then slowly heated to 80° C. and kept at 80° C. for 3 hours. The reaction mixture was pumped into 70 L of ice then treated slowly with 11.25 L of 50% aqueous sodium hydroxide over 90 minutes at such a rate so as to maintain the temperature below 28° C. The mixture was filtered and 4 L of the filtrate was used to rinse the vessel. The wet cake (pink) was washed with 8 L of water then suction dried for 45 minutes then transferred to two trays and dried under vacuum at 40° C. for 2 days to give 1.9 Kg (11.79 mol, 95%) of product. $^1H$ NMR (250 MHz, $CDCl_3$): 2.24 (m,2H), 2.38 (t,6 Hz,2H), 2.82 (t,6 Hz,2H), 7.03 (d,8 Hz,1H), 7.13 (m,1H), 7.24 (m,2H), 8.63 (br s,1H).

Step C: 3-Iodo-2,3,4,5-tetrahydro-1H-1-benzazepin-2-one

A suspension of 1.8 Kg (11.17 mol) of 2,3,4,5-tetrahydro-1H-1-benzazepin-2-one in a mixture of 22.33 L of methylene chloride and 11.78 L (55.83 mol) of hexamethyldisilazane was heated at reflux for 10 minutes then cooled to 30° C. and treated with 8.503 Kg (33.5 mol) of iodine in one portion. The mixture was heated at reflux for 2.5 hours then cooled to room temperature. Aqueous sodium sulfite containing 4.926 Kg of sodium sulfite in 44 L of water was cooled to 0° C. and into it was poured the reaction mixture in several portions with vigorous stirring while maintaining the temperature below 10° C. The reaction vessel was rinsed with 22.33 L of methylene chloride and the washing transferred to the quenching mixture. The quenching mixture was stirred vigorously and the layers allowed to separate. The aqueous layer was removed and reextracted with 22.33 L of methylene chloride. The combined organic layers were washed with 11 L of water and concentrated under vacuum to a final volume of approximately 5 L. The residue was treated with 55 L of toluene and concentrated under vacuum to a final volume of 10 L. The resulting slurry was removed by filtration and the filter cake washed with an additional 5 L of toluene and dried under vacuum at ambient temperature for 24 hours to give 1.842 Kg (6.42 mol, 57%) of product. $^1$H NMR (200 MHz, CDCl$_3$): 2.6–2.8 (m,3H), 2.93 (m,1H), 4.64 (t,8 Hz,1H), 6.97 (d,8 Hz,1H), 7.10–7.35 (m,3H), 7.55 (br s,1H).

Step D: 3(R)-Amino-2,3,4,5-tetrahydro-1H-1-benzazepin-2-one, D-tartaric acid salt 3-Iodo-2,3,4,5-tetrahydro-1H-1-benzazepin-2-one (1.79 Kg, 6.24 mol) was slurried in 6.2 L of methanol and the slurry charged into an autoclave. Condensed ammonia (1.55 L) was added and the autoclave closed, with stirring, and heated to 100° C. over 1 hour. Heating at 100° C. was continued for 2 hours then the autoclave was allowed to cool to room temperature over 1 hour, during which time the internal pressure was 150–155 psi. The reaction mixture was transferred to a polyethylene jug and the autoclave rinsed with 2×8 L of methanol. The washings were concentrated under vacuum at 30° C. then combined with the reaction mixture and concentrated to near dryness under vacuum at 30° C. The resulting residue was dissolved in 4 L of ethyl acetate then concentrated to dryness under vacuum at 30° C.

Sodium chloride (712 g) was dissolved in 2 L of water and 1.0 Kg of sodium carbonate was dissolved in 6 L of water. Two liters of the sodium carbonate solution was added to the concentrated residue and the resulting slurry transferred to an extraction flask. Another 2 L portion of the sodium carbonate solution was added to the residue flask and the solution transferred to the extraction flask. The remaining sodium carbonate solution was used in the same way. The sodium chloride solution was added to the sodium carbonate/aminolactam emulsion and the resulting mixture stirred for 10 minutes then extracted with four 6 L portions of methylene chloride. The combined methylene chloride layers were concentrated to dryness; the residue was treated with 2 L of 200 proof ethanol and the resulting slurry concentrated to dryness under vacuum to give 1.171 Kg of crude product.

The crude product was slurried in 8 L of ethanol and treated with 900 g of D-tartaric acid in one portion. Water (7 L) was added and the mixture heated to 77° C., then additional ethanol (45 L) was added and heating continued. The solution was cooled to 43° C. and treated with the seed slurry. (The seed slurry was prepared by the route described above starting with 10.50 g of crude product and 9.1 g of D-tartaric acid.) The solution was aged at room temperature for 48 hours. The slurry formed was removed by filtration and the wet cake washed with 1.8 L of ethanol. The resulting filter cake was suction dried with nitrogen bleeding for 20 hours then transferred into a drying tray and dried under vacuum for 24 hours to give 354 g (1.085 mol, 17.4%) of the product. $^1$H NMR (250 MHz,CDCl$_3$): 2.13 (m,1H), 2.51 (m,2H), 2.73 (m,2H), 3.68 (t,6 Hz,1H), 3.98 (s,2H), 7.05 (d,8 Hz,1H), 7.16 (t,8 Hz,1H), 7.30 (m,2H), 7.6 (br s,5H), 10.26 (br s,1H).

Step E: 3(R)-Amino-2,3,4,5-tetrahydro-1H-1-benzazepin-2-one

A solution of 229.23 g (0.700 mol) of 3(R)-amino-2,3,4,5-tetrahydro-1H-1-benzazepin-2-one, D-tartrate in 4.1 L of water was treated with 194 g (1.40 mol) of potassium carbonate. Subsequent portions of 100 g and 135 g of potassium carbonate were added until the pH was 10.5. The mixture was extracted with four 4 L portions of methylene chloride which were then combined and dried over magnesium sulfate. The aqueous layer was treated with 1.4 Kg of sodium chloride and reextracted with four 4 L portions of methylene chloride which were then combined and dried over magnesium sulfate. The two 16 L batches of extracts were combined, filtered and concentrated to dryness under vacuum to give 115.5 g of product which contained 1.6% of an impurity identified as 7-iodo-3(R)-amino-2,3,4,5-tetrahydro-1H-1-benzazepin-2-one.

A solution of 107.02 g (0.607 mol) of the intermediate obtained above in 1.712 L of ethanol was hydrogenated at room temperature and 40 psi over 4.00 g of 10% palladium on carbon for 4 hours. The catalyst was removed by filtration through solkaflok and the filtrate concentrated to dryness under vacuum to give 101.08 g (0.574 mol, 94.4%) of product.

Step F: 4,4-Dimethylazetidin-2-one

A 3-neck 3 L round bottom flask equipped with a magnetic stirrer, thermometer, cold finger condenser and nitrogen bubbler was charged with 1 L of ether. The flask was cooled to −65° C. and into it was condensed 500–600 mL of isobutylene. The cold finger condenser was replaced with a dropping funnel and 200 mL (325 g, 2.30 mol) of chlorosulfonyl isocyanate was added dropwise over 1.5 hours. The mixture was maintained at −65° C. for 1.5 hours then the dry ice/acetone cooling bath replaced with methanol/ice and the internal temperature slowly increased to −5° C. at which time the reaction initiated and the internal temperature rose to 15° C. with evolution of gas. The internal temperature remained at 15° C. for several minutes then dropped back down to −5° C. and the mixture stirred at −5° C. for 1 hour. The methanol/ice bath was removed and the reaction mixture warmed to room temperature and stirred overnight.

The reaction mixture was transferred to a 3-neck 12 L round bottom flask fitted with a mechanical stirrer and diluted with 2 L of ether. The well stirred reaction mixture was treated with 2 L of saturated aqueous sodium sulfite. After 1 hour, an additional 1 L of saturated aqueous sodium sulfite was added followed by sufficient sodium bicarbonate to adjust the pH to approximately 7. The mixture was stirred another 30 minutes then the layers allowed to separate. The ether layer was removed and the aqueous layer reextracted with 2×1 L of ether. The combined ether extracts were washed once with 500 mL of saturated aqueous sodium bicarbonate and once with 500 mL of saturated aqueous sodium chloride. The ether layer was removed, dried over magnesium sulfate, filtered and concentrated under vacuum to give 33 g of a pale yellow oil. The aqueous layer was made basic by the addition of solid sodium bicarbonate and extracted with 3×1 L of ether. The combined ether extracts were washed and dried as described above, then combined with the original 33 g of pale yellow oil and concentrated under vacuum to give 67.7 g of product. Further extraction of the aqueous layer with 4×1 L of methylene chloride and washing and drying as before gave an additional 74.1 g of product. Still further extraction of the aqueous layer with 4×1 L of methylene chloride gave an additional 21.9 g of product. The combined product (163.7 g, 1.65 mol, 72%) was used in Step G without purification. $^1$H NMR (200 MHz,CDCl$_3$): 1.45 (s,6H), 2.75 (d,3 Hz,2H), 5.9 (br s,1H).

Step G: N-(t-Butoxycarbonyl)-4,4-dimethylazetidin-2-one

A 5 L, 3-neck round bottom flask equipped with a magnetic stirrer, thermometer, nitrogen bubbler and addition funnel was charged with 88.2 g (0.89 mol) of 4,4-dimethylazetidin-2-one (Step F), 800 mL of methylene chloride, 150 mL of triethylamine (1.08 mol) and 10.9 g (0.089 mol) of 4-dimethylaminopyridine. To the stirred solution at room temperature was added dropwise over 15 minutes a solution of 235 g (1.077 mol) of di-t-butyl-dicarbonate in 300 mL of methylene chloride. The reaction mixture was stirred at room temperature overnight then diluted with 1 L of methylene chloride and washed with 500 mL of saturated aqueous ammonium chloride, 500 mL of water, and 500 mL of saturated aqueous sodium chloride. The organic layer was separated, dried over magnesium sulfate, filtered and concentrated under vacuum to afford 180.3 g of crude product as an orange solid. The material was used directly in Step H without purification. $^1$H NMR (200 MHz,CDCl$_3$): 150 (s,9H), 1.54 (s,6H), 2.77 (s,2H).

Step H: 3-t-Butoxycarbonylamino-3-methylbutanoic acid

A 3 L, 3-neck round bottom flask equipped with a magnetic stirrer, thermometer, nitrogen bubbler and addition funnel was charged with 180.3 g (0.89 mol) of N-(t-butoxycarbonyl)-4,4-dimethylazetidin-2-one dissolved in 1 L of tetrahydrofuran. The solution was cooled to 0°-5° C. and treated dropwise with 890 mL of 1.0M aqueous lithium hydroxide over 30 minutes. The reaction mixture was stirred at 0°-5° C. for 2 hours then diluted with 1 L of ether and 1 L of water. The layers were allowed to separate and the aqueous layer reextracted with an additional 1 L of ether. The aqueous layer was acidified by the addition of 1 L of saturated aqueous sodium bisulfate, then extracted with 1×1 L and 2×500 mL of ether. The combined organic layer and ether extracts were washed with 500 mL of saturated aqueous sodium chloride, dried over magnesium sulfate and concentrated under vacuum to 173 g of a yellow oil that solidified upon standing. The material was slurried with warm hexane then filtered and dried under high vacuum to afford 168.5 g (0.775 mol, 87%) of product as a white solid. $^1$H NMR (200 MHz,CDCl$_3$): 1.39 (s,6H), 1.44 (s,9H), 2.72 (s,2H). FAB-MS: calculated for C$_{10}$H$_{19}$NO$_4$ 217; found 218 (M+H,54%).

Step I: 3-t-Butoxycarbonylamino-3-methyl-N-[2,3,4,5-tetrahydro-2-oxo-1H-1-benzazepin-3(R)-yl]butanamide A solution of 8.70 g (49.4 mmol) of 3(R)-amino-2,3,4,5-tetrahydro-1H-1-benzazepin-2-one (Step E) in 100 mL of methylene chloride was treated with 10.73 g (49.4 mmol) of 3-t-butoxycarbonylamino-3-methylbutanoic acid (Step H) and 13.8 mL of triethylamine (10.0 g, 99 mmol, 2 eq.). The reaction flask was immersed in an ambient temperature water bath then 26 g of benzotriazol-1-yloxytris(dimethylamino)phosphonium hexafluorophosphate (59 mmol, 1.2 eq) was added all at once and the mixture stirred at room temperature for 2 hours. The reaction mixture was added to 300 mL of ethyl acetate and washed three times with 5% aqueous citric acid, twice with saturated aqueous sodium bicarbonate and once with saturated aqueous sodium chloride. The organic layer was removed, dried over magnesium sulfate, filtered and the filtrate concentrated under vacuum. The residue was purified by preparative high pressure liquid chromatography on silica, eluting with ethyl acetate/hexane (4:1), to afford 17.42 g (46.4 mmol, 94%) of the product as a white solid. $^1$H NMR (200 MHz,CDCl$_3$): 1.37 (s,6H), 1.44 (s,9H), 1.95 (m,1H), 2.46 (d,15 Hz,1H), 2.59 (d,15 Hz,1H), 2.60-3.0, (m,3H), 4.53 (m,1H), 5.30 (br s,1H), 6.72 (d,7 Hz,1H), 6.98 (d,8 Hz, 1H), 7.1-7.3 (m,3H), 7.82 (br s,1H). FAB-MS: calculated for C$_{20}$H$_{29}$N$_3$O$_4$ 375; found 376 (M+H,70%).

Step J: 5-Phenyltetrazole

Zinc chloride (3.3 g, 24.3 mmol, 0.5 eq) was added to 15 mL of N,N-dimethylformamide in small portions while maintaining the temperature below 60° C. The suspension of zinc chloride was cooled to room temperature and treated with 5.0 g of benzonitrile (48.5 mmol, 1.0 eq) followed by 3.2 g of sodium azide (48.5 mmol, 1.0 eq). The heterogeneous mixture was heated at 115° C. with agitation for 18 hours. The mixture was cooled to room temperature, water (30 mL) was added and the mixture acidified by the addition of 5.1 mL of concentrated hydrochloric acid. The mixture was cooled to 0° C. and aged for one hour, then filtered and the filter cake washed with 15 mL of cold 0.1N HCl then dried at 60° C. under vacuum to afford 6.38 g (43.7 mmol, 90%) of the product.

Step K: 5-Phenyl-2-trityltetrazole

To a suspension of 5.0 g (34.2 mmol) of 5-phenyltetrazole in 55 mL of acetone was added 5.0 mL of triethylamine (3.6 g, 35.6 mmol, 1.04 eq). After 15 minutes, a solution of 10.0 g of triphenylmethyl chloride (35.9 mmol, 1.05 eq) in 20 mL of tetrahydrofuran was added and the mixture stirred at room temperature for one hour. Water (75 mL) was slowly added and the mixture stirred for one hour at room temperature. The product was collected by filtration, washed with 75 mL of water and dried at 60° C. under vacuum to give 13.3 g (34.2 mmol, 100%) of the product.

Step L: 5-(2-Formylphen-1-yl)-2-trityltetrazole

The starting material (from Step K, 1.5 g, 3.87 mmol, 1.0 equiv) was weighed in a flame-dried 35 ml pear-shaped flask, dissolved in 15 ml freshly distilled THF (over sodium metal and benzophenone), cooled down to −20° C. (carbon tetrachloride/dry ice bath), and purged with N$_2$.

A few drops of n-butyllithium solution (1.56M in THF) was added into the starting material solution until a persistent red color was observed, then 2.7 ml (4.25 mmol, 1.1 equiv) was added dropwise at −90° C. The resultant red solution was stirred at −20° C. for 2 hours, and then cannulated into a solution of 0.95 ml (7.73 mmol, 2.0 equiv) N-methyl-N-(2-pyridyl)-formamide in 8 ml THF in a flame-dried 50 ml round-bottom flask at −20° C. The red color faded to yellow within 10 minutes after the cannulation was complete. The formylation reaction was quenched after 1.25 hours with saturated aqueous sodium bicarbonate solution, and 20 ml ethyl acetate was added to dissolve the organics. The layers were separated, and the aqueous layer was extracted with 5×20 ml ethyl acetate. The combined organic portion was washed with saturated aqueous sodium bicarbonate solution, dried over anhydrous sodium sulfate, filtered, concentrated, and chromatographed (6 cm×29 cm, 25:6:1=hexane: methylene chloride: ethyl acetate, with 1% distilled triethylamine) to afford 1.23 g (77%) of the desired product as a foam: Rf=0.23 (25:6:1=hexane: methylene chloride:ethyl acetate, with 1% distilled triethylamine); $^1$H NMR $\delta$10.52 (s, HCO), 8.16–8.14 (dd), 8.06–8.04 (dd), 7.72–7.67 (dt), 7.60–7.54 (dt); FAB-MS: Calculated $C_{27}H_{20}N_4O$=416.5, found 577.7 (M+Li+Ms, 45%), 242.9 (trityl, 100%).

Step M: 2-[2-(triphenylmethyl)-2H-tetrazol-5-yl]benzaldehyde oxime

A 10 ml round-bottom flask equipped with a magnetic stirring bar, septum, and nitrogen inlet was charged with 300 mg (0.72 mmol, 1.0 equiv) of the starting aldehyde (from Step L) and 3 ml pyridine (over sieves). Into this clear solution was added 76 mg (1.08 mmol, 1.5 equiv) of the hydrochloride salt of $H_2NOH$ at room temperature in one portion. The reaction was stopped after 5.5 hours with the addition of saturated aqueous sodium bicarbonate solution and ethyl acetate. The organic layer was separated from the aqueous one, which was then extracted with 5×5 ml ethyl acetate. The combined organic layers were washed with 2×20 ml saturated aqueous sodium bicarbonate solution, dried over anhydrous sodium sulfate, concentrated to afford 346 mg of the crude product, the $^1$H NMR of which showed scarcely any impurity. This material would be used in the next reaction without purification.

Step N: O-Pivaloyl-propargyl alcohol

A 250 ml round-bottom flask, equipped with a magnetic stirring bar, septum, and nitrogen inlet, was charged with 20 ml methylene chloride and 10 ml (0.172 mol, 1.0 equiv) propargyl alcohol. The resultant clear solution was cooled down to 0° C. 3 mg (0.026 mol, 0.15 equiv) of DMAP was added, followed by the addition of 60 ml (0.344 mol, 2.0 equiv) of diisopropylethylamine. 32 ml (0.129 mol, 1.4 equiv) of pivaloyl chloride was added over a period of 10 minutes. The resultant solution was stirred at 0° C. for 40 minutes, and then warmed up to room temperature.

The reaction was quenched at 0° C. with chilled methylene chloride and saturated aqueous sodium bicarbonate solution after 2.5 hours. The mixture was then warmed up to room temperature and stirred for 20 minutes. The organic layer was separated from the aqueous one, which was then extracted with 7×30 ml methylene chloride. The combined organic portion was washed with 3×50 ml saturated aqueous sodium bicarbonate solution, dried over anhydrous sodium sulfate, filtered, concentrated, and chromatographed on a silica gel column (7 cm×27 cm, 6:1=hexane: ethyl acetate). Because the product after the silica gel column was still contaminated by $^1$H NMR, short-path distillation was used for purification and afforded 14.6 g of clean product (bp.=151°–154° C./1 atm.): $^1$H NMR $\delta$4.64 (d, $CH_2O$, J=2.31 Hz), 2.42 (t,HCC,J=2.40 Hz), 1.20 (s, tBu).

Step O: [3-[2-(2-Trityltetrazol-5-yl)phenyl]-5-isoxazolyl]methyl pivaloate

Into a 50 ml round-bottom flask equipped with magnetic stirring bar, septum, and nitrogen inlet was charged with 311 mg (0.72 mmol, 1.0 equiv) of the starting oxime (from Step M) and 6 ml DMF (over sieves). The resultant clear solution was cooled down to 0° C.

Into a 5 ml flask was added 193 mg (1.08 mmol, 1.5 equiv) or N-bromosuccinimide and 2 ml DMF. The resultant solution was cannulated into the oxime solution over 3 minutes at 0° C. The solution was kept at 0° C. for one hour, and during this time it gradually turned bright yellow. 505 mg (3.61 mmol, 5.0 equiv) of the O-pivaloylpropargyl alcohol (from Step N) and 151 $\mu$l (1.08 mmol, 1.5 equiv) distilled (over $CaH_2$) triethylamine were added alternatingly at 0° C. over four minutes. The yellow color faded, and precipitation occurred. The reaction was warmed up to room temperature and stirred overnight.

The reaction was quenched after 12.5 hours with saturated aqueous sodium bicarbonate solution, and ethyl acetate was added to dissolve the organics. Layers were separated, and 5×10 ml ethyl acetate was used to extract the aqueous portion. The combined organic layers were washed with 3×20 ml saturated aqueous sodium bicarbonate solution, dried over anhydrous sodium sulfate, filtered, concentrated, and purified on a silica gel column (3 cm×29 cm, 25:6:1==hexane:-methylene chloride:ethyl acetate, with 1% distilled triethylamine) to afford 348 mg of the title compound in 85% yield: Rf=0.13 (25:6:1=hexane:methylene chloride: ethyl acetate, with 1% distilled triethylamine); $^1$H NMR $\delta$5.95 (s, HC on the isoxazole ring), 4.85 (s, $CH_2O$), 1.17 (s, tBu); $^{13}$C NMR $\delta$105.0 (HC on the isoxazole ring), 83.2 (C)$C_6H_5)_3$), 56.5 ($CH_2O$), 27.1 ($C(CH_3)_3$).

Step P: [3-[2-(2-Trityltetrazol-5-yl)phenyl]-5-isoxazolyl]methanol

A 100 ml round-bottom flask, equipped with a magnetic stirring bar, septum, and nitrogen inlet, was charged with 348 mg (0.61 mmol, 1.0 equiv) of the starting pivaloate (from Step O) and 8 ml THF (over sieves). The system was cooled down to −20° C. 1.35 ml (1.0M solution in THF, 1.34 mmol, 2.2 equiv) L-Selectride solution was added dropwise into the solution. The reaction was moved to a −20° C. freezer, kept for 18 hours, and then quenched with a basic peroxide solution, containing 25% saturated aqueous sodium bicarbonate solution, 50% methanol, and 25% of the 30% $H_2O_2$ in $H_2O$ solution. The resultant mixture was warmed to 0° C. and stirred for half an hour. Ethyl acetate was added to create two phases. The organic layer was separated from the aqueous one, which was extracted with 5×10 ml ethyl acetate. The combined organic portion was washed with 2×20 ml saturated aqueous sodium bicarbonate solution, dried over anhydrous sodium sulfate, filtered, concentrated, and chromatographed on a silica gel column (3 cm ×26 cm, 3:2=hexane:ethyl acetate, with 1% distilled triethylamine) to afford 250 mg of the desired product in 84% yield: Rf=0.15 (3:2=hexane:ethyl acetate, with 1% distilled triethylamine); $^1$H NMR $\delta$5.87 (s, HC on the isoxazole ring), 4.41 (s, $CH_2OH$); $^{13}$C NMR $\delta$103.3 (HC on the isoxazole ring), 83.2 (C($C_6H_5)_3$), 56.3 ($CH_2OH$).

Step O: [3-[2-(2-Trityltetrazol-5-yl)phenyl]-5-isoxazolyl]methyl bromide

A 50 ml round-bottom flask, equipped with a magnetic stirring bar, septum, and nitrogen inlet, was charged with 250 mg (0.51 mmol, 1.0 equiv) starting alcohol (from Step P) and 8 ml methylene chloride (over sieves). The system was cooled down to 0° C. 1173 mg (3.60 mmol, 7.0 equiv) $Bu_4NBr$ was transferred into the system in one portion, followed by the addition of 450 $\mu$l (2.58 mmol, 5.0 equiv) diisopropylethylamine. 105 mg (0.57 mmol, 1.1 equiv) methanesulfonic anhydride was added into the solution, which then turned slightly yellow. The resultant solution was stirred at 0° C. for 2 minutes, and warmed up to room temperature.

After stirring at room temperature for 4.25 hours, the reaction solution was transferred onto a silica gel column (4 cm×23 cm, 3:2=hexane:ethyl acetate, 1% distilled triethylamine) without any workup. 240 mg (85% yield) of the desired product was isolated: Rf=0.57 (3:2=hexane:ethyl acetate, 1% distilled triethylamine); $^1$H NMR (in $CD_2Cl_2$) δ6.06 (s, HC on the isoxazole ring), 4.23 (s, $CH_2Br$); $^{13}$C NMR (in $CD_2Cl_2$) δ105.4 (HC on the isoxazole ring), 83.6 ($C(C_6H_5)_3$), 19.2 ($CH_2Br$).

Step R: 3-(N-tert-Butoxycarbonylamino)-N-[1-[[3-[2-(2-trityltetrazol-5-yl)phenyl]-5-isoxazolyl]methyl]-2,3,4,5-tetrahydro-2-oxo-1H-benzazepin-3(R)-yl]]-3-methylbutanamide The starting protected lactam (from Step I, 150 mg, 0.40 mmol, 1.0 equiv) was weighed in a 50 ml round-bottom flask, equipped with a magnetic stirring bar, septum, and nitrogen inlet. 2 ml DMF (over sieves) was added to make a clear solution which was then cooled down to 0° C. 16 mg (80% dispersion in mineral oil, 0.48 mmol, 1.2 equiv) sodium hydride was transferred into the solution in one portion. Hydrogen evolution occurred immediately. The resultant mixture was kept at 0° C. for 2 minutes, and warmed up to room temperature to go for 20 minutes, during which it became a clear solution. A solution of 240 mg (0.44 mmol, 1.1 equiv) of the bromide (from Step Q) in 3 ml DMF was cannulated into the deprotonated lactam solution over 5 minutes at room temperature. The solution turned light orange.

The reaction was quenched at 0° C. with saturated aqueous sodium bicarbonate solution. Ethyl acetate was added to dissolve the organics. Layers were separated, and the aqueous layer was extracted with 5×10 ml ethyl acetate. The combined organic portion was washed with 3×30 ml saturated aqueous sodium bicarbonate solution, dried over anhydrous sodium sulfate, filtered, concentrated, and chromatographed on a silica gel column (3 cm×26 cm, 1:1=hexane:ethyl acetate, 1% distilled triethylamine) to afford 340 mg (quantatative) of the desired product: Rf=0.23 (1:1=hexane:ethyl acetate, 1% distilled triethylamine); $^1$H NMR δ6.50 (d, NH), 5.94 (s, HC on the isoxazole ring), 5.24 (bs, NH), 5.05-4.97 (d, 1H in $NCH_2$, J=24.2 Hz), 4.67-4.60 (d, 1H in $NCH_2$, J=24.2 Hz), 4.50-4.30 (m, $NCHCH_2$); $^{13}$C NMR δ104.9 (HC on the isoxazole ring), 83.1 ($C(C_6H_5)_3$), 78.9 ($OC(CH_3)_3$), 60.4 ($NC(CH_3)_2$), 51.5 ($NCH_2$).

Step S: 3-Amino-N-[1-[[3-[2-(1H-tetrazol-5-yl)phenyl]-5-isoxazolyl]-methyl]-2,3,4,5-tetrahydro-2-oxo-1H-benzazepin-3(R)-yl]-3-methylbutanamide, trifluoroacetate A 25 ml round-bottom flask, equipped with a magnetic stirring bar, septum, and nitrogen inlet, was charged with 60 mg (0.07 mmol, 1.0 equiv) of the starting material (from Step R) and 2.5 ml methylene chloride. The system was cooled down to 0° C. 20 ml (0.18 mmol, 2.5 equiv) anisole was added, followed by 500 ml trifluoroacetic acid (6.49 mmol, 91.0 equiv). The solution, instantaneously turned yellow, was stirred at 0° C. for 2 minutes then at room temperature for 4.75 hours. Distilled water was added to stop the reaction, and the mixture was concentrated in vacuo. The crude material was purified on a reverse-phase silica gel column (2 cm×24 cm, 60% methanol, 40% water, 0.5% TFA; reverse-phase silica gel: LiChroprep RP-18, 40–63 μm, EM Science). 18 mg (41%) of the title compound was isolated: $^1$H NMR (in $CD_3OD$) δ6.13 (s, HC on the isoxazole ring), 5.240–5.08 (2d, $NCH_2$, J=19.4 Hz), 4.36–4.30 (dd, $HNCHCH_2$); $^{13}$C NMR (in $CD_3OD$) δ104.6 (HC on the isoxazole ring), 53.9 ($NCH_2$), 51.4 ($HNCHCH_2$), 43.9 ($COCH_2$), 35.5 ($HNCHCH_2$), 29.1 ($HNCHCH_2CH_2$); FAB-MS: calculated $C_{26}H_{29}N_8O_3$=501.6, found 501.9 (M+H, 100%).

EXAMPLE 2

3-Amino-N-[1-[[5-[2-(1H-tetrazol-5-yl)-phenyl]-2-thienyl]methyl]-2,3,4,5-tetrahydro-2-oxo-1H-1-benzazepin-3(R)-yl-3-methylbutanamide, trifluoroacetate Step A: 2-tert-Butyldimethylsilyloxymethyl-thiophene A 100 ml round-bottom flask, equipped with a magnetic stirring bar, septum, and nitrogen inlet, was charged with 500 μl (3.98 mmol, 1.0 equiv) 2-thiophenemethanol and 5 ml DMF (over sieves). This clear solution was cooled down to 0° C. 825 mg (11.95 mmol, 3.0 equiv) imidazole was added in one portion, followed by the addition of 930 mg (5.97 mmol, 1.5 equiv) t-butyl-dimethylsilyl chloride. The reaction was kept at 0° C. for 5 minutes, warmed up to room temperature to go for half an hour, and then quenched with distilled water. Ethyl acetate was added to dissolve the organics. Layers were separated, and the aqueous layer was extracted with 5×10 ml ethyl acetate. The combined organic portion was washed with 5×20 ml $H_2O$, dried over anhydrous sodium sulfate, filtered, concentrated, and chromatographed on a silica gel column (5 cm×24 cm, 100:1=hexane:ethyl acetate) to afford 1 gram of the title compound: Rf=0.26 (100:1=hexane:ethyl acetate), $^1$H NMR δ4.87 (s, $OCH_2$), 0.91 (s, tBu), 0.09 (s, $CH_3$).

Step B: 2-tert-Butyldimethylsilyloxymethyl-5-iodothiophene

A 10 ml flask, equipped with a magnetic stirring bar, septum, and nitrogen inlet, was charged with 100 mg (0.44 mmol, 1.0 equiv) of the starting material (from Step A) and 1 ml THF (over sieves). The clear solution was cooled down to −20° C. 325 μl n-butyllithium (1.56M solution in hexanes, 0.51 mmol, 1.15 equiv) was added dropwise at −20° C., and the color of the solution turned yellow. The resultant solution was stirred at −20° C. for 15 minutes, and then cannulated into the solution of 156 mg (0.66 mmol, 1.5 equiv) N-iodosuccinimide in 1 ml THF (over sieves) at −20° C., which resulted immediate yellow precipitation. The mixture was stirred at −20° C. for 30 minutes, warmed up to 0° C. for 15 minutes, and quenched with saturated aqueous ammonium chloride solution. The organic layer was separated from the aqueous one, which was then extracted with 5×5 ml ethyl acetate. The combined organic portion was washed with 2×20 ml distilled water, dried over anhydrous sodium sulfate, filtered, concentrated, and chromatographed on a silica gel column (2 cm×21 cm, 30:1=hexane:ethyl acetate) to afford 135 mg, 90% of which was the desired product, and 10% the unreacted starting material. The title compound: Rf=0.55 (30:1=hexane:ethyl acetate); $^1$H NMR (in $D_6$-acetone) δ7.17–7.15 (d, thiophene H, J=3.48 Hz), 6.71–6.69 (dd, thiophene H, J=3.48 Hz, 1.08 Hz), 4.90 (d, $OCH_2$, J=1.08 Hz).

Step C: 2-tert-Butyldimethylsilyloxymethyl-5-[2-(2-trityl-tetrazol-5-yl)phenyl]-thiophene (A) A 10 ml flask, equipped with a magnetic stirring bar, septum, and nitrogen inlet, was charged with 138 mg (0.36 mmol, 1.0 equiv) of 5-phenyl-2-trityltetrazole (from EXAMPLE 1, Step K) and 1.5 ml THF (over sieves). This clear solution was cooled down to −20° C. A few drops of n-butyllithium (1.56 m solution in hexanes) was added until a persistent red color was obtained, then 250 μl (0.39 mmol, 1.1 equiv) of it was transferred into the solution. The resultant red solution was stirred at −20° C. for 1.7 hours, and then 400 μl (1.0M solution in diethyl ether, 0.40 mmol, 1.12 equiv) $ZnCl_2$ solution was added. The color of the solution quickly faded to light yellow. The system was kept at −20° C.

(B) A solution of 23 mg (0.036 mmol, 0.1 equiv) bis(-triphenylphosphine) nickel chloride in 0.6 ml THF (over sieves) was made in a 25 ml flask and cooled down to 0° C. Into this solution was added 24 μl (3.0M solution in THF, 0.071 mmol, 0.2 equiv) of methyl magnesium chloride solution to form the activated Ni° species. A solution of the iodo compound (from Step B, 135 mg, 90% pure, 0.36 mmol, 1.0 equiv) in 1 ml THF was cannulated into the Ni° solution. The resultant solution was warmed up to room temperature.

(C) The Zn solution, from (A), was cannulated into the Ni solution, from (B), over 5 minutes. The resultant mixture was stirred at room temperature for 40 hours and then cooled back down to 0° C. 570 mg of Celite was added into the mixture, followed by a dropwise addition of 500 μl concentrated ammonium hydroxide solution to form a very thick mixture, which was stirred at room temperature for an additional hour and then filtered through a layer of Celite. The filtered solution was concentrated, redissolved in ethyl acetate, washed with 2×20 ml saturated aqueous sodium bicarbonate solution, dried over anhydrous sodium sulfate, filtered, concentrated, and chromatographed on a silica gel column (3 cm×28 cm, 35:6:1=hexane:methylene chloride:ethyl acetate, 1% distilled triethylamine) to afford 120 mg (55%) of the title compound: Rf=0.19 (35:6:1=hexane:methylene chloride:ethyl acetate, 1% distilled triethylamine); $^1H$ NMR δ6.66–6.64 (dd, 1 thiophene H), 6.59–6.57 (d, 1 thiophene H), 4.74 (d, $OCH_2$).

Step D: 2-Hydroxymethyl-5-[2-(2-trityl-tetrazol-5-yl)phenyl]-thiophene

Into a solution of 120 mg (0.20 mmol, 1.0 equiv) of the starting silyl compound (from Step C) in 2 ml THF (over sieves) in a 50 ml round-bottom flask was added 77 mg (0.29 mmol, 1.5 equiv) of tetrabutylammonium fluoride in one portion at 0° C. The resultant light yellow solution was stirred at 0° C. for 5 minutes, then warmed up to room temperature. The reaction was cooled back down to 0° C. after 30 minutes and quenched with aqueous potassium carbonate solution. Ethyl acetate was added to dissolve the organics. The organic layer was separated from the aqueous one, which was extracted with 3×10 ml ethyl acetate. The combined organic portion was washed with 2×10 ml aqueous potassium carbonate solution, dried over anhydrous sodium sulfate, filtered, concentrated, and chromatographed on a silica gel column (3 cm×25 cm, 2:1=hexane:ethyl acetate, 1% distilled triethylamine) to afford 86 mg of the desired product in 88% yield: Rf=0.24 (2:1=hexane:ethyl acetate, 1% distilled triethylamine); $^1H$ NMR δ6.72 (d, 1 thiophene H), 6.65 (d, 1 thiophene H), 4.61 (s, $HOCH_2$); $^{13}C$ NMR δ60.0 ($HOCH_2$).

Step E: 2-Bromomethyl-5-[2-(2-trityl-tetrazol-5-yl)phenyl]-thiophene

A 50 ml round-bottom flask, equipped with a magnetic stirring bar, septum, and nitrogen inlet, was charged with 86 mg (0.17 mmol, 1.0 equiv) of 2-hydroxymethyl-5-[2-(2-trityl-tetrazol-5-yl)phenyl]-thiophene (from Step D) and 3 ml methylene chloride (over sieves). Into this clear solution, after being cooled down to 0° C., was added 388 mg (1.20 mmol, 7.0 equiv) tetrabutylammonium bromide, 150 μl (0.86 mmol, 5.0 equiv) diisopropylethylamine, and 37 mg (0.19 mmol, 1.1 equiv) methanesulfonic anhydride. The resultant light yellow solution was stirred at 0° C. for 4 minutes, and then warmed up to room temperature. A second batch of reagents ($Bu_4NBr$:1.5 equiv, amine:2.0 equiv, MsOMs:0.6 equiv) was added after 1.25 hours at room temperature to push the reaction to completion.

The reaction solution was transferred directly on a silica gel column (3 cm×25 cm, 2:1=hexane:ethyl acetate, 1% distilled triethylamine) without any workup after 4.25 hours. 52 mg of the title compound was isolated in 54% yield: Rf: 0.55 (2:1=hexane:ethyl acetate, 1% distilled triethylamine); $^1H$ NMR (in $D_6$-acetone) δ7.03 (d, 1 thiophene H), 6.68 (d, 1 thiophene H), 4.82 (s, $BrCH_2$); $^{13}C$ NMR (in $D_6$-acetone) δ28.5 ($BrCH_2$).

Step F: 3-(N-tert-Butoxycarbonylamino)-N-[1-[[5-[2-(2-trityl-tetrazol-5-yl)-phenyl]-2-thienyl]methyl]-2,3,4,5-tetrahydro-2-oxo-1H-1-benzazepin-3(R)-yl-3-methylbutanamide A solution of 32 mg (0.084 mmol, 1.0 equiv) of the starting protected lactam (from EXAMPLE 1, Step I) in 500 μl DMF (over sieves), in a 10 ml flask, was cooled down to 0° C. Into this clear solution was added 4 mg (0.11 mmol, 1.2 equiv) of sodium hydride as an 80% dispersion in mineral oil. The resulting mixture was stirred at room temperature for 30 minutes, during which the mixture became a clear solution. The solution of 52 mg (0.092 mmol, 1.1 equiv) of the bromide (from Step E) in 2 ml DMF was cannulated into the deprotonated lactam solution over 5 minutes at 0° C. The resultant yellow solution was warmed up to room temperature to go for 30 minutes, then quenched with saturated aqueous sodium bicarbonate solution. Ethyl acetate was added to dissolve the organics. Layers were separated, and 4×5 ml ethyl acetate was used to extract the aqueous layer. The combined organic portion was washed with saturated aqueous sodium bicarbonate solution, dried over anhydrous sodium sulfate, filtered, concentrated, chromatographed on a silica gel column (3 cm×25 cm, 6:5=hexane:ethyl acetate, 1% distilled triethylamine) to afford 61 mg (84%) of the desired product: Rf=0.25 (6:5=hexane:ethyl acetate, 1% distilled triethylamine); $^1H$ NMR δ6.55 (d, thiophene H), 6.49 (d, thiophene H), 5.38 (d, 1H in $NCH_2$, J=15.1 Hz), 4.62 (d, 1H in $NCH_2$, J=15.1 Hz), 4.42 (m, $CH_2CHNH$); $^{13}C$ NMR δ83.0 ($C(Ph)_3$), 51.6 ($NCH_2$), 49.4 ($CH_2CHNH$), 46.8 ($COCH_2$), 36.2 ($CH_2CHNH$).

Step G: 3-Amino-N-[1-[[5-[2-(1H-tetrazol-5-yl)-phenyl]-2-thienyl]methyl]-2,3,4,5-tetrahydro-2-oxo-1H-1-benzazepin-3(R)-yl-3-methylbutanamide, trifluoroacetate A solution of 61 mg (0.071 mmol, 1.0 equiv) of the starting compound (from Step F) in 3 ml methylene chloride (over sieves) was cooled down to 0° C. Into this chilled solution was added 20 μl anisole (0.18 mmol, 2.5 equiv) and 500 μl trifluoroacetic acid. The resultant bright yellow solution was stirred at 0° C. for 2 minutes, then warmed up to room temperature. The reaction was quenched after 3 hours with the addition of distilled water. This mixture, concentrated in vacuo, was purified on a reverse-phase RP-18 column (2 cm×24 cm, 60% methanol, 40% water, 0.5% TFA; reverse-phase LiChroprep RP-18, 40–63 μm, EM Science). 41 mg (93%) of the title compound was isolated: $^1$H NMR (in CD$_3$OD) δ6.77 (d, 1H thiophene H, J=4.8 Hz), 6.73 (d, 1H thiophene H, J=4.8 Hz), 5.49 (d, 1H in NCH$_2$, J=15.1 Hz), 4.86 (1H in NCH$_2$, J=15.1 Hz), 4.35 (dd, HNCHCH$_2$); $^{13}$C NMR (in CD$_3$OD) δ55.6 (CH$_2$C(CH$_3$)$_2$), 52.7 (NCHCH$_2$), 49.1 (NCH$_2$), 45.7 (COCH$_2$), 37.6 (HNCHCH$_2$), 30.9 (HNCHCH$_2$CH$_2$); FAB-MS: calculated C$_{27}$H$_{30}$N$_7$O$_2$S=516.2, found 516.9 (M+H, 100%).

EXAMPLE 3

3-Amino-N-[1-[4-(3-thienyl)benzyl]-2,3,4,5-tetrahydro-2-oxo-1H-1-benzazepin-3(R)-yl]-3-methylbutanamide, trifluoroacetate Step A: O-tert-Butyldimethylsilyl-4-bromobenzyl alcohol Into a 50 ml round-bottom flask, equipped with a magnetic stirring bar, septum, and nitrogen inlet, was added 600 mg (3.20 mmol, 1.0 equiv) of 4-bromobenzyl alcohol and 5 ml DMF (over sieves). The solution was cooled down to 0° C. 350 mg (5.13 mmol, 1.6 equiv) imidazole and 650 mg (4.17 mmol, 1.3 equiv) tert-butyldimethylsilyl chloride were added. The resultant solution was stirred at 0° C. for 5 minutes, 45 minutes at room temperature, cooled down to 0° C., and quenched with distilled water. Ethyl acetate was added to dissolve the organics. Layers were separated, and 5×10 ml ethyl acetate was used to extract the aqueous layer. The combined organic portion was washed with 3×30 ml distilled water and 30 ml brine, dried over anhydrous sodium sulfate, filtered, concentrated, and chromatographed on a silica gel column (4 cm×28 cm, 35:6:1=hexane:methylene chloride:ethyl acetate) to afford 966 mg (quantatative) of the title compound: Rf=0.53 (35:6:1=hexane:methylene chloride:ethyl acetate); $^1$H NMR δ7.43–7.41 (d, J=8.6 Hz), 7.19–7.16 (d, J=8.6 Hz), 4.66 (s, OCH$_2$), 0.91 (s, tBu), 0.07 (s, CH$_3$).

Step B: 3-(4-tert-Butyldimethylsilyloxymethylphenyl)thiophene

Into a solution of 570 mg (1.89 mmol, 1.0 equiv) of O-tert-butyldimethylsilyl-4-bromobenzyl alcohol (from Step A) in 9 ml THF (over sieves) was added 52 mg Mg metal and a few pieces of I$_2$. The system was purged with nitrogen, brought up to reflux for 5 hours, and then cooled back down to room temperature. A mixture of 180 μl (1.89 mmol, 1.0 equiv) 3-bromothiophene, 120 mg (0.22 mmol, 0.12 equiv) [1,3-bis(diphenyl-phosphino)propane]nickel(II) chloride, and 2 ml THF was cannulated into the Grignard solution. The resultant black mixture was kept at reflux for 19 hours and then quenched with distilled water. Ethyl acetate was added, and layers were separated. The aqueous layer was extracted with 7×10 ml ethyl acetate, and the combined organic portion was washed with 3×25 ml brine, dried over anhydrous sodium sulfate, filtered, concentrated, and chromatographed on a silica gel column (5 cm×25 cm, 80:10:1=hexane:methylene chloride:ethyl acetate) to afford some clean product. The mixture from the first column was repurified on prep-TLC plates (5×1000 μm, 70:10:1=hexane:methylene chloride:ethyl acetate), and the two batches of the desired product were combined to give 235 mg (41%) of the title compound: Rf=0.32 (70:10:1=hexane:methylene chloride:ethyl acetate); $^1$H NMR δ7.58–7.55 (d, J=8.1 Hz), 7.43 (t), 7.38–7.33 (m), 4.76 (s, OCH$_2$).

Step C: 3-(4-Hydroxymethyl-phenyl)thiophene

Using the same procedure as Step D, EXAMPLE 2, 80 mg 3-(4-tert-butyldimethylsilyloxymethyl-phenyl)-thiophene (from Step B) was converted to 3-(4-hydroxymethyl-phenyl)thiophene (40 mg, 80% yield): Rf=0.25 (2:1=hexane:ethyl acetate); $^1$H NMR δ7.59–7.56 (d, J=9.1 Hz), 7.43 (t), 7.39–7.33 (m), 4.69 (s, OCH$_2$).

Step D: 3-(4-Bromomethyl-phenyl)thiophene

Using the same procedure as Step Q, EXAMPLE 1, 47 mg (88% yield) of the title compound was obtained from 40 mg of 3-(4-hydroxymethyl-phenyl)thiophene (from Step C): Rf=0.59 (4:1=hexane:ethyl acetate); $^1$H NMR (in CD$_2$Cl$_2$) δ4.55 (s, BrCH$_2$).

Step E: 3-(N-tert-Butoxycarbonylamino)-N-[1-[4-(3-thienyl)benzyl]-2,3,4,5-tetrahydro-2-oxo-1H-1-benzazepin-3(R)-yl]-3-methylbutanamide Using the same procedure as Step R, EXAMPLE 1, 94 mg (99% yield) of the title compound was isolated from the reaction of 47 mg 3-(4-bromomethyl-phenyl)thiophene (from Step D) with 64 mg of the protected benzolactam (from Step I, EXAMPLE 1): Rf=0.29 (1:1=hexane:ethyl acetate); $^1$H NMR δ6.69 (d, NH), 5.24 (d, J=15.3 Hz, 1H in NCH$_2$), 4.80 (d, J=15.3 Hz, 1H in NCH$_2$), 4.49 (m, COCHNH).

Step F: 3-Amino-N-[1-[4-(3-thienyl)benzyl]-2,3,4,5-tetrahydro-2-oxo-1H-1-benzazepin-3(R)-yl]-3-methylbutanamide, trifluoroacetate Using the same procedure as Step S, EXAMPLE 1, 95 mg 3-(N-tert-butoxycarbonylamino)-N-[1-[4-(3-thienyl)benzyl]-2,3,4,5-tetrahydro-2-oxo-1H-1-benzazepin-3(R)-yl]-3-methylbutanamide (from Step E) was deprotected to afford 89 mg (91%) of the title compound: $^1$H NMR (in CD$_3$OD) δ5.22–5.14 (d, J=31.5 Hz, 1H in NCH$_2$), 4.81–4.73 (d, J=31.5 Hz, 1H in NCH$_2$), 4.34–4.23 (dd, J=24.2 Hz, 23.4 Hz, COCHNH); $^{13}$C NMR (in CD$_3$OD) δ54.0 (CH$_2$C(CH$_3$)$_2$), 52.5 (NCH$_2$), 51.4 (HNCHCH$_2$), 44.2 (COCH$_2$), 35.9 (HNCHCH$_2$), 29.1 (HNCHCH$_2$CH$_2$); FAB-MS: calculated C$_{26}$H$_{30}$N$_3$O$_2$S=448.6, found 448.4 (M+H, 100%).

EXAMPLE 4

3-Amino-N-[1-[4-[2-(1H-tetrazol-5-yl)-3-thienyl]-benzyl]-2,3,4,5-tetrahydro-2-oxo-1H-1-benzazepin-3(R)-yl]-3-methylbutanamide, trifluoroacetate Step A: Tributyltin azide Into 40 ml of distilled water was added 9.99 g of sodium azide (0.154 mol, 10.0 equiv), 30 ml tert-butyl methyl ether, and 5.0 g (0.0154 mol, 1.0 equiv) tributyltin chloride. The resultant mixture was stirred at room temperature for one hour. Carbon 13 NMR of an aliquot taken at this point showed absence of the starting tributyltin chloride. Therefore, the organic layer, after being separated from the aqueous layer, was dried over anhydrous sodium sulfate, filtered, concentrated, and distilled to afford 3.29 g (65%) of the desired product (bp.=115°–117° C./0.4 mm): $^{13}$C NMR δ27.8, 27.0, 15.2, 13.6.

Step B: 2-(2-Trityl-tetrazol-5-yl)-3-bromothiophene

A 25 ml flask, equipped with a magnetic stirring bar, rubber septum, and nitrogen inlet, was charged with 801 mg (4.26 mmol, 1.0 equiv) of 2-cyano-3-bromothiophene, 10 ml xylene (over sieves), and 1.44 ml (5.32 mmol, 1.25 equiv) tributyltin azide (from Step A). The reaction was stirred at 140° C. for 17.5 hours, and the reaction mixture was diluted with hexane and methylene chloride. 2.5N aqueous sodium hydroxide was used to extract the organic portion several times, and the combined NaOH was acidified down to pH=0 with concentrated hydrochloric acid. Methylene chloride was subsequently used to extract the tetrazole compound out of the acidic aqueous solution. The combined organic portion was dried over anhydrous sodium sulfate, filtered, and concentrated to give 1 g of the crude material.

The crude was suspended in 50 ml methylene chloride (over sieves). Into this suspension was added 4 ml (28.4 mmol, 6.7 equiv) freshly distilled triethylamine, and a clear solution was resulted. 2.42 g (8.52 mmol, 2.0 equiv) triphenylmethyl chloride was added into the clear solution in one portion. The tritylation reaction was stirred at room temperature for 1.3 hours, and quenched with saturated aqueous sodium bicarbonate solution. Ethyl acetate was added to dissolve the organics. Layers were separated, and ethyl acetate was used to extract the aqueous layer. The combined organic portion was washed with saturated aqueous sodium bicarbonate solution, dried over anhydrous sodium sulfate, filtered, concentrated, and chromatographed on a silica gel column (6 cm×31 cm, 35:6:1=hexane:methylene:ethyl acetate, 1% distilled triethylamine) to afford 1.75 g of clean product and 2.42 g of mixture, which was rechromatographed (6 cm×31 cm, 35:6:1=hexane:methylene:ethyl acetate, 1% distilled triethylamine). Altogether, 2.05 g (quantatative) of the title compound was isolated: Rf=0.27 (35:6:1=hexane:methylene:ethyl acetate, 1% distilled triethylamine); FAB-MS: calculated $C_{24}H_{17}N_4SBr=473.4$, found 479.6 (M+Li, 25%), 480.6 (M+Li, 22%), 243.1 (trityl, 100%).

Step C: 2-(2-Trityl-tetrazol-5-yl)-3-(4-tert-butyldimethylsilyloxymethylphenyl)thiophene Using the same procedure as Step B, EXAMPLE 3, the title compound was obtained from the reaction of 2-(2-trityl-tetrazol-5-yl)-3-bromothiophene with O-tert-butyldimethylsilyl-4-bromobenzyl alcohol (from Step A, EXAMPLE 3): Rf=0.16 (35:6:1=hexane:methylene:ethyl acetate, 1% distilled triethylamine); $^1$H NMR $\delta$4.76 (s, $OCH_2$).

Step D: 2-(2-Trityl-tetrazol-5-yl)-3-(4-hydroxymethylphenyl)thiophene

Using the same procedure as Step D, EXAMPLE 2, 41 mg (15% combined yield for Step C and Step D) of the title compound was isolated: Rf=0.20 (2:1=hexane:ethyl acetate, 1% distilled triethylamine); $^1$H NMR $\delta$4.66 (s, $OCH_2$).

Step E: 2-(2-Trityl-tetrazol-5-yl)-3-(4-bromomethylphenyl)thiophene

Using the same procedure as Step Q, EXAMPLE 1, 67 mg of 2-(2-trityl-tetrazol-5-yl)-3-(4-hydroxymethylphenyl)thiophene (from Step D) was converted to 62 mg (82%) of the title compound: Rf=0.58 (2:1=hexane:ethyl acetate, 1% distilled triethylamine); $^1$H NMR (in $CD_2Cl_2$) $\delta$4.53 (s, $BrCH_2$); $^{13}$C NMR (in $CD_2Cl_2$) $\delta$33.8 ($BrCH_2$).

Step F: 3-(N-tert-Butoxycarbonylamino)-N-[1-[4-[2-(2-trityltetrazol-5-yl)-3-thienyl]-benzyl]-2,3,4,5-tetrahydro-2-oxo-1H-1-benzazepin-3(R)-yl]-3-methylbutanamide Using the same procedure as Step R, EXAMPLE 1, 81 mg (93% yield) of the title compound was isolated from the reaction of 62 mg 2-(2-trityl-tetrazol-5-yl)-3-(4-bromomethyl-phenyl)thiophene (from Step E) with 38 mg of the protected benzolactam (from Step I, EXAMPLE 1): Rf=0.27 (1:1=hexane:ethyl acetate, 1% distilled triethylamine); $^1$H NMR $\delta$6.71 (d, NH), 5.36 (s,NH), 5.15–5.10 (d, J=15.1 Hz, 1H in $NCH_2$), 4.86–4.81 (d, J=15.1 Hz, 1H in $NCH_2$), 4.50 (m, $NHCHCH_2$), $^{13}$C NMR $\delta$52.0 ($NCH_2$), 49.6 ($HNCHCH_2$), 46.7 ($COCH_2$), 36.3 ($HNCHCH_2$), 28.2 ($HNCHCH_2CH_2$).

Step G: 3-Amino-N-[1-[4-[2-(1H-tetrazol-5-yl)-3-thienyl]-benzyl]-2,3,4,5-tetrahydro-2-oxo-1H-1-benzazepin-3(R)-yl]-3-,ethylbutanamide, trifluoroacetate Using the same procedure as Step S, EXAMPLE 1, 81 mg 3-(N-tert-butoxycarbonylamino)-N-[1-[4-[2-(2-trityltetrazol-5-yl)-3-thienyl]-benzyl]-2,3,4,5-tetrahydro-2-oxo-1H-1-benzazepin-3(R)-yl]-3-methyl-butanamide (from Step F) was deprotected to afford 32 mg (54%) of the title compound: $^1$H NMR (in $CD_3OD$) $\delta$5.22–5.16 (d, J=15.7 Hz, 1H in $NCH_2$), 4.47–4.41 (dd, COCHNH); $^{13}$C NMR (in $CD_3OD$) $\delta$55.6 ($CH_2C(CH_3)_2$), 54.4 ($NCH_2$), 53.1 ($HNCHCH_2$), 45.7 ($COCH_2$), 37.5 ($HNCHCH_2$), 30.8 ($HNCHCH_2CH_2$); FAB-MS: calculated $C_{27}H_{30}N_7O_2S=516.7$, found 516.6 (M+H, 95%).

EXAMPLE 5

3-[2(R)-Hydroxypropyl]amino-N-[1-[4-[2-(1H-tetrazol-5-yl)-3-thienyl]benzyl]-2,3,4,5-tetrahydro-2-oxo-1H-1-benzazepin-3(R)-yl]-3-methylbutanamide, trifluoroacetate Step A: 3-Amino-3-methyl-N-[2,3,4,5-tetrahydro-2-oxo-1H-1-benzazepin-3(R)-yl]-butanamide, trifluoroacetate To a solution of 150 mg (0.40 mmol) of 3-t-butoxycarbonylamino-3-methyl-N-[2,3,4,5-tetrahydro-2-oxo-1H-1-benzazepin-3(R)-yl]-butanamide (Example 1, Step I) in 2 mL of methylene chloride at 0° C. was added 2 mL of trifluoroacetic acid and the mixture stirred at room temperature for 1 hour. All volatiles were removed under vacuum to give 130 mg (0.33 mmol, 84%) of the product.

$^1$H NMR (200 MHz, $CD_3OD$): $\delta$1.33 (s, 3H), 1.37 (s, 3H), 2.12 (m, 1H), 2.3–2.6 (m, 3H), 2.6–3.0 (m, 2H), 4.37 (dd; 8, 12 Hz; 1H), 7.02 (d, 8 Hz, 1H), 7.1–7.3 (m, 3H).

FAB-MS: calculated for $C_{15}H_{21}N_3O_2$ 275; found 276 (M+H, 100%).

Step B: 3-[2(R)-Benzyloxypropyl]amino-3-methyl-N-[2,3,4,5-tetrahydro-2-oxo-1H-1-benzazepin-3(R)-yl]-butanamide, trifluoroacetate To a solution of 1.0 g (2.57 mmol) of 3-amino-3-methyl-N-[2,3,4,5-tetrahydro-2-oxo-1H-1-benzazepin-3(R)-yl]-butanamide, trifluoroacetate in 25 mL of dry methanol was added 3.0 g of dry 3 A powdered molecular sieves followed by a solution of 2.5 g (17 mmol) of (R)-2-benzyloxypropanol (prepared from ethyl-D-lactate according to the procedure of Hanessian and Kloss, Tetrahedron Lett. 1985, 26, 1261–1264.) in 5 mL of dry methanol. The pH of the mixture was carefully adjusted to 6 by the addition of trifluoroacetic acid. The reaction was stirred for 2 hours at room temperature at which time 15.4 mL (15.4 mmol) of a 1.0M solution of sodium cyanoborohydride in tetrahydrofuran was added by syringe. The reaction was stirred for 72 hours then filtered through a pad of Celite. To the filtrate was added 5 mL of trifluoroacetic acid (CAUTION! evolution of hydrogen cyanide) and the resulting mixture was stirred for three hours. The solvent was removed under vacuum to afford a clear oil which was purified by reverse phase medium pressure liquid chromatography on C-8, eluting with methanol/0.1% aqueous trifluoroacetic acid (60:40), to afford 1.27 g (2.36 mmol, 92%) of the product as a white solid. $^1$H NMR (200 MHz, CD$_3$OD): δ1.31 (d, 6 Hz, 3H), 1.40 (s, 3H), 1.43 (s, 3H), 2.17 (m, 1H), 2.30 (m, 1H), 2.6–3.1 (m, 5H), 3.22 (dd; 3, 12 Hz; 1H), 3.86 (m, 1H), 4.48 (dd; J, 12 Hz; 1H), 4.50 (d, 12 Hz, 1H), 4.70 (d, 12 Hz, 1H), 7.11 (d, 8 Hz, 1H), 7.15–7.45 (m, 8H). FAB-MS: calculated for C$_{25}$H$_{33}$N$_3$O$_3$ 423; found 424 (M+H, 100%).

Step C: 3-[2(R)-Benzyloxypropyl]amino-3-methyl-N-[2,3,4,5-tetrahydro-2-oxo-1H-1-benzazepin-3(R)-yl]-butanamide To a solution of 2.034 g (3.788 mmol) of the intermediate obtained in Step B in 40 mL of methylene chloride was added 40 mL of water. The mixture was stirred vigorously while sufficient solid potassium carbonate was added to adjust the pH of the aqueous layer to 10–11. Stirring was discontinued and the layers allowed to separate. The organic layer was removed and the aqueous layer extracted twice more with methylene chloride. The combined extracts were dried over potassium carbonate, filtered and solvents removed under vacuum to afford 1.53 g (3.62 mmol, 95%) of the product as a white solid.

Step D: 2-(2-Trityl-tetrazol-5-yl)-3-(4-tert-butyldimethylsilyloxymethylphenyl)thiophene Into a 10 ml flask, equipped with a magnetic stirring bar, septum, and nitrogen inlet, was added 96 mg (0.32 mmol, 1.5 equiv) of O-tert-butyldimethylsilyl-4-bromobenzyl alcohol (from Step A, EXAMPLE 3), 1 ml THF (over sieves), 9 mg (0.36 mmol, 1.7 equiv) magnesium metal, and a few I$_2$ crystals. The system was kept under reflux for 4.5 hours to obtain complete Grignard formation. Then the Grignard solution was cannulated into a suspension of 100 mg (0.21 mmol, 1.0 equiv) of 2-(2-trityl-tetrazol-5-yl)-3-bromothiophene (from Step B, EXAMPLE 4) and 12 mg (0.021 mmol, 0.1 equiv) [1,3-bis(-diphenylphosphino)propane]nickel(II) chloride in 2 ml THF. The resultant suspension, turning brown within minutes, was stirred at room temperature for half an hour, then quenched with saturated aqueous sodium bicarbonate solution. Ethyl acetate was added to dissolve the organics, and layers were separated. The aqueous layer was extracted with 5×10 ml ethyl acetate, and the combined organic portion was washed with saturated aqueous sodium bicarbonate solution, dried over anhydrous sodium sulfate, filtered, concentrated, and chromatographed on a silica gel column (3 cm×30 cm, 35:6:1 = hexane:methylene chloride:ethyl acetate, 1% distilled triethylamine) to afford 100 mg (77%) of the title compound. (for analytical data, see Step C, EXAMPLE 4)

Step E: 2-(2-Trityl-tetrazol-5-yl)-3-(4-hydroxymethylphenyl)thiophene

Using the same procedure as Step D, EXAMPLE 2, 185 mg of the title compound was obtained from 379 mg of 2-(2-trityl-tetrazol-5-yl)-3-(4-tert-butyldimethylsilyloxymethyl-phenyl)thiophene (from Step D). (for analytical data, see Step D, EXAMPLE 4)

Step F: 2-(2-Trityl-tetrazol-5-yl)-3-(4-bromomethylphenyl)thiophene

Using the same procedure as Step Q, EXAMPLE 1, 185 mg of 2-(2-trityl-tetrazol-5-yl)-3-(4-hydroxymethylphenyl)thiophene (from Step E) was converted to 160 mg (77%) of the title compound. (for analytical data, see Step E, EXAMPLE 4)

Step G: 3-[2(R)-Benzyloxypropyl]amino-N-[1-[4-[2-(2-trityl-tetrazol-5-yl)-3-thienyl]-benzyl]-2,3,4,5-tetrahydro-2-oxo-1H-1-benzazepin-3(R)-yl]-3-methyl-butanamide A flask, equipped with a magnetic stirring bar, septum, and nitrogen inlet, was charged with 132 mg (0.31 mmol, 1.1 equiv) of the protected lactam (from Step C) and 1 ml DMF (over sieves). Into this clear solution, after being chilled to 0° C., was added 12 mg (80% dispersion in mineral oil, 0.37 mmol, 1.3 equiv) sodium hydride in one portion. Hydrogen evolution occurred immediately. The resultant mixture was stirred at 0° C. for two minutes, then warmed up to room temperature to go for 30 minutes, during which the mixture became a homogeneous solution.

A solution of 160 mg (0.28 mmol, 1.0 equiv) 2-(2-trityl-tetrazol-5-yl)-3-(4-bromomethyl-phenyl)thiophene (from Step F) in 1 ml DMF (over sieves) was cannulated into the deprotonated lactam solution. The resultant yellow solution was stirred at room temperature for 30 minutes and quenched with saturated aqueous sodium bicarbonate solution. Ethyl acetate was added to dissolve the organics, and layers were separated. The aqueous layer was extracted with 5×10 ml ethyl acetate, and the combined organic portion was washed with saturated aqueous sodium bicarbonate solution, dried over anhydrous sodium sulfate, filtered, concentrated, and chromatographed on a silica gel column (3 cm×22 cm, 90:4:1 = chloroform:methanol:concentrated ammonium hydroxide solution) to afford 256 mg (96%) of the desired product: Rf=0.29 (3 cm×22 cm, 90:4:1 = chloroform:methanol:concentrated ammonium hydroxide solution); $^1$H NMR δ5.13–5.07 (d, J=15.1 Hz, 1H in NCH$_2$), 4.91–4.86 (d, J=15.1 Hz, 1H in NCH$_2$), 4.63–4.50 (m, OCH$_2$Ph & NHCHCH$_2$), 3.92–3.80 (m, NCH$_2$CHCH$_3$), $^{13}$C NMR δ70.8 (OCH$_2$Ph), 51.8 (NCH$_2$), 49.6 (HNCHCH$_2$), 36.2 (HNCHCH$_2$), 28.5 (HNCHCH$_2$CH$_2$).

Step H: 3-[2(R)-Hydroxypropyl]amino-N-[1-[4-[2-(1H-tetrazol-5-yl)-3-thienyl]-benzyl]-2,3,4,5-tetrahydro-2-oxo-1H-1-benzazepin-3(R)-yl]-3-methylbutanamide, trifluoroacetate Into a 50 ml round-bottom flask was added 200 mg of the starting compound (from Step G) and 2 ml 30% HBr in acetic acid at 0° C. The resultant yellow solution was stirred at 0° C. for 2 minutes, warmed up to room temperature to go for 2.7 hours, and then concentrated under high vacuum to pump off any trace of acid. The concentrated crude was redissolved in 5 ml (1N) sodium methoxide in methanol solution at room temperature. The methanolic solution was stirred at room temperature for 50 minutes and then quenched with a mixture of methanol, water, and TFA. The resulting mixture was concentrated in vacuo and chromatographed on a reverse-phase silica gel column (3 cm×25 cm, 65% methanol, 35% water, 0.5% TFA; reverse-phase silica gel: LiChroprep RP-18, 40–63 mm, EM Science) and a Lobar column (size B, LiChroprep, RP-8. 40–63 μm, EM Science) to afford 115 mg (76%) of the title compound: $^1$H NMR (in CD$_3$OD) δ4.46–4.39 (dd, COCHNH), 4.03–3.90 (m, NCH$_2$CHCH$_3$); $^{13}$C NMR (in CD$_3$OD) δ52.8 (NCH$_2$), 51.5 (HNCHCH$_2$), 42.1 (COCH$_2$), 35.6 (HNCHCH$_2$), 29.1 (HNCHCH$_2$CH$_2$).

EXAMPLE 6

3-Amino-N-[1-[[4-[2-(1H-tetrazol-5-yl)-phenyl]-cyclohexyl]methyl]-2,3,4,5-tetrahydro-2-oxo-1H-1-benzazepin-3(R)-yl]-3-methylbutanamide, trifluoroacetate Step A: 8-[2-[2-Trityl-2H-tetrazol-5-yl]phenyl]-1,4-dioxaspiro[4.5]decan-8-ol (A) A 250 ml round-bottom flask, equipped with a magnetic stirring bar, septum, and a nitrogen inlet, was charged with the 6.37 g (16.4 mmol, 1.1 equiv) 5-phenyl-2-trityltetrazole (from Step K, EXAMPLE 1) and 130 ml THF (over sieves). Into this clear solution, having been cooled down to −25° C., was added a few drops of n-butyllithium until a persistent red color was observed. Then 12.3 ml (1.58M solution in hexanes, 19.39 mmol, 1.3 equiv) was added dropwise. The resultant red solution was stirred at −25° C. for two hours.

(B) A solution of 2.33 g (14.92 mmol, 1.0 equiv) 1,4-cyclohexanedione-mono-ethylene ketal in 10 ml THF was cannulated into the solution from (A). The red color gradually faded. The resultant solution was stirred at −25° C. for 30 minutes, 1.25 hours at 0° C., and quenched with saturated aqueous ammonium chloride solution. Ethyl acetate was added to dissolve the organics, and layers were separated. The aqueous layer was extracted with 6×20 ml ethyl acetate, and the combined organic portion was washed with 2×30 ml saturated aqueous sodium bicarbonate solution, dried over anhydrous sodium sulfate, filtered, concentrated, and chromatographed on a silica gel column (6 cm×26 cm, 2:1=hexane:ethyl acetate, 1% distilled triethylamine) to afford 6.63 g (82%) of the title compound: Rf=0.29 (2:1=hexane:ethyl acetate, 1% distilled triethylamine); $^1$H NMR $\delta$4.93 (s, OH), 3.99–3.85 (m, 4H in OCH$_2$CH$_2$O).

Step B: 5-[2-(1,4-Dioxaspiro[4.5]dec-7-en-8-yl)phenyl]-2-trityl-2H-tetrazole

Into a 250 ml round-bottom flask was added 5.5 g (10.11 mmol, 1.0 equiv) of the starting alcohol (from Step A) and 44 ml (546 mmol, 54 equiv) of pyridine (over sieves). After the system was cooled down to 0° C., 9 ml (123 mmol, 12 equiv) thionyl chloride was added dropwise. The reaction was stirred at 0° C. for 25 minutes and slowly transferred into 100 ml of 1.25N aqueous sodium hydroxide solution. Methylene chloride was added to dissolve the organic material. Layers were separated, and the aqueous layer was extracted with 7×20 ml methylene chloride. The combined organic portion was washed with 2×40 ml saturated aqueous ammonium chloride solution, dried over anhydrous sodium sulfate, filtered, and concentrated in vacuo. Toluene was used to azeotrope off the residual pyridine in the crude mixture, which was then chromatographed on a silica gel column (6 cm×27 cm, 5:1=hexane:ethyl acetate, 1% distilled triethylamine) to afford 3.86 g (73%) of the desired product: Rf=0.22 (5:1=hexane:ethyl acetate, 1% distilled triethylamine); $^1$H NMR $\delta$5.36–5.32 (dd, C=CHCH$_2$), 3.90–3.84 (m, 4H in OCH$_2$CH$_2$O).

Step C: 5-[2-(1,4-Dioxaspiro[4.5]decan-8-yl)phenyl]-2-(trityl)-2H-tetrazole

A 100 ml round-bottom flask, equipped with a magnetic stirring bar, septum, and nitrogen inlet, was charged with 2.5 g (4.75 mmol, 1.0 equiv) of the starting olefin compound (from Step B), 35 ml ethyl acetate (over sieves), and 3 g of palladium on activated carbon (palladium content 5%, 1.426 mmol, 0.3 equiv). The system was evacuated and flushed with hydrogen several times. Finally, a hydrogen balloon was attached to the system, and the reaction was stirred at room temperature for 4 hours. The reaction mixture was filtered through a layer of Celite, and then concentrated to afford 2.3 g of the crude, which would be carried to the next reaction without any purification. $^1$H NMR of the crude $\delta$3.95 (s, 2H in OCH$_2$CH$_2$O), 3.92 (s, 2H in OCH$_2$CH$_2$O), 3.12–3.02 (m, CH$_2$CHCH$_2$).

Step D: 1-[2-(2-Trityl-tetrazol-5-yl)phenyl]-cyclohexan-4-one (A) The crude mixture from Step C was dissolved in 10 ml THF. Into this clear solution, cooled down to 0° C., was added 20 ml 5N HCl solution. The resultant mixture was stirred at 0° C. for 5 minutes and warmed up to room temperature to go for 2 hours. Ethyl acetate was added into the mixture, which was then concentrated in vacuo to reduce the bulk of THF. Layers were separated, and ethyl acetate was used to extract the aqueous layer ten times. The combined organic portion was dried over anhydrous sodium sulfate, concentrated, and pumped with high vacuum to get rid of residual acid.

(B) The crude from (A) was suspended in 20 ml methylene chloride (over sieves). The bright yellow suspension was cooled down to 0° C., and 10 ml (71.7 mmol, 15 equiv) freshly distilled triethylamine was added, which resulted in instantaneous disappearance of the yellow color, followed by the one-portion addition of 5.9 g (21.4 mmol, 4.5 equiv) of triphenylmethyl chloride. The tritylation reaction was quenched after 30 minutes with saturated aqueous sodium bicarbonate solution. Layers were separated, and the aqueous layer was extracted with 6×20 ml methylene chloride. The combined organic portion was washed with saturated aqueous sodium bicarbonate solution, dried over anhydrous sodium sulfate, filtered, concentrated, and chromatographed on a silica gel column (6 cm×30 cm, 5:1=hexane:ethyl acetate, 1% distilled triethylamine) to afford 1.8 g (78%) of the title compound: Rf=0.24 (5:1=hexane:ethyl acetate, 1% distilled triethylamine), $^1$H NMR $\delta$3.62–3.53 (tt, CH$_2$CHCH$_2$), 2.27–2.21 (dd, 2H), 2.12–2.04(m, 2H), 1.98–1.88 (dt, 2H), 1.87–1.78 (dt, 2H); $^{13}$C NMR $\delta$163.9 (CO), 41.2, 38.6, 33.4.

Step E: [(4-Chlorophenoxy)methyl]triphenylphosphonium chloride

Into a 100 ml round-bottom flask was added 5 g (28.8 mmol, 1.0 equiv) of α,4-dichloroanisole, 7.8 g (30 mmol, 1.05 equiv) triphenylphosphine, and 50 ml toluene (over sieves). The resulting solution was heated to 100° C. for 24 hours, cooled down to room temperature, and filtered to afford the product as a white solid.

Step F: 5-[2-[4-[(4-Chlorophenoxy)methylene]cyclohexyl]phenyl]-2-trityl-2H-tetrazole (A) Into a 100 ml round-bottom flask, equipped with a magnetic stirring bar, septum, and nitrogen inlet, was charged with 590 mg (1.3 mmol, 1.3 equiv) of the phosphonium salt (from Step E) and 12 ml THF (over sieves). Into the resultant white suspension, after being cooled down to 0° C., was added 1.6 ml (1.0M solution in THF, 1.6 mmol, 1.6 equiv) lithium bis(trimethylsilyl)amide solution dropwise. The white suspension turned into a bright orange solution, which was stirred at room temperature to achieve complete ylide formation.

(B) A solution of 484 mg (1.0 mmol, 1.0 equiv) of 1-[2-(2-trityl-tetrazol-5-yl)phenyl]-cyclohexan-4-one (from Step D) in 10 ml THF was cannulated into the ylide solution from (A) at 0° C. The resultant solution was stirred at 0° C. for 10 minutes, 2.3 hours at room temperature, and quenched with saturated aqueous ammonium chloride solution. Ethyl acetate was added to dissolve the organics. Layers were separated, and the aqueous layer was extracted with 5×20 ml ethyl acetate. The combined organic portion was dried over anhydrous sodium sulfate, filtered, concentrated, and chromatographed on a silica gel column (6 cm×28 cm, 35:6:1=hexane:methylene chloride:ethyl acetate, 1% distilled triethylamine) to afford 445 mg (73%) of the title compound: Rf=0.28 (35:6:1=hexane:methylene chloride:ethyl acetate, 1% distilled triethylamine); $^1$H NMR $\delta$6.90 (m, 2H),6.1 (s, C=CHO), 3.32–3.24 (tt, CH$_2$CHCH$_2$), 2.84–2.74(1H), 2.16–2.08(1H); $^{13}$C NMR $\delta$117.0 (C=CHO), 40.0, 35.2, 33.8, 30.1, 25.3.

Step G: 1-[2-(2-Trityl-tetrazol-5-yl)phenyl]-4-formyl-cyclohexane

A 100 ml round-bottom flask containing 316 mg (0.52 mmol, 1.0 equiv) of the starting vinyl ether (from Step F) and 6 ml dioxane was cooled down to 0° C., and 4 ml concentrated hydrochloric acid was added. The resultant mixture was warmed up to room temperature, and stirred for 16 hours. Ethyl acetate was added, and the mixture was concentrated in vacuo to reduce the bulk of dioxane and extracted with 8×10 ml ethyl acetate. The combined organic portion was dried over anhydrous sodium sulfate, filtered, concentrated, and pumped with high vacuum to get rid of any residual acid.

The mixture was redissolved in 4 ml methylene chloride (over sieves) to form a bright yellow solution, into which was added 730 ml (5.20 mmol, 10.0 equiv) freshly distilled triethylamine, resulted in the disappearance of the yellow color, and 382 mg (1.4 mmol, 2.6 equiv) of triphenylmethyl chloride. The tritylation reaction was stirred at room temperature for 17 minutes and then quenched with saturated aqueous sodium bicarbonate solution. Layers were separated, and the aqueous layer was extracted with 5×15 ml methylene chloride. The combined organic portion was washed with saturated aqueous sodium bicarbonate solution, dried over anhydrous sodium sulfate, filtered, concentrated, and chromatographed on a silica gel column (5 cm×28 cm, 7.5:1=hexane:ethyl acetate, 1% distilled triethylamine) to afford 220 mg (84%) of the desired product as a mixture of two isomers (NMR ratio=5:1): Rf=0.29 (7:1=hexane:ethyl acetate, 1% distilled triethylamine); $^1$H NMR $\delta$9.71 and 9.50 (CHO from 2 isomers).

Step H: 1-[2-(2-Trityl-tetrazol-5-yl)phenyl]-4-hydroxymethylcyclohexane

A 50 ml round-bottom flask, equipped with a magnetic stirring bar, septum, and nitrogen inlet, was charged with 220 mg (0.44 mmol, 1.0 equiv) of 1-[2-(2-trityl-tetrazol-5-yl)phenyl]-4-formylcyclohexane (from Step G) and 4 ml THF (over sieves). Into this clear solution, after being cooled down to −25° C., was added 530 μl (1.0M solution in THF, 0.53 mmol, 1.2 equiv) L-Selectride solution. After one hour, another 530 μl of L-Selectride solution was added to push the reaction to completion. The reaction was quenched after 1.5 hours with saturated aqueous sodium bicarbonate solution. Ethyl acetate was added to dissolve the organics. Layers were separated, and the aqueous layer was extracted with 5×10 ml ethyl acetate. The combined organic portion was washed with saturated aqueous sodium bicarbonate solution, dried over anhydrous sodium sulfate, filtered, concentrated, and chromatographed on a silica gel column (3 cm×31 cm, 4:6:1=hexane:methylene chloride:ethyl acetate, 1% distilled triethylamine) to afford 180 mg (82%) of the title alcohol: Rf=0.32 (4:6:1=hexane:methylene chloride:ethyl acetate, 1% distilled triethylamine); $^1$H NMR $\delta$3.71–3.67 (dd, CHCH$_2$OH from one isomer), 3.38–3.32 (dd, CHCH$_2$OH from the other isomer), 3.10–3.00 (tt, CH$_2$CHCH$_2$); $^{13}$C NMR $\delta$68.6, 40.2, 40.0, 33.2, 29.4.

Step I: 1-[2-(2-Trityl-tetrazol-5-yl)phenyl]-4-iodomethylcyclohexane (A) Into a 25 ml round-bottom flask was added 250 mg (0.50 mmol, 1.0 equiv) of 1-[2-(2-trityl-tetrazol-5-yl)phenyl]-4-hydroxymethyl-cyclohexane (from Step H), 6 ml methylene chloride (over sieves), 610 μl (3.50 mmol, 7.0 equiv) diisopropylethylamine (over sieves), and 116 mg (0.65 mmol, 1.3 equiv) methanesulfonic anhydride. 9 more mg (0.1 equiv) of methanesulfonic anhydride was added after 37 minutes to push the mesylate formation to completion. 2.8 g (7.49 mmol, 15 equiv) tetrabutylammonium iodide was added into the mesylate solution in one portion, and the resultant solution was brought up to reflux temperature to go for 14.5 hours. More tetrabutylammonium iodide (1.4 g, 7.5 equiv) was added, and the system was kept under reflux for another 12 hours. The reaction crude was cooled back down to room temperature and loaded on a silica gel column (6 cm×26 cm, 2:1=hexane:ethyl acetate, 1% distilled triethylamine) without any workup. 130 mg (43%) of the desired iodide was isolated: Rf=0.68 (2:1=hexane:ethyl acetate, 1% distilled triethylamine); $^1$H NMR (in CD$_2$Cl$_2$) $\delta$3.30 (d, CHCH$_2$I from one isomer), 3.02 (d, CHCH$_2$I from the other isomer), 3.08–2.96 (m, CH$_2$CHCH$_2$).

Step J: 3-(N-tert-Butoxycarbonylamino)-N-[1-[[4-[2-(2-trityl-tetrazol-5-yl)-phenyl]-cyclohexyl]methyl]-2,3,4,5-tetrahydro-2-oxo-1H-1-benzazepin-3(R)-yl]-3-methylbutanamide A 10 ml flask, equipped with a magnetic stirring bar, septum, and nitrogen inlet, was charged with 38 mg of the protected lactam (from Step I, EXAMPLE 1, 0.10 mmol, 1.2 equiv), 0.5 ml DMF (over sieves), and 5 mg (80% dispersion in mineral oil, 0.16 mmol, 1.8 equiv) of sodium hydride. Hydrogen evolution occurred immediately. The resultant mixture was stirred at room temperature for half an hour, during which the mixture turned into a clear solution. A solution of 52 mg (0.09 mmol, 1.0 equiv) of the iodide (from Step I) in 1 ml DMF was cannulated into the deprotonated lactam solution. The system was then brought up to ~45° C. to go for 26 hours, cooled back down to room temperature, and quenched with saturated aqueous sodium bicarbonate solution. Ethyl acetate was added to dissolve the organics. Layers were separated, and the aqueous layer was extracted with 4×15 ml ethyl acetate. The combined organic portion was washed with saturated aqueous sodium bicarbonate solution, dried over anhydrous sodium sulfate, filtered, concentrated, and chromatographed on a silica gel column (3 cm×26 cm, 3:2=hexane:ethyl acetate, 1% distilled triethylamine) to afford 14 mg (19%) of the desired product: Rf=0.56 (2:3=hexane:ethyl acetate, 1% distilled triethylamine); $^1$H NMR $\delta$6.70 (d, NH), 5.35 (s, NH), 4.43–4.35 (m, COCHCH$_2$), 4.12–4.04 (dd, J=8.5 Hz, 15.1 Hz, 1H in NCH$_2$), 3.26–3.19 (dd, J=6.0 Hz, 15.1 Hz, 1H in NCH$_2$).

Step K: 3-Amino-N-[1-[[4-[2-(1H-tetrazol-5-yl)-phenyl]cyclohexyl]methyl]-2,3,4,5-tetrahydro-2-oxo-1H-1-benzazepin-3(R)-yl]-3-methylbutanamide, trifluoroacetate Using the same procedure as Step S, EXAMPLE 1, 25 mg (0.029 mmol, 1.0 equiv) 3-(N-tert-butoxyamino)-N-[1-[[4-[2-(2-trityltetrazol-5-yl)-phenyl]-cyclohexyl]-methyl]-2,3,4,5-tetrahydro-2-oxo-1H-1-benzazepin-3(R)-yl]-3-methylbutanamide (from Step J) was deprotected to afford 10 mg (55%) of the title compound: $^1$H NMR (in CD$_3$OD) $\delta$4.40–4.30 (dd, J=9.1 Hz, 12.2 Hz, COCHCH$_2$), 4.21–4.14 (dd, J=7.3 Hz, 13.3 Hz, 1H in NCH$_2$), 3.56–3.49 (dd, J=6.0 Hz, 13.3 Hz, 1H in NCH$_2$); $^{13}$C NMR (in CD$_3$OD) $\delta$174.4, 173.3, 56.8 and 52.9 (NCH$_2$ and COCHCH$_2$), 55.5 (CH$_2$C(CH$_3$)$_2$), 45.7 (COCH$_2$); FAB-MS: calculated C$_{29}$H$_{38}$N$_7$O$_2$=516.7, found 516.9 (M+H, 20%).

EXAMPLE 7

3-[2(R)-Hydroxypropyl]amino-N-[1-[[4-[2-(1H-tetrazol-5-yl)-phenyl]cyclohexyl]methyl]-2,3,4,5-tetrahydro-2-oxo-1H-1-benzazepin-3(R)-yl]-3-methylbutanamide, trifluoroacetate Step A: 3-[2(R)-Benzyloxypropyl]amino-N-[1-[[4-[2-(2-trityltetrazol-5-yl)-phenyl]-cyclohexyl]methyl]-2,3,4,5-tetrahydro-2-oxo-1H-1-benzazepin-3(R)-yl]-3-methylbutanamide Using the same procedure as Step J, EXAMPLE 6, 181 mg (0.30 mmol, 1.0 equiv) of 1-[2-(2-trityl-tetrazol-5-yl)phenyl]-4-iodomethyl-cyclohexane (from Step I, EXAMPLE 6) was alkylated onto 138 mg (0.33 mmol, 1.1 equiv) of the protected lactam (from Step C, EXAMPLE 5) to afford 100 mg (37%) the title compound: Rf=0.32 (90:1:1=chloroform:methanol:concentrated ammonium hydroxide), $^1$H NMR $\delta$4.65–4.52 (2d, J=12.1 Hz, OCH$_2$), 4.55–4.40(m, COCHCH$_2$), 4.14–4.02 (dd, J=7.9 Hz, 1H in NCH$_2$), 3.92–3.80 (m, CH$_2$CHCH$_3$), 3.25–3.15 (dd, J=6.0 Hz, 15.1 Hz, 1H in NCH$_2$); $^{13}$C NMR $\delta$75.2 (CH$_2$CHCH$_3$), 70.8 (OCH$_2$), 54.2 (NCH$_2$).

Step B: 3-[2(R)-Hydroxypropyl]amino-N-[-1-[[4-[2-(1H-tetrazol-5-yl)-phenyl]cyclohexyl]methyl]-2,3,4,5-tetrahydro-2-oxo-1H-1-benzazepin-3(R)-yl]-3-methylbutanamide, trifluoroacetate Using the same procedure as Step H, EXAMPLE 5, 100 mg of the starting material (from Step A) was deprotected to afford 50 mg (66%) of the title compound: $^1$H NMR (in CD$_3$OD) $\delta$4.30–4.25 (dd, COCHCH$_2$), 4.15–4.09(dd, 1H in NCH$_2$), 3.95–3.88 (m, CH2CHCH$_3$), 3.50–3.43 (dd, 1H in NCH$_2$), 3.12–3.05 (dd, 1H), 2.95–2.83 (m, 1H), 2.40–2.28 (m, 1H), 2.18–2.08 (m, 1H); FAB-MS: calculated C$_{32}$H$_{44}$N$_7$O$_3$=574.8, found 574.8 (M+H, 50%).

EXAMPLE 8

3-Amino-N-[1-[[4-[2-(1H-tetrazol-5-yl)-phenyl]-cyclohexenyl]methyl]-2,3,4,5-tetrahydro-2-oxo-1H-1-benzazepin-3(R)-yl]-3-methylbutanamide, trifluoroacetate Step A: Trifluoromethanesulfonic acid [4-[2-[2-trityl-2H-tetrazol-5-yl]phenyl]-1-cyclohexen-1-yl]ester (A) A 250 ml round-bottom flask, equipped with a magnetic stirring bar, septum, and a nitrogen inlet, was charged with 380 $\mu$l (2.70 mmol, 1.3 equiv) distilled diisopropylamine and 9 ml freshly distilled THF. Into this clear solution, after being cooled down to −78° C., was added 1.73 ml (1.44M solution in hexanes, 2.49 mmol, 1.2 equiv) n-butyllithium. The resultant solution was stirred at −78° C. for 5 minutes, 0° C. for 30 minutes, and then cooled back down to −78° C.

(B) A solution of 1005 mg (2.08 mmol, 1.0 equiv) 1-[2-(2-trityl-tetrazol-5-yl)phenyl]-cyclohexan-4-one (from Step D, EXAMPLE 6) in 21 ml THF was cannulated into the LDA solution from (A) at −78° C. in a course of 15 minutes. The resultant yellow solution was stirred at −78° C. for 2 hours.

(C) A solution of 900 mg (2.49 mmol, 1.2 equiv) N-phenyltrifluoromethanesulfonimide in 6 ml THF was cannulated into the lithium enolate solution from (B). The resultant solution was stirred at −78° C. for 5 minutes, 0° C. for 2 hours, room temperature for 1.5 hours, concentrated in vacuo, and chromatographed on a silica gel column (6 cm×29 cm, 35:6:1=hexane::methylene chloride:ethyl acetate, 1% distilled triethylamine) to afford 823 mg (64%) of the title compound: Rf=0.21 (35:6:1=hexane:methylene chloride:ethyl acetate, 1% distilled triethylamine); $^1$H NMR $\delta$5.69–5.63 (dd, C=CH), 3.42–3.31 (m, CH$_2$CHCH$_2$).

Step B: 4-[2-[2-Trityl-2H-tetrazol-5-yl]phenyl]-1-cyclohexane-1-carboxylic acid methyl ester Into a 50 ml round-bottom flask was added 300 mg (0.49 mmol, 1.0 equiv) of the triflate (from Step A), 2 ml DMF (over sieves), 140 $\mu$l (0.97 mmol, 2.0 equiv) freshly distilled triethylamine, 216 mg (0.19 mmol, 0.38 equiv) tetrakis(triphenylphosphine) palladium, and 800 $\mu$l (19.5 mmol, 40 equiv) methanol at room temperature. The system was evacuated by house vacuum and flushed with carbon monoxide several times, and then a steady CO atmosphere was provided to the system by a balloon. The resultant mixture was stirred at room temperature for 15.75 hours, concentrated, and chromatographed on a silica gel column (6 cm×28 cm, 8:1=hexane-ethyl acetate, 1% distilled triethylamine) to afford 177 mg (69%) of the title compound: Rf=0.28 (6:1=hexane:ethyl acetate, 1% distilled triethylamine); $^1$H NMR $\delta$6.92–6.85 (C=CH), 3.76 (s, OMe).

Step C: 1-[2-(2-Trityl-tetrazol-5-yl)phenyl]-4-hydroxymethyl-3-cyclohexene

Into a 50 ml flask was added 358 mg (0.68 mmol, 1.0 equiv) of the starting ester (from Step B) and 6 ml distilled THF. Into this clear solution, after being cooled down to −78° C., was added 2.7 ml (1.0M solution in THF, 2.7 mmol, 4.0 equiv) L-Selectride solution. The resultant solution was stirred at −78° C. for 5 minutes and 5.5 hours at −45° C., and then 680 $\mu$l (1.0 equiv) L-Selectride was added into the solution to push the reaction to completion. The reaction was quenched after 7 hours with saturated aqueous potassium carbonate solution at −45° C. Ethyl acetate was added. The mixture was warmed up to 0° C., and 1.5 ml 30% aqueous hydrogen peroxide solution was added. The resultant mixture was stirred at 0° C. for 30 minutes, and then layers were separated. The aqueous layer was extracted with 5×10 ml ethyl acetate, and the combined organic portion was washed with saturated aqueous potassium carbonate solution, dried over anhydrous sodium sulfate, filtered, concentrated, and chromatographed on a silica gel column (3 cm×32 cm, 2:1=hexane:ethyl acetate, 1% distilled triethylamine) to afford 254 mg of the desired product, contaminated with 13% of 1-[2-(2-trityl-tetrazol-5-yl)phenyl]-4-hydroxymethylcyclohexane (the over-reduced compound). Rf=0.28 (2:1=hexane-ethyl acetate, 1% distilled triethylamine); $^1$H NMR $\delta$5.65–5.59 (C=CH), 3.96 (app s, CH$_2$OH), 3.44–3.32 (m, CH$_2$CHCH$_2$); $^{13}$C NMR $\delta$67.2 (CH$_2$OH).

Step D: 1-[2-(2-Trityl-tetrazol-5-yl)phenyl]-4-bromomethyl-3-cyclohexene

Using the same precedure as Step Q, EXAMPLE 1, 120 mg of 1-[2-(2-trityl-tetrazol-5-yl)phenyl]-4-hydroxymethyl-3-cyclohexene (from Step C) was converted into 96 mg of the title compound: Rf=0.56 (4:1=hexane:ethyl acetate, 1% distilled triethylamine); $^1$H NMR (in CD$_2$Cl$_2$) δ5.87–5.81 (C=CH), 4.02–3.91 (2d, CH$_2$Br), 3.41–3.30 (m, CH$_2$CHCH$_2$); $^{13}$C NMR (in CD$_2$Cl$_2$) δ39.5 (CH$_2$Br), 35.9 (CH$_2$CHCH$_2$).

Step E: 3-(N-tert-Butoxycarbonylamino)-N-[1-[[4-[2-(2-trityltetrazol-5-yl)-phenyl]-cyclohexenyl]methyl]-2,3,4,5-tetrahydro-2-oxo-1H-1-benzazepin-3(R)-yl]-3-methylbutanamide Using the same procedure as Step R, EXAMPLE 1, 96 mg 1-[2-(2-trityl-tetrazol-5-yl)phenyl]-4-bromomethyl-3-cyclohexene was reacted with the starting protected lactam (from Step I, EXAMPLE 1) to afford 127 mg (92%) of a mixture of two diastereomers. Isomer A: Rf=0.37 (1:1=hexane:ethyl acetate, 1% distilled triethylamine); $^1$H NMR δ6.70 (d, NH), 5.47 (bs), 5.37 (bs), 4.65–4.56 (d, J=15.1 Hz, 1H in NCH$_2$), 4.24–4.15 (d, J=15.1 Hz, 1H in NCH$_2$), 3.40–3.30 (m, CH$_2$CHCH$_2$). Isomer B: Rf=0.32 (1:1=hexane:ethyl acetate, 1% distilled triethylamine); $^1$H NMR δ6.67 (d, NH), 5.51 (bs), 5.37 (bs), 3.40–3.30 (m, CH$_2$CHCH$_2$).

Step F: 3-Amino-N-[1-[[4-[2-(1H-tetrazol-5-yl)-phenyl]-cyclohexenyl]-methyl]-2,3,4,5-tetrahydro-2-oxo-1H-1-benzazepin-3(R)-yl]-3-methylbutanamide, trifluoroacetate, Isomer A Using the same procedure as Step S, EXAMPLE 1, 47 mg of the starting Isomer A was deprotected to afford 17 mg of the title compound: $^1$H NMR (in CD$_3$OD) δ5.66 (bs, C=CH), 4.39 (s, NCH$_2$), 4.40–4.30 (dd, COCHCH$_2$), 3.10–3.00 (m, CH$_2$CHCH$_2$); FAB-MS: calculated C$_{29}$H$_{36}$N$_7$O$_2$=514.7, found 514.8 (M+H, 80%).

Step G: 3-Amino-N-[1-[[4-[2-(1H-tetrazol-5-yl)-phenyl]-cyclohexenyl]-methyl]-2,3,4,5-tetrahydro-2-oxo-1H-1-benzazepin-3(R)-yl]-3-methylbutanamide, trifluoroacetate, Isomer B Using the same procedure as Step S, EXAMPLE 1, 32 mg of the starting Isomer B was deprotected to afford 15 mg of the title compound: $^1$H NMR (in CD$_3$OD) δ5.60 (bs, C=CH), 4.39 (s, NCH$_2$), 4.40–4.30 (dd, COCHCH$_2$), 3.00–2.88 (m, CH$_2$CHCH$_2$); FAB-MS: calculated C$_{29}$H$_{36}$N$_7$O$_2$=514.7, found 514.8 (M+H, 30%).

EXAMPLE 9

3-Amino-N-[1-[4-(4-carboxamido-5-oxazolyl)-benzyl]-2,3,4,5-tetrahydro-2-oxo-1H-1-benzazepin-3(R)-yl]-3-methylbutanamide, trifluoroacetate 4-(4-Carbomethoxy-5-oxazolyl)-benzyl bromide is prepared as described in EP 0 485 929 A1 Example 6 a) to d), see also Scheme 19.

Step A: 3-tert.-Butoxycarbonylamino-N-[1-[4-(4-carbomethoxy-5-oxazolyl)-benzyl]-2,3,4,5-tetrahydro-2-oxo-1H-1-benzazepin-3(R)-yl]-3-methylbutanamide Using a procedure fully described in EXAMPLE 1, Step R, a solution of 150 mg, 0.40 mmol, of protected lactam (obtained according to EXAMPLE 1, step I) in 2.0 ml of anhydrous DMF is stirred under N$_2$ at 0° C. To this 16 mg of sodium hydride (80% dispersion in mineral oil, 0.48 mmol, 1.2 equiv.) are added. The reaction mixture is allowed to come to room temperature over 20 minutes. Then a solution of 0.44 mmol, 1.1 equiv. of 4-(4-carbomethoxy-5-oxazolyl)-benzyl bromide in 3.0 ml of DMF is added over 5 minutes. The reaction is quenched at 0° C. with saturated aqueous NaHCO$_3$ solution. Extraction with ethyl acetate and further purification as fully described in EXAMPLE 1 step R gives 3-tert-butoxycarbonylamino-N-[1-[4-(4-carbomethoxy-5-oxazolyl)-benzyl]-2,3,4,5-tetrahydro-2-oxo-1H-1-benzazepin-3(R)-yl]-3-methylbutanamide, which is characterized by its mass and NMR spectra.

Step B: 3-tert-Butoxycarbonylamino-N-[1-[4-(4-carboxamido-5-oxazolyl)-benzyl]-2,3,4,5-tetrahydro-2-oxo-1H-1-benzazepin-3(R)-yl]-3-methylbutanamide The methyl ester obtained in the previous step is refluxed in a mixture of ethanol and conc. aqueous ammonia. Concentration of the reaction mixture in vacuo gives crude 3-tert-butoxycarbonylamino-N-[1-[4-(4-carboxamido-5-oxazolyl)-benzyl]-2,3,4,5-tetrahydro-2-oxo-1H-1-benzazepin-3(R)-yl]-3-methylbutanamide, which is characterized by its mass and NMR spectra.

Step C: 3-Amino-N-[1-[4-(4-carboxamido-5-oxazolyl)-benzyl]-2,3,4,5-tetrahydro-2-oxo-1H-1-benzazepin-3(R)-yl]-3-methylbutanamide, trifluoroacetate The amine protected compound obtained in the previous step is deprotected as fully described in EXAMPLE 1, Step S to give 3-amino-N-[1-[4-(4-carboxamido-5-oxazolyl)-benzyl]-2,3,4,5-tetrahydro-2-oxo-1H-1-benzazepin-3(R)-yl]-3-methylbutanamide, trifluoroacetate, which is characterized by its mass and NMR spectra.

EXAMPLE 10

3-Amino-N-[1-[4-(2-(1H-tetrazol-5-yl)-1-pyrrolyl)-benzyl]-2,3,4,5-tetrahydro-2-oxo-1H-1-benzazepin-3(R)-yl]-3-methylbutanamide, trifluoroacetate Step A: According to the procedure of Example 4, Step B, 4.26 mmol of 1-(4-methylphenyl)-2-cyanopyrrole and 5.32 mmol of tributyltin azide is heated in 10 ml of xylene for 18 hrs. After isolation of the crude 4-(2-(1H-tetrazol-5-yl)-1-pyrrolyl)-methylbenzene as described in Example 4, Step B, the dry crude product is suspended in 50 ml of methylene chloride and treated with 4.0 ml of triethylamine, followed by 2.42 g of triphenylmethyl chloride. After workup and purification as fully described in Example 4, Step B, the 4-(2-(2H-2-trityltetrazol-5-yl)-1-pyrrolyl)-methylbenzene is obtained and characterized by its mass and NMR spectra.

Step B: A solution of 3.07 mmol of 4-(2-(2H-2-trityl-tetrazol-5-yl)-1-pyrrolyl)-methylbenzene in 50 ml of carbon tetrachloride is treated with 550 mg of N-bromosuccinimide and 25 mg of benzoyl peroxide and heated to reflux for 3 hours. The reaction mixture is allowed to come to room temperature and ished with 10 ml of water and 10 ml of saturated aqueous sodium chloride. The organic layer is dried and evaporated in vacuo to a light residue, which is characterized by its mass and NMR spectra as the desired 4-(2-(2H-2-trityl-tetrazol-5-yl)-1-pyrrolyl)-benzyl bromide.

Step C: Using a procedure fully described in Example 1, Step R, a solution of 150 mg, 0.40 mmol, of protected lactam (obtained according to Example 1, Step I) in 2.0 ml of anhydrous DMF is stirred under N$_2$ at 0° C. To this 16 mg of sodium hydride (80% dispersion in mineral oil, 0.48 mmol, 1.2 equiv.) are added. The reaction mixture is allowed to come to room temperature over 20 minutes. Then a solution of 0.44 mmol, 1.1 equiv. of 4-(2-(2H-2-trityltetrazol-5-yl)-1-pyrrolyl)-benzyl bromide in 3.0 ml of DMF is added over 5 minutes. The reaction is quenched at 0° C. with saturated aqueous NaHCO$_3$ solution. Extraction with ethyl acetate and further purification as fully described in Example 1, Step R gives 3-tert-butoxycarbonylamino-N-[1-[4-(2-(2H-2-trityltetrazol-5-yl)-1-pyrrolyl)-benzyl]-2,3,4,5- tetrahydro-2-oxo-1H-1-benzazepin-3(R)-yl]-3-methyl-butanamide, which is characterized by its mass and NMR spectra.

Step D: The amine protected compound obtained in the previous step is deprotected as fully described in Example 1, Step S to give 3-amino-N-[1-[4-(1-(1H-tetrazol-5-yl)-1-pyrrolyl)-benzyl]-2,3,4,5-tetrahydro-2-oxo-1H-1-benzazepin-3(R)-yl]-3-methylbutanamide, trifluoroacetate, which is characterized by its mass and NMR spectra.

EXAMPLE 11

3-Amino-N-[1-[4-(4-bromo-2-(1H-tetrazol-5-yl)-1-pyrrolyl)-benzyl]-2,3,4,5-tetrahydro-2-oxo-1H-1-benzazepin-3(R)-yl]-3-methylbutanamide, trifluoroacetate Step A: To a solution of 1-(4-methylphenyl)-2-cyanopyrrole (1.274 g) in tetrahydrofuran (25 ml) is added N-bromosuccinimide (1.776 g) in several portions at room temperature. After being stirred for 3 hours at ambient temperature, the mixture is concentrated in vacuo. The residue is treated with diethyl ether. The precipitates are removed by filtration and washed with a small amount of diethyl ether. The filtrates are concentrated in vacuo to give an oily residue, which is purified by silicagel column chromatography (elution by 40% methylene chloride in n-hexane) to yield 1-(4-methylphenyl)-4-bromo-2-cyanopyrrole as a solid.

Step B: Using 1-(4-methylphenyl)-4-bromo-2-cyanopyrrole as starting material and following exactly Steps A, B, C, and D of Example 10 the analog 3-amino-N-[1-[4-(4-bromo-2-(1H-tetrazol-5-yl)-1-pyrrolyl)-benzyl]-2,3,4,5-tetrahydro-2-oxo-1H-1-benzazepin-3(R)-yl]-3-methylbutanamide, trifluoroacetate is obtained.

What is claimed is:

1. A compound having the formula:

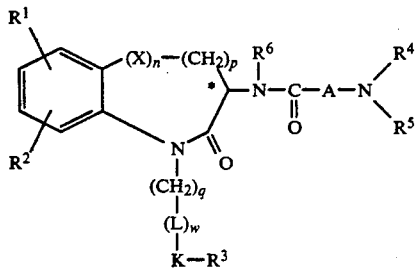

n is 0 or 1;
p is 0 to 3;
q is 0 to 4;
w is 0 or 1;
X is C=O or

m is 0 to 2;
L and K are independently

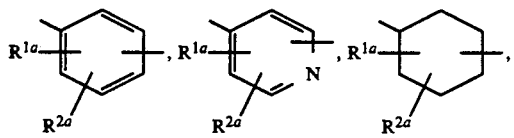

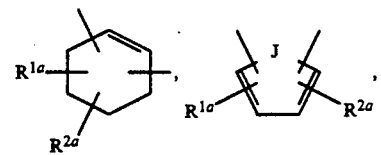

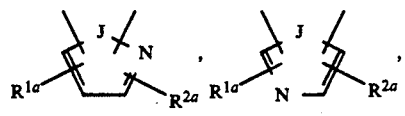

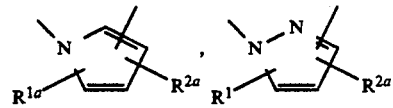

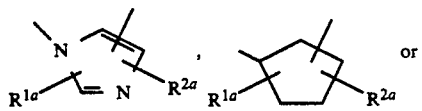

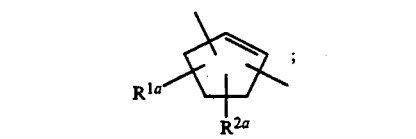

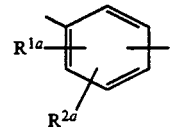

where J is O, S or N—R$^{13}$ with the proviso that when w is 0, K is other than

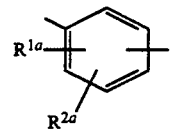

and when w is 1, either L or K must be other than $R^1$, $R^2$, $R^{1a}$, and $R^{2a}$ are independently hydrogen, halogen, $C_1$-$C_7$ alkyl, $C_1$-$C_3$ perfluoroalkyl, $C_1$-$C_3$ perfluoroalkoxy, —S(O)$_m$R$^{7a}$, cyano, nitro, R$^{7b}$O(CH$_2$)$_v$—, R$^{7b}$COO(CH$_2$)$_v$—, R$^{7b}$OCO(CH$_2$)$_v$—, R$^4$R$^5$N(CH$_2$)$_v$—, R$^{7b}$CON(R$^4$)(CH$_2$)$_v$—, R$^4$R$^5$NCO(CH$_2$)$_v$—, phenyl or substituted phenyl where the substituents are from 1 to 3 of halogen, $C_1$-$C_6$ alkyl, $C_1$-$C_6$ alkoxy or hydroxy;

$R^{7a}$ and $R^{7b}$ are independently hydrogen, $C_1$-$C_3$ perfluoroalkyl, $C_1$-$C_6$ alkyl, substituted $C_1$-$C_6$ alkyl, where the substituents are phenyl or substituted phenyl; phenyl or substituted phenyl where the phenyl substituents are from 1 to 3 of halogen, $C_1$-$C_6$ alkyl, $C_1$-$C_6$ alkoxy or hydroxy and v is 0 to 3;

$R^3$ is hydrogen, $R^9$, $C_1$-$C_6$ alkyl substituted with $R^9$, phenyl substituted with $R^9$ or phenoxy substituted with $R^9$;

$R^9$ is

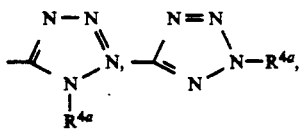

$R^{7b}O(CH_2)_v$—, $R^{7b}COO(CH_2)_v$—, $R^{7b}OCO(CH_2)_v$—, $R^{7b}CO(CH_2)_v$—, $R^{7b}O(CH_2)_vCO$—, $R^4R^5N(CH_2)_v$—, $R^{7b}CON(R^4)(CH_2)_v$—, $R^4R^5NCO(CH_2)_v$—, $R^4R^5NCS(CH_2)_v$—, $R^4R^5NN(R^5)CO(CH_2)_v$—, $R^4R^5NN(R^5)CS(CH_2)_v$—, $R^{7b}CON(R^4)N(R^5)CO(CH_2)_v$—, $R^{7b}CON(R^4)N(R^5)CS(CH_2)_v$—, $R^4N(OR^{7b})CO(CH_2)_v$—, $R^{7a}CON(OR^{7b})CO(CH_2)_v$—, $R^{4b}R^{12a}NCON(R^{12b})(CH_2)_v$—, $R^{4b}R^{12a}NCSN(R^{12b})(CH_2)_v$—, $R^{4b}R^{12a}NN(R^{12b})CSN(R^{12c})(CH_2)_v$—, $R^{4b}R^{12a}NN(R^{12b})CON(R^{12c})(CH_2)_v$—, $R^{4b}R^{12a}NN(R^{12b})COO(CH_2)_v$—, $R^{4b}R^{12a}NCOO(CH_2)_v$— or $R^{13}OCON(R^{12b})(CH_2)_v$—, where v is 0 to 3;

$R^{12a}$, $R^{12b}$ and $R^{12c}$ are independently $R^{5a}$, $OR^{5a}$, or $COR^{5a}$; $R^{12a}$ and $R^{12b}$, or $R^{12b}$ and $R^{12c}$, or $R^{13}$ and $R^{12b}$, or $R^{12a}$ and $R^{4b}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 3 and $R^1$ and $R^{10}$ are as defined;

$R^{13}$ is $C_1$-$C_3$ perfluoroalkyl, $C_1$-$C_6$ alkyl, substituted $C_1$-$C_6$ alkyl, where the substituents are hydroxy, —$NR^{10}R^{11}$, carboxy, phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy where $R^{10}$ and $R^{11}$ are independently hydrogen, $C_1$-$C_6$ alkyl, phenyl, phenyl $C_1$-$C_6$ alkyl, $C_1$-$C_5$-alkoxycarbonyl or $C_1$-$C_5$-alkanoyl-$C_1$-$C_6$ alkyl;

$R^4$, $R^{4a}$, $R^{4b}$, $R^5$ and $R^{5a}$ are independently hydrogen, phenyl, substituted phenyl, $C_1$-$C_{10}$ alkyl, substituted $C_1$-$C_{10}$ alkyl, $C_3$-$C_{10}$ alkenyl, substituted $C_3$-$C_{10}$ alkenyl, $C_3$-$C_{10}$ alkynyl or substituted $C_3$-$C_{10}$ alkynyl where the substituents on the phenyl, alkyl, alkenyl or alkynyl are from 1 to 5 of hydroxy, $C_1$-$C_6$ alkoxy, $C_3$-$C_7$ cycloalkyl, fluoro, $R^1$, $R^2$ independently disubstituted phenyl $C_1$-$C_3$ alkoxy, $R^1$, $R^2$ independently disubstituted phenyl, $C_1$-$C_{20}$ alkanoyloxy, $C_1$-$C_5$ alkoxycarbonyl, carboxy, formyl or —$NR^{10}R^{11}$; or $R^4$ and $R^5$ can be taken together to form —$(CH_2)_rB(CH_2)_s$— where B, r, s, $R^1$, $R^2$, $R^{10}$ and $R^{11}$ are as defined above;

$R^6$ is hydrogen, $C_1$-$C_{10}$ alkyl, phenyl or phenyl $C_1$-$C_{10}$ alkyl;

A is

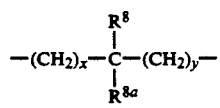

where x and y are independently 0-3;

$R^8$ and $R^{8a}$ are independently hydrogen, $C_1$-$C_{10}$ alkyl, trifluoromethyl, phenyl, substituted $C_1$-$C_{10}$ alkyl where the substituents are from 1 to 3 of imidazolyl, indolyl, hydroxy, fluoro, $S(O)_mR^{7a}$, $C_1$-$C_6$ alkoxy, $C_3$-$C_7$ cycloalkyl, $R^1$, $R^2$ independently disubstituted phenyl $C_1$-$C_3$ alkoxy, $R^1$, $R^2$ independently disubstituted phenyl, $C_1$-$C_5$-alkanoyloxy, $C_1$-$C_5$ alkoxycarbonyl, carboxy, formyl or —$NR^{10}R^{11}$ where $R^1$, $R^2$, $R^{10}$ and $R^{11}$ are as defined above; or $R^8$ and $R^{8a}$ can be taken together to form —$(CH_2)_t$— where t is 2 to 6; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms;

and pharmaceutically acceptable salts thereof.

2. A compound of claim 1 wherein:

n is 0;

p is 0 to 3;

q is 0 to 2;

w is 0 or 1;

L and K are as defined above;

m is 0 to 2;

$R^1$, $R^2$, $R^{1a}$ and $R^{2a}$ are independently hydrogen, halogen, $C_1$-$C_7$ alkyl, $C_1$-$C_3$ perfluoroalkyl, —$S(O)_mR^{7a}$, $R^{7b}O(CH_2)_v$—, $R^{7b}COO(CH_2)_v$—, $R^{7b}OCO(CH_2)_v$—, phenyl or substituted phenyl where the substituents are from 1 to 3 of halogen, $C_1$-$C_6$ alkyl, $C_1$-$C_6$ alkoxy or hydroxy;

$R^{7a}$ and $R^{7b}$ are independently hydrogen, $C_1$-$C_3$ perfluoroalkyl, $C_1$-$C_6$ alkyl, substituted $C_1$-$C_6$ alkyl, where the substituents are phenyl; and v is 0 to 2;

$R^3$ is hydrogen, $R^9$, $C_1$-$C_6$ alkyl substituted with $R^9$, phenyl substituted with $R^9$, or phenoxy substituted with $R^9$;

$R^9$ is

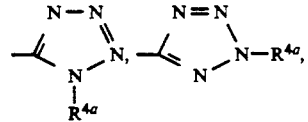

$R^{7b}O(CH_2)_v$—, $R^{7b}COO(CH_2)_v$—, $R^{7b}OCO(CH_2)_v$—, $R^{7b}CO(CH_2)_v$—, $R^4R^5N(CH_2)_v$—, $R^{7b}CON(R^4)(CH_2)_v$—, $R^4R^5NCO(CH_2)_v$—, $R^4R^5NCS(CH_2)_v$—, $R^4R^5NN(R^5)CO(CH_2)_v$—, $R^{7b}CON(R^4)N(R^5)CO(CH_2)_v$—, $R^4N(OR^{7b})CO(CH_2)_v$—, $R^{7a}CON(OR^{7b})CO(CH_2)_v$—, $R^{4b}R^{12a}NCON(R^{12b})(CH_2)_v$—, $R^{4b}R^{12a}NCSN(R^{12b})(CH_2)_v$—, $R^{4b}R^{12a}NN(R^{12b})CON(R^{12c})(CH_2)_v$—, $R^{4b}R^{12a}NN(R^{12b})COO(CH_2)_v$—, $R^{4b}R^{12a}NCOO(CH_2)_v$—, or $R^{13}OCON(R^{12b})(CH_2)_v$—, where v is 0 to 3;

$R^{12a}$, $R^{12b}$ and $R^{12c}$ are independently $R^{5a}$, $OR^{5a}$, or $COR^{5a}$; $R^{12a}$ and $R^{12b}$, or $R^{12b}$ and $R^{12c}$, or $R^{13}$ and $R^{12b}$ or $R^{12a}$ and $R^{4b}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 3, $R^1$ is as defined above and $R^{10}$ is hydrogen, $C_1$-$C_6$ alkyl, phenyl $C_1$-$C_6$ alkyl or $C_1$-$C_5$ alkanoyl-$C_1$-$C_6$ alkyl;

$R^{13}$ is $C_1$-$C_3$ perfluoroalkyl, $C_1$-$C_6$ alkyl, substituted $C_1$-$C_6$ alkyl, where the substituents are hydroxy, —$NR^{10}R^{11}$, carboxy, phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy; where $R^{10}$ and $R^{11}$ are as defined;

$R^4$, $R^{4a}$, $R^{4b}$, $R^5$ and $R^{5a}$ are independently hydrogen, phenyl, substituted phenyl, $C_1$-$C_{10}$ alkyl, substituted $C_1$-$C_{10}$ alkyl, where the substituents on the alkyl or phenyl are from 1 to 5 of hydroxy, $C_1$-$C_6$ alkoxy, $C_3$-$C_7$ cycloalkyl, fluoro, $R^1$, $R^2$ independently disubstituted phenyl $C_1$-$C_3$ alkoxy, $R^1$, $R^2$ independently disubstituted phenyl, $C_1$-$C_{20}$-alkanoyloxy, $C_1$-$C_5$ alkoxycarbonyl, carboxy or formyl; or $R^4$ and $R^5$ can be taken together to form —$(CH_2)_r$B$(CH_2)_s$— where B is $CHR^1$, O, $S(O)_m$ or N-$R^{10}$, r and s are independently 1 to 3 and $R^1$ and $R^{10}$ are as defined above;

$R^6$ is hydrogen, $C_1$-$C_{10}$ alkyl or phenyl $C_1$-$C_{10}$ alkyl;
A is

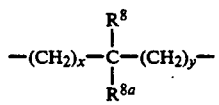

where x and y are independently 0–2;
$R^8$ and $R^{8a}$ are independently hydrogen, $C_1$-$C_{10}$ alkyl, substituted $C_1$-$C_{10}$ alkyl where the substituents are from 1 to 3 of imidazolyl, indolyl, hydroxy, fluoro, $S(O)_m R^{7a}$, $C_1$-$C_6$ alkoxy, $R^1$, $R^2$ independently disubstituted phenyl, $C_1$-$C_5$-alkanoyloxy, $C_1$-$C_5$ alkoxycarbonyl, carboxy, formyl or —$NR^{10}R^{11}$ where $R^{10}$ $R^{11}$ are independently hydrogen, $C_1$-$C_6$ alkyl, or $C_1$-$C_5$ alkanoyl-$C_1$-$C_6$ alkyl; or $R^8$ and $R^{8a}$ can be taken together to form —$(CH_2)_t$— where t is 2 to 4; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms; and pharmaceutically acceptable salts thereof.

3. A compound of claim 2 wherein:
n is 0;
p is 0 to 2;
q is 0 to 2;
w is 0 or 1;
L and K are defined as above;
m is 0 or 1;
$R^1$, $R^2$, $R^{1a}$ and $R^{2a}$ are independently hydrogen, halogen, $C_1$-$C_7$ alkyl, $C_1$-$C_3$ perfluoroalkyl, —$S(O)_m R^{7a}$, $R^{7b}O(CH_2)_v$—, $R^{7b}COO(CH_2)_v$—, $R^{7b}OCO(CH_2)_v$—, phenyl or substituted phenyl where the substituents are from 1 to 3 of halogen, $C_1$-$C_6$ alkyl, $C_1$-$C_6$ alkoxy, or hydroxy;
$R^{7a}$ and $R^{7b}$ are independently hydrogen, $C_1$-$C_6$ alkyl, substituted $C_1$-$C_6$ alkyl, where the substituents are phenyl and v is 0 to 2;
$R^3$ is hydrogen, $R^9$, $C_1$-$C_6$ alkyl substituted with $R^9$, phenyl substituted with $R^9$, or phenoxy substituted with $R^9$;
$R^9$ is

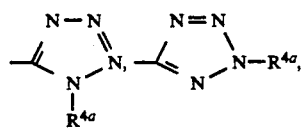

$R^{7b}O(CH_2)_v$—, $R^{7b}COO(CH_2)_v$—, $R^{7b}OCO(CH_2)_v$—, $R^{7b}CO(CH_2)_v$—, $R^4R^5N(CH_2)_v$—, $R^{7b}CON(R^4)(CH_2)_v$—, $R^4R^5NCO(CH_2)_v$—, $R^4R^5NCS(CH_2)_v$—, $R^4N(OR^{7b})CO(CH_2)_v$—, $R^{7a}$-CON(OR$^{7b}$)CO(CH$_2$)$_v$—, $R^{4b}R^{12a}$N-CON(R$^{12b}$)(CH$_2$)$_v$—, $R^{4b}R^{12a}$NCSN(R$^{12b}$)(CH$_2$)$_v$—, $R^{4b}R^{12a}$NN(R$^{12b}$)CON(R$^{12c}$)(CH$_2$)$_v$—, $R^{4b}R^{12a}$NN(R$^{12b}$)COO(CH$_2$)$_v$—, $R^{4b}R^{12a}$N-COO(CH$_2$)$_v$— or $R^{13}$OCON(R$^{12b}$)(CH$_2$)$_v$—, where v is 0 to 2;

$R^{12a}$, $R^{12b}$ and $R^{12c}$ are independently $R^{5a}$ or $OR^{5a}$, $R^{12a}$ and $R^{12b}$, or $R^{12b}$ and $R^{12c}$, or $R^{13}$ and $R^{12b}$ or $R^{12a}$ and $R^{4b}$ can be taken together to form —$(CH_2)_r$ — B —$(CH_2)_s$— where B is $CHR^1$, O, $S(O)_m$ or $NR^{10}$, m is 0, 1 or 2, r and s are independently 0 to 2, $R^1$ is as defined above and $R^{10}$ is hydrogen, $C_1$-$C_6$ alkyl or $C_1$-$C_5$ alkanoyl-$C_1$-$C_6$ alkyl;

$R^{13}$ is $C_1$-$C_6$ alkyl, substituted $C_1$-$C_6$ alkyl, where the substituents are phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy;

$R^4$, $R^{4a}$, $R^{4b}$, $R^5$ and $R^{5a}$ are independently hydrogen, $C_1$-$C_{10}$ alkyl, substituted $C_1$-$C_{10}$ alkyl, where the substituents on the alkyl are from 1 to 5 of hydroxy, $C_1$-$C_6$ alkoxy, fluoro, $R^1$, $R^2$ independently disubstituted phenyl, $C_1$-$C_{20}$-alkanoyloxy, $C_1$-$C_5$ alkoxycarbonyl or carboxy;

$R^6$ is hydrogen or $C_1$-$C_{10}$ alkyl;
A is

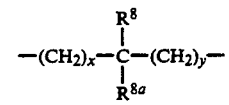

where x and y are independently 0–1;
$R^8$ and $R^{8a}$ are independently hydrogen, $C_1$-$C_{10}$ alkyl, substituted $C_1$-$C_{10}$ alkyl where the substituents are from 1 to 3 of imidazolyl, indolyl, hydroxy, fluoro, $S(O)_m R^{7a}$, $C_1$-$C_6$ alkoxy, $R^1$, $R^2$ independently disubstituted phenyl, $C_1$-$C_5$-alkanoyloxy, $C_1$-$C_5$ alkoxycarbonyl, carboxy; or $R^8$ and $R^{8a}$ can be taken together to form —$(CH_2)_t$— where t is 2; or $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms; and pharmaceutically acceptable salts thereof.

4. A compound of claim 3 wherein:
n is 0;
p is 0 to 2;
q is 1;
w is 1;
L and K are defined as above;
m is 0 or 1;
$R^1$, $R^2$, $R^{1a}$ and $R^{2a}$ are independently hydrogen, halogen, $C_1$-$C_7$ alkyl, $C_1$-$C_3$ perfluoroalkyl, —$S(O)_m R^{7a}$, $R^{7b}O(CH_2)_v$—, $R^{7b}COO(CH_2)_v$—, phenyl or substituted phenyl where the substituents are from 1 to 3 of halogen, $C_1$-$C_6$ alkyl, $C_1$-$C_6$ alkoxy, or hydroxy; $R^{7a}$ and $R^{7b}$ are independently hydrogen, $C_1$-$C_6$ alkyl, substituted $C_1$-$C_6$ alkyl, where the substituents are phenyl and v is 0 or 1;
$R^3$ is hydrogen, $R^9$, or $C_1$-$C_6$ alkyl substituted with $R^9$;
$R^9$ is

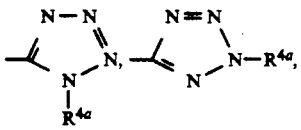

$R^{7b}O(CH_2)_r-$, $R^{7b}COO(CH_2)_r-$, $R^{7b}OCO(CH_2)_r-$, $R^{7b}CO(CH_2)_r-$, $R^{7b}CON(R^4)(CH_2)_r-$, $R^4R^5NCO(CH_2)_r-$, $R^4N(OR^{7b})CO(CH_2)_r-$, $R^{4b}R^{12a}NCON(R^{12b})(CH_2)_r-$, $R^{4b}R^{12a}NN(R^{12b})CON(R^{12c})(CH_2)_r-$, $R^{4b}R^{12a}NN(R^{12b})COO(CH_2)_r-$, $R^{4b}R^{12a}NCOO(CH_2)_r-$ or $R^{13}OCON(R^{12b})(CH_2)_r-$, where v is 0 to 2;

$R^{12a}$, $R^{12b}$ and $R^{12c}$ are independently $R^{5a}$. $R^{12a}$ and $R^{12b}$, or $R^{12b}$ and $R^{12c}$, or $R^{13}$ and $R^{12b}$ or $R^{12a}$ and $R^{4b}$ can be taken together to form $-(CH_2)_r-B-(CH_2)_s-$ where B is $CHR^1$, O, $S(O)_m$ or $NR^{10}$, m is 0, 1 or 2, r and s are independently 0 to 2, $R^1$ is as defined above and $R^{10}$ is hydrogen, $C_1-C_6$ alkyl or $C_1-C_5$ alkanoyl-$C_1-C_6$ alkyl;

$R^{13}$ is $C_1-C_6$ alkyl, substituted $C_1-C_6$ alkyl, where the substituents are phenyl or substituted phenyl; phenyl or substituted phenyl where the substituents on the phenyl are from 1 to 3 of halogen, $C_1-C_6$ alkyl, $C_1-C_6$ alkoxy or hydroxy;

$R^4$, $R^{4a}$, $R^{4b}$, $R^5$ and $R^{5a}$ are independently hydrogen, $C_1-C_{10}$ alkyl, substituted $C_1-C_{10}$ alkyl, where the substituents on the alkyl are from 1 to 3 of hydroxy, $C_1-C_3$ alkoxy, fluoro, $R^1$, $R^2$ independently disubstituted phenyl, $C_1-C_{20}$ alkanoyloxy, $C_1-C_5$ alkoxycarbonyl or carboxy;

$R^6$ is hydrogen;

A is

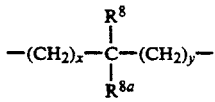

where x and y are independently 0-1;

$R^8$ and $R^{8a}$ are independently hydrogen, $C_1-C_{10}$ alkyl, substituted $C_1-C_{10}$ alkyl where the substituents are from 1 to 3 of imidazolyl, indolyl, hydroxy, fluoro, $S(O)_mR^{7a}$, $C_1-C_6$ alkoxy, $R^1$, $R^2$ independently disubstituted phenyl, $C_1-C_5$-alkanoyloxy, $C_1-C_5$ alkoxycarbonyl, carboxy; or $R^8$ and $R^{8a}$ can be taken together to form $-(CH_2)_r-$ where t is 2; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms;

and pharmaceutically acceptable salts thereof.

5. A compound of claim 1 which is:

3-amino-N-[1-[[3-(2-carboxamidophenyl)-5-isoxazolyl]methyl]-2,3,4,5-tetrahydro-2-oxo-1H-1-benzazepin-3(R)-yl]-3-methylbutanamide;

3-amino-N-[1-[[3-(2-[1H-tetrazol-5-yl]-phenyl)-5-isoxazolyl]methyl]-2,3,4,5-tetrahydro-2-oxo-1H-1-benzazepin-3(R)-yl]-3-methylbutanamide;

3-amino-N-[1-[[3-(2-[methylaminocarbonylamino]phenyl)-5-isoxazolyl]methyl]-2,3,4,5-tetrahydro-2-oxo-1H-1-benzazepin-3(R)-yl]-3-methylbutanamide;

3-[2(R)-hydroxypropyl]amino-N-[1-[[3-(2-carboxamidophenyl)-5-isoxazolyl]methyl]-2,3,4,5-tetrahydro-2-oxo-1H-1-benzazepin-3(R)-yl]-3-methylbutanamide;

2-amino-N-[1-[[3-(2-[1H-tetrazol-5-yl]-phenyl)-5-isoxazolyl]methyl]-2,3,4,5-tetrahydro-2-oxo-1H-1-benzazepin-3(R)-yl]-2-methylpropanamide;

3-amino-N-[1-[[5-(2-carboxamidophenyl)-2-thienyl]methyl]-2,3,4,5-tetrahydro-2-oxo-1H-1-benzazepin-3(R)-yl]-3-methylbutanamide;

3-amino-N-[1-[[5-(2-[1H-tetrazol-5-yl]-phenyl)-2-thienyl]methyl]-2,3,4,5-tetrahydro-2-oxo-1H-1-benzazepin-3(R)-yl]-3-methylbutanamide;

3-amino-N-[1-[[5-(2-[methylaminocarbonylamino]phenyl)-2-thienyl]methyl]-2,3,4,5-tetrahydro-2-oxo-1H-1-benzazepin-3(R)-yl]-3-methylbutanamide;

3-[2(R)-hydroxypropyl]amino-N-[1-[[5-(2-carboxamidophenyl)-2-thienyl]methyl]-2,3,4,5-tetrahydro-2-oxo-1H-1-benzazepin-3(R)-yl]-3-methylbutanamide;

2-amino-N-[1-[[5-(2-[1H-tetrazol-5-yl]-phenyl)-2-thienyl]methyl]-2,3,4,5-tetrahydro-2-oxo-1H-1-benzazepin-3(R)-yl]-2-methylpropanamide;

3-amino-N-[1-[4-(2-carboxamido-3-thienyl)-benzyl]-2,3,4,5-tetrahydro-2-oxo-1H-1-benzazepin-3(R)-yl]-3-methylbutanamide;

3-amino-N-[1-[4-(2-[1H-tetrazol-5-yl]-3-thienyl)-benzyl]-2,3,4,5-tetrahydro-2-oxo-1H-1-benzazepin-3(R)-yl]-3-methylbutanamide;

3-amino-N-[1-[4-(2-[methylaminocarbonylamino]-3-thienyl)-benzyl]-2,3,4,5-tetrahydro-2-oxo-1H-1-benzazepin-3(R)-yl]-3-methylbutanamide;

3-[2(R)-hydroxypropyl]amino-N-[1-[4-(2-carboxamido-3-thienyl)-benzyl]-2,3,4,5-tetrahydro-2-oxo-1H-1-benzazepin-3(R)-yl]-3-methylbutanamide;

2-amino-N-[1-[4-(2-[1H-tetrazol-5-yl]-3-thienyl)-benzyl]-2,3,4,5-tetrahydro-2-oxo-1H-1-benzazepin-3(R)-yl]-2-methylpropanamide;

3-amino-N-[1-[[4-(2-carboxamidophenyl)-cyclohexyl]methyl]-2,3,4,5-tetrahydro-2-oxo-1H-1-benzazepin-3(R)-yl]-3-methylbutanamide;

3-amino-N-[1-[[4-(2-[1H-tetrazol-5-yl]-phenyl)-cyclohexyl]methyl]-2,3,4,5-tetrahydro-2-oxo-1H-1-benzazepin-3(R)-yl]-3-methylbutanamide;

3-amino-N-[1-[[4-(2-[methylaminocarbonylamino]phenyl)-cyclohexyl]methyl]-2,3,4,5-tetrahydro-2-oxo-1H-1-benzazepin-3(R)-yl]-3-methylbutanamide;

3-[2(R)-hydroxypropyl]amino-N-[1-[[4-(2-carboxamidophenyl)-cyclohexyl]methyl]-2,3,4,5-tetrahydro-2-oxo-1H-1-benzazepin-3(R)-yl]-3-methylbutanamide;

2-amino-N-[1-[[4-(2-[1H-tetrazol-5-yl]-phenyl)-cyclohexyl]methyl]-2,3,4,5-tetrahydro-2-oxo-1H-1-benzazepin-3(R)-yl]-2-methylpropanamide;

3-amino-N-[1-[[4-(2-carboxamidophenyl)-cyclohexenyl]methyl]-2,3,4,5-tetrahydro-2-oxo-1H-1-benzazepin-3(R)-yl]-3-methylbutan-amide;

3-amino-N-[1-[[4-(2-[1H-tetrazol-5-yl]-phenyl)-cyclohexenyl]methyl]-2,3,4,5-tetrahydro-2-oxo-1H-1-benzazepin-3(R)-yl]-3-methylbutan-amide;

3-amino-N-[1-[[4-(2-[methylaminocarbonylamino]phenyl)-cyclohexenyl]methyl]-2,3,4,5-tetrahydro-2-oxo-1H-1-benzazepin-3(R)-yl]-3-methylbutanamide;

3-[2(R)-hydroxypropyl]amino-N-[1-[[4-(2-carboxamidophenyl)-cyclohexenyl]methyl]-2,3,4,5-tetrahydro-2-oxo-1H-1-benzazepin-3(R)-yl]-3-methylbutanamide;

2-amino-N-[1-[[4-(2-[1H-tetrazol-5-yl]-phenyl)-cyclohexenyl]methyl]-2,3,4,5-tetrahydro-2-oxo-1H-1-benzazepin-3(R)-yl]-2-methylpropanamide;

3-amino-N-[1-[4-(4-carboxamido-5-oxazolyl)-benzyl]-2,3,4,5-tetrahydro-2-oxo-1H-1-benzazepin-3(R)-yl]-3-methylbutanamide;

3-amino-N-[1-[4-(4-[1H-tetrazol-5-yl]-5-oxazolyl)-benzyl]-2,3,4,5-tetrahydro-2-oxo-1H-1-benzazepin-3(R)-yl]-3-methylbutanamide;

3-amino-N-[1-[4-(4-[methylaminocarbonylamino]-5-oxazolyl)-benzyl]-2,3,4,5-tetrahydro-2-oxo-1H-1-benzazepin-3(R)-yl]-3-methylbutanamide;

3-[2(R)-hydroxypropyl]amino-N-[1-[4-(4-carboxamido-5-oxazolyl)-benzyl]-2,3,4,5-tetrahydro-2-oxo-1H-1-benzazepin-3(R)-yl]-3-methylbutanamide;

2-amino-N-[1-[4-(4-[1H-tetrazol-5-yl]-5-oxazolyl)-benzyl]-2,3,4,5-tetrahydro-2-oxo-1H-1-benzazepin-3(R)-yl]-2-methylpropanamide;

3-amino-N-[1-[4-(4-bromo-2-carboxamido-1-pyrrolyl)-benzyl]-2,3,4,5-tetrahydro-2-oxo-1H-1-benzazepin-3(R)-yl]-3-methyl-butanamide;

3-amino-N-[1-[4-(4-bromo-2-[1H-tetrazol-5-yl]-1-pyrrolyl)-benzyl]-2,3,4,5-tetrahydro-2-oxo-1H-1-benzazepin-3(R)-yl]-3-methylbutanamide;

3-amino-N-[1-[4-(4-bromo-2-[methylaminocarbonylamino]-1-pyrrolyl)benzyl]-2,3,4,5-tetrahydro-2-oxo-1H-1-benzazepin-3(R)-yl]-3-methylbutanamide;

3-[2(R)-hydroxypropyl]amino-N-[1-[4-(4-bromo-2-carboxamido-1-pyrrolyl)-benzyl]-2,3,4,5-tetrahydro-2-oxo-1H-1-benzazepin-3(R)-yl]-3-methylbutanamide;

or 2-amino-N-[1-[4-(4-bromo-2-[1H-tetrazol-5-yl]-1-pyrrolyl)-benzyl]-2,3,4,5-tetrahydro-2-oxo-1H-1-benzazepin-3(R)-yl]-2-methylpropanamide.

6. A stereospecific compound of claim 1 which is:

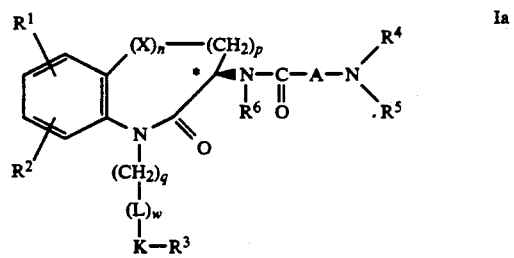

7. A method for increasing levels of endogenous growth hormone in a human or an animal which comprises administering to such human or animal an effective amount of a compound of claim 1.

8. A composition useful for increasing the endogenous production or release of growth hormone in a human or an animal which comprises an inert carrier and an effective amount of a compound of claim 1.

* * * * *